United States Patent

Aono et al.

[11] Patent Number: 6,054,591
[45] Date of Patent: Apr. 25, 2000

[54] LYMPH-ABSORBABLE ARYL SUBSTITUTED IMIDAZOLE DERIVATIVES

[75] Inventors: Katsutoshi Aono, Nara; Teruhisa Ichihashi, Kobe; Tamio Sugawara, Sanda; Koichiro Hirano, Hyogo, all of Japan

[73] Assignee: Shionogi & Co., Ltd., Japan

[21] Appl. No.: 09/101,960

[22] PCT Filed: Mar. 14, 1997

[86] PCT No.: PCT/JP97/00813

§ 371 Date: Jul. 21, 1998

§ 102(e) Date: Jul. 21, 1998

[87] PCT Pub. No.: WO97/35843

PCT Pub. Date: Oct. 2, 1997

[30] Foreign Application Priority Data

Mar. 28, 1996 [JP] Japan ................................. 8-103299

[51] Int. Cl.[7] ...................... C07D 233/84; C07D 233/58; A61K 31/415
[52] U.S. Cl. .................. 548/319.1; 514/398; 514/399; 514/400; 514/341; 548/320.5; 548/321.1; 548/322.5; 548/323.1; 548/323.5; 548/334.5; 548/341.1; 548/341.5
[58] Field of Search ................ 548/319.1, 320.5, 548/321.1, 322.5, 341.5, 323.1, 323.5, 333.5, 334.5, 341.1; 514/398, 399, 400, 341; 546/274.4

[56] References Cited

U.S. PATENT DOCUMENTS 5,326,780  7/1994  Sugimoto et al. ..................... 514/398
5,472,965  12/1995  Sugimoto et al. ..................... 514/252

FOREIGN PATENT DOCUMENTS 5-255270  7/1993  Japan .

OTHER PUBLICATIONS

Ichihashi et al, Pharmaceutical Research, vol. 8, No. 10, pp. 1302–1306, 1991.

Ichihashi et al, Pharmaceutical Research, vol. 11, No. 4, pp. 508–512, 1994.

*Primary Examiner*—Floyd D. Higel
*Attorney, Agent, or Firm*—Wenderoth, Lind & Ponack, L.L.P.

[57] ABSTRACT

A compound of the formula (I):

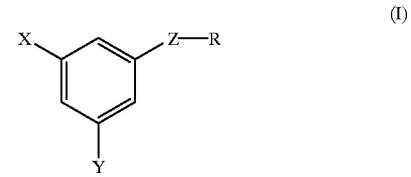

salt thereof, or hydrate thereof which can effectively be absorbed from the lymph vessel in the intestinal tract and transferred to the lymph node in a high concentration is provided.

6 Claims, No Drawings

LYMPH-ABSORBABLE ARYL SUBSTITUTED IMIDAZOLE DERIVATIVES

This is a 371 of PCT/JP97/00813, filed Mar. 14, 1997

TECHNICAL FIELD

The present invention relates to imidazole derivatives which are effectively absorbed from the intestinal tract to the lymphatic system and transferred to the lymph node in a high concentration and to pharmaceutical compositions comprising them, particularly anti-AIDS agents.

BACKGROUND ART

As agents for treating acquired immunodeficiency syndrome (AIDS), some of nucleoside derivatives (AZT, ddI, ddC, D4T, 3TC) are being used clinically. Studies have been focused also on non-nucleoside derivatives (Nevirapine, HEPT derivatives, TIBO derivatives, and the like) which are different from the nucleoside derivatives in the mechanisms of action, act specifically against HIV-1, and do not show cross resistance to them. It has been reported that a series of imidazole derivatives as one of the non-nucleoside derivatives show anti-HIV activity other than AZT and the like (JP-A 5-255270, WO 96/10019, and the like).

In recent years, as an attractive phenomenon, it has been made clear that HIV viruses keep propagating actively in the infected lymph node in asymptomatic patients who have been thought to be in the conditions of latent infection (Multifactorial nature of human immunodeficiency virus disease: Implications for therapy, Science, 262, 1011–1018 (1993), Anthony Fauci.).

In order to increase efficiency of anti-AIDS agents, it has been suggested that the concentration in the lymph node should be elevated. There is a report that some nucleoside derivatives such as AZT and the like satisfy the above object (Antiviral Chemistry & Chemotherapy (1995) 6 (4), 230). However, there is not such a report on the non-nucleoside derivatives such as the above imidazole derivatives and the like.

DISCLOSURE OF INVENTION

The present inventors found it important to elevate concentrations of anti-AIDS agents in the lymph node in order to increase their efficiency and intensively studied lymphotropic agents. As a result they found that the compound of the formula (I):

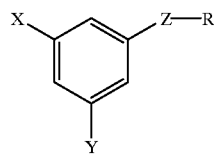

wherein X and Y each is independently hydrogen, lower alkyl, halogen or nitro;

Z is S, SO, $SO_2$ or $CH_2$; and

R is a group of the formula:

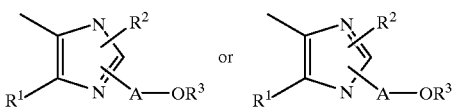

wherein $R^1$ is optionally substituted lower alkyl; $R^2$ is optionally substituted lower alkyl, optionally substituted lower alkenyl, optionally substituted cycloalkylalkyl, optionally substituted lower aroylalkyl, optionally substituted aralkyl, optionally substituted heteroarylalkyl or optionally substituted carbamoyloxyalkyl;

A is lower alkylene which may be intervened by a hetero atom; and $R^3$ is 1) $C_{11}$–$C_{20}$ alkyl,
2) acyloxyalkyl,
3) —$CR^4R^5(OR^6)$
wherein $R^4$ and $R^5$ each is independently hydrogen, optionally substituted alkyl, optionally substituted aryl, optionally substituted aralkyl, or taken together form optionally substituted cyclic alkyl or o-biphenylenemethane together with the adjacent carbon atom; and $R^6$ is optionally substituted alkyl,
4) —$C(=CR^7R^8)R^9$
wherein $R^7$, $R^8$ and $R^9$ each is independently hydrogen, optionally substituted alkyl, or $R^7$ and $R^9$ form optionally substituted cyclic alkenyl taken together with the adjacent carbon atom,
5) —$COR^{10}$
wherein $R^{10}$ is $C_6$–$C_{20}$ alkyl, cycloalkyl, optionally substituted aralkyl, or —B—$COOR^{11}$
wherein B is alkylene or alkenylene; and $R^{11}$ is hydrogen, alkyl, alkanoyloxymethyl, alkoxycarbonylmethyl, —$CH(CH_2OCOR^{12})_2$ wherein $R^{12}$ is hydrogen or alkyl, or optionally substituted heteroarylalkyl,
6) —$COOR^{13}$
wherein $R^{13}$ is $C_6$–$C_{20}$ alkyl, substituted aryl, optionally substituted aralkyl, or optionally substituted heteroarylalkyl,
7) —$CONHCOR^{14}$
wherein $R^{14}$ is hydrogen, alkyl, alkenyl, cycloalkylalkyl, optionally substituted aryl, optionally substituted aralkyl, or optionally substituted heteroarylalkyl,
8) —$CONHCOOR^{15}$
wherein $R^{15}$ is alkyl, alkenyl, cycloalkylalkyl, optionally substituted aryl, optionally substituted aralkyl, or optionally substituted heteroarylalkyl, or
9) —$CONHCH_2NR^{16}R^{17}$
wherein $R^{16}$ and $R^{17}$ each is independently optionally substituted alkyl, optionally substituted aralkyl, or form an optionally substituted heterocyclic ring taken together with the adjacent nitrogen atom, salt thereof, or hydrate thereof (referred to as the compound of the present invention) is effectively absorbed from the intestinal tract to the lymphatic system and can be transferred to the lymph node in a high concentration.

After the compound of the present invention is absorbed in the lymph, it shows its activity with the structure unchanged or changed by the in vivo hydrolysis conversion into the active compound.

BEST MODE FOR CARRYING OUT THE INVENTION

Preferred examples of the present invention are exemplified below.

① The compound wherein X and Y each is independently lower alkyl or halogen; Z is S; $R^1$ is isopropyl; $R^2$ is lower alkyl or heteroarylalkyl; and A is $C_1$–$C_3$ alkylene which may be intervened by oxygen atom.

② The compound wherein X and Y are halogen; $R^2$ is pyridylmethyl or methyl; A is methylene or ethylene; $R^3$ is —CONHCH$_2$NR$^{16}$R$^{17}$ wherein $R^{16}$ and $R^{17}$ are as defined above, —CR$^4$R$^5$(OR$^6$) wherein $R^4$, $R^5$ and $R^6$ are as defined above, or —C(=CR$^7$R$^8$)R$^9$ wherein $R^7$,$R^8$ and $R^9$ are as defined above.

③ The compound wherein X and Y are chlorine atom; Z is S; $R^1$ is isopropyl; $R^2$ is pyridylmethyl; A is methylene; $R^3$ is —CONHCH$_2$NR$^{16}$R$^{17}$ wherein $R^{16}$ and $R^{17}$ are n-butyl or benzyl, or $R^{16}$ and $R^{17}$ form morpholino taken together with adjacent nitrogen atom.

④ The above compound which can be converted into a compound wherein $R^3$ is hydrogen or —CONH$_2$ by the in vivo hydrolysis.

The terms used throughout the present specification are exemplified below.

The term "lower alkyl" means straight or branched $C_1$–$C_6$ alkyl, for example, methyl, ethyl, n-propyl, i-propyl, n-butyl, i-butyl, tert-butyl, n-pentyl, i-pentyl, n-hexyl, and the like. Preferred is $C_1$–$C_3$ alkyl.

The term "alkyl" means straight or branched $C_1$–$C_{20}$ alkyl, for example, methyl, ethyl, n-propyl, i-propyl, n-butyl, i-butyl, tert-butyl, n-pentyl, i-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, and the like.

The term "$C_6$–$C_{20}$ alkyl" means straight or branched $C_6$–$C_{20}$ alkyl.

The term "$C_{11}$–$C_{20}$ alkyl" means straight or branched $C_{11}$–$C_{20}$ alkyl.

The term "halogen" means F, Cl, Br, I.

The term "lower alkenyl" means straight or branched $C_2$–$C_7$ alkenyl, for example, vinyl, allyl, propenyl, butenyl, pentenyl, hexenyl, heptenyl, and the like.

The term "cycloalkyl" means $C_3$–$C_{12}$ cycloalkyl, for example, cyclopropyl, cyclobutyl, cyclopentyl, cyclohexyl, cycloheptyl, cyclooctyl, and the like.

The term "cycloalkylalkyl" means the above alkyl substituted with the above cycloalkyl, for example, cyclopropylmethyl, cyclopropylethyl (e.g., 1-cyclopropylethyl), cyclopropylpropyl (e.g., 2-cyclopropylpropyl), cyclopropylbutyl (e.g., 3-cyclopropylbutyl), cyclopropylpentyl (e.g., 5-cyclopropylpentyl), cyclopropylhexyl (e.g., 4-cyclopropylhexyl), cyclopropylheptyl (e.g., 6-cyclopropylheptyl), cyclopropyloctyl (e.g., 7-cyclopropyloctyl), cyclopropylnonyl (e.g., 8-cyclopropylnonyl), cyclobutylmethyl, cyclobutylethyl (e.g., 1-cyclobutylethyl), cyclobutylpropyl (e.g.,3-cyclobutylpropyl), cyclobutylbutyl (e.g., 4-cyclobutylbutyl), cyclobutylpentyl (e.g., 5-cyclobutylpentyl), cyclobutylhexyl (e.g., 6-cyclobutylhexyl), cyclobutylheptyl (e.g., 7-cyclobutylheptyl), cyclobutyloctyl (e.g., 8-cyclobutyloctyl), cyclopentylmethyl, cyclopentylethyl (e.g., 2-cyclopentylethyl), cyclopentylpropyl (e.g., 3-cyclopentylpropyl), cyclopentylbutyl (e.g., 4-cyclopentylbutyl), cyclopentylpentyl (e.g., 5-cyclopentylpentyl), cyclopentylhexyl (e.g., 6-cyclopentylhexyl), cyclopentylheptyl (e.g., 7-cyclopentylheptyl), cyclohexylmethyl, cyclohexylethyl, (e.g., 2-cyclohexylethyl), cyclohexylpropyl (e.g., 3-cyclohexylpropyl), cyclohexylbutyl (e.g., 4-cyclohexylbutyl), cyclohexylpentyl (e.g., 5-cyclohexylpentyl), cyclohexylhexyl (e.g., 6-cyclohexylhexyl), cycloheptylmethyl, cycloheptylethyl (e.g., 1-cycloheptylethyl), cycloheptylpropyl (e.g., 3-cycloheptylpropyl), cycloheptylbutyl (e.g., 4-cycloheptylbutyl), cycloheptylpentyl (e.g., 5-cycloheptylpentyl), cycloheptylmethyl, cyclooctylethyl (e.g., 2-cyclooctylethyl), cyclooctylpropyl (e.g., 3-cyclooctylpropyl), cyclooctylbutyl (e.g., 4-cyclooctylbutyl), cyclooctylethyl (e.g., 1-cyclooctylethyl), cyclononylpropyl (e.g., 2-cyclononylpropyl), and the like.

The term "aroylalkyl" means $C_8$–$C_{13}$ aroylalkyl, for example, benzoylmethyl, benzoylethyl (e.g., 1-benzoylethyl), benzoylpropyl (e.g., 3-benzoylpropyl), benzoylbutyl (e.g., 4-benzoylbutyl), benzoylpentyl (e.g., 5-benzoylpentyl), benzoylhexyl (e.g., 6-benzoylhexyl), benzoylheptyl (e.g., 7-benzoylheptyl), and the like.

The term "aryl" means phenyl, naphthyl, and the like.

The term "aralkyl" means $C_7$–$C_{12}$ aralkyl, for example, phenylmethyl, phenylethyl (e.g., 1-phenylethyl), phenylpropyl (e.g., 3-phenylpropyl), phenylbutyl (e.g., 4-phenylbutyl), phenylpentyl (e.g., 5-phenylpentyl), phenylhexyl (e.g., 6-phenylhexyl), phenylheptyl (e.g., 7-phenylheptyl), naphthylmethyl (e.g., α-naphthylmethyl), naphthylethyl (e.g.,1-naphthylethyl), and the like.

The term "heteroarylalkyl" includes pyridylmethyl (e.g., 2-pyridylmethyl), pyridylethyl (e.g., 1- or 2- (2-pyridyl) ethyl, 1- or 2- (3-pyridyl)ethyl, or 1- or 2- (4-pyridyl)ethyl), pyridylpropyl (e.g., 1-, 2- or 3- (2-pyridyl)propyl), thienylmethyl (e.g., 2-thienylmethyl or 3-thienylmethyl), quinolylmethyl (e.g., 2-quinolylmethyl, 3-quinolylmethyl, or 4-quinolylmethyl), imidazolylmethyl (e.g., 2-imidazolylmethyl), and the like.

The term "carbamoyloxyalkyl" includes carbamoyloxymethyl, carbamoyloxyethyl (e.g., 1- or 2-carbamoyloxyethyl), carbamoyloxypropyl (e.g., 1-, 2- or 3-carbamoyloxypropyl), carbamoyloxybutyl (e.g., 1-, 2-, 3- or 4-carbamoyloxybutyl), and the like.

The lower alkylene in A means $C_1$–$C_6$ alkylene which may be intervened by O, S, NH, and the like. Preferred are —(CH$_2$)m—(m=1–3), —CH$_2$OCH$_2$CH$_2$—, and the like.

The term "acyloxyalkyl" means the above alkyl substituted with acyloxy and the acyl includes formyl, acetyl, propionyl, butyryl, valeryl, and the like.

The cyclic alkyl formed by $R^4$ and $R^5$ together with the adjacent carbon atom includes monocyclic, polycyclic, condensed cyclic, or bicyclic alkyl, having 4 or more, preferably 4–15 carbon atoms, for example, cycloalkyl (e.g., cyclobutyl, cyclopentyl, cyclohexyl, cycloheptyl, cyclooctyl, cyclodecyl, cyclododecyl, and the like), adamantyl, bicyclo[2.2.1]heptyl, fluorene, and the like.

The cyclic alkenyl formed by $R^7$ and $R^9$ together with the adjacent carbon atom includes monocyclic or polycyclic (including bicyclic) alkenyl, having 4 or more, preferably 4–15 carbon atoms, for example, cycloalkenyl derived from the above cycloalkyl (cyclobutenyl, cyclopentenyl, cyclohexenyl, cycloheptenyl, cyclkooctenyl, cyclodecenyl, cyclododecenyl, and the like), dihydronaphthyl, benzocycloheptenyl, bicyclo[2.2.1]pentenyl, and the like.

The term "alkylene" means $C_1$–$C_{18}$ alkylene, for example, methylene, dimethylene, trimethylene, and the like.

The term "alkenylene" means a group derived from the above alkyl having at least one double bond, for example, vinylene, propenylene, and the like.

The term "alkanoyloxymethyl" means methyl substituted by alkanoyloxy derived from the above lower alkyl, for example, acetyloxymethyl, and the like.

The term "alkoxycarbonylmethyl" means methyl substituted by alkoxycarbonyl derived from the above lower alkyl, for example, methoxycarbonylmethyl, and the like.

The term "alkenyl" means $C_2$–$C_{20}$ alkenyl derived from the above alkyl.

The heterocyclic ring formed by $R^{16}$ and $R^{17}$ together with the adjacent nitrogen atom means 5–7 membered heterocyclic ring including at least one nitrogen atom, preferred is an aliphatic heterocyclic ring. The heterocyclic ring may additionally include an atom selected from the atoms O, S and N. The heterocyclic ring includes pyrrole, piperidine, piperazine, morpholine, and the like.

In the case each of the above groups is substituted, the substituent includes, for example, alkyl (e.g., methyl, ethyl, isopropyl, 5-(3,5-dimethylphenylthio)-4-isopropyl-2-methyl-1H-imidazol-1-ylmethyl, or 5-(3,5-dichlorophenylthio)-4-isopropyl-1-methyl-1H-imidazol-2-ylethyl), alkenyl (e.g., allyl), cycloalkyl (e.g., cyclopropyl), haloalkyl (e.g., fluoromethyl), oxoalkyl (e.g., acetylmethyl), aryl (e.g., phenyl or naphthyl), aralkyl (e.g., benzyl), heteroarylalkyl (e.g., pyridylmethyl), aroylalkyl (benzoylmethyl), substituted or unsubstituted amino (e.g., N-methylamino, N,N-dimethylamino, N-acetylamino, diaminomethyleneamino and, ureido, or methansulfonyl), acyl (e.g., acetyl, propionyl, and the like), halogen, hydroxy, oxo, alkoxy, acyloxy, cyano, carboxy, alkoxycarbonyl, phenylthio (e.g., 3,5-dichlorophenylthio), and the like. These substituents all can be substituted at one or more of any possible positions.

The compounds of the present invention were synthesized to elevate the lymph absorption of imidazole derivatives described in WO96/10019. In the imidazole derivatives, the compounds having an alcoholic hydroxy or a carbamoyloxy group as the substituents on the side chain bonded to the imidazole ring show particularly potent anti-HIV activity. Accordingly, some of the compounds of the present invention which are absorbed in the lymph and converted by in vivo hydrolysis into the derivatives having an alcoholic hydroxy or a carbamoyloxy group are desirable as superior anti-AIDS agents because they show particularly potent anti-HIV activity. Some of the compounds of the invention are absorbed in the lymph, without being hydrolyzed, to show anti-HIV activity with the structure unchanged.

Preferably, the compounds of the present invention are synthesized by introducing various lipophilic groups into imidazole derivatives having an alcoholic hydroxy or a carbamoyloxy group described in the above PCT application.

The representative compounds of the present invention can be classified as follows based upon types of the chemical modification parts ($R^3$).

(1) The ketal type derivatives ($R^3$=—$CR^4R^5(OR^6)$) and the enol ether type derivatives ($R^3$=—$C(=CR^7R^8)R^9$) prepared by introducing lipophilic groups through an ether bond into the imidazole derivatives having an alcoholic hydroxy group.

(2) The ester type derivaties ($R^3$=—$COR^{10}$) prepared by introducing lipophilic groups directly or indirectly through dicarboxylic acid in the use of an ester bond into the imidazole derivatives having an alcoholic hydroxy group.

(3) The N-acylcarbamate type derivatives ($R^3$=—$CONHCOR^{14}$) and N-alkoxycarbamate type derivatives ($R^3$=—$CONHCOOR^{15}$) derived from the imidazole derivatives having alcoholic hydroxy.

(4) The Mannich base type derivatives ($R^3$=—$CONHCH_2NR^{16}R^{17}$) prepared by introducing lipophilic groups through a Mannich base bond into the imidazole derivatives having a carbamoyloxy group.

The compounds of the present invention represented by the formula (I) can be prepared by introducing the group corresponding to the substituent $R^3$ into an alcoholic compound represented by the formula (II) as a starting material.

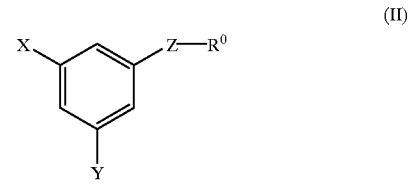

(II)

wherein X, Y and Z are as defined above and $R^0$ represents partial structure,

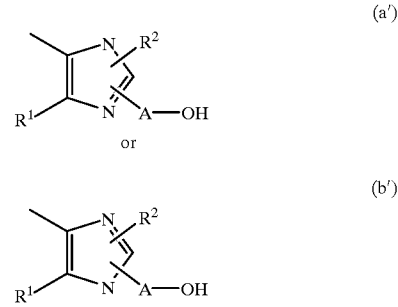

wherein A, $R^1$ and $R^2$ are as defined above.

The alcoholic compound of the formula (II) as a starting material can be prepared in accordance with methods described in WO96/10019. Corresponding to the variation of the substituent $R^3$, the process of the objective compounds (I) of the present invention from the alcoholic compounds (II) as a starting material is hereinafter explained in detail.

(1) Preparation of the compounds (I) wherein $R^3$ is $C_{11}$–$C_{20}$ alkyl

In this process, the compounds can be prepared in accordance with ordinary conditions of the alkylation of aliphatic alcohols. For example, the compounds (II) may be reacted with halogenated $C_{11}$–$C_{20}$ alkyl in the presence of a base. A base includes, for example, alkali metal hydroxide (sodium hydroxide, potassium hydroxide, and the like), organic base (potassium·tert-butoxide, picoline, lutidine, triethylamine, and the like) and the like. The reaction may be carried out in an organic solvent (dimethylformamide, dimethylsulfoxide, t-butanol, and the like) at room temperature or under heating.

(2) Preparation of the compounds (I) wherein $R^3$ is acyloxyalkyl

In this process, the compounds can be prepared by introducing a hydroxyalkyl group into a portion of an alcohol in the compound (II), and subsequently by acylation of a hydroxy group in hydroxyalkyl. For example, in the case that an alkyl portion of acyloxyalkyl is ethyl, the objective acyloxyethyl derivatives (I) can be prepared by reacting the compound (II) with ethyleneoxide to give a hydroxyethyl compound, followed by usual acylation.

(3) Preparation of the compounds (I) wherein $R^3$ is —$CR^4R^5(OR^6)$

In this process, the compounds can be prepared by reacting the compound (II) as a starting material with the acetal or ketal derivatives of the formula $CR^4R^5(OR^6)_2$ (III) wherein $R^4$, $R^5$ and R6 are as defined above. In this reaction, one of $OR^6$ of the compound (III) is substituted with a hydroxy group of the compound (II) to obtain the compound (I) wherein $R^3$ is —$CR^4R^5(OR^6)$. Examples of the compound (III) include ketal derivatives of aliphatic or chained ketone, specifically, 1,1-dimethoxycyclopentane, 1,1-dihexyloxycyclopentane, 1,1-dimethoxycyclohexane, 1,1-dibutoxycyclohexane, 4-t-butyl-1,1-dimethoxycyclohexane, 1,1 -dimethoxycycloheptane, 2,2-dimethoxycycloheptane, 1,1-diethoxycycloheptane, 1,1-dipropoxycycloheptane, 1,1-dibutoxycycloheptane, 1,1-dimethoxycyclooctane, 1,1-dibutoxycyclooctane, 1,1-dimethoxycyclodecane, 1,1-dimethoxycyclododecane, 1,1-diethoxycyclododecane, 2,2-dimethoxybicyclo[2.2.1]heptane, 2,2-diethoxybicyclo[2.2.1]heptane, 2,2-dimethoxy-1,7,7-trimethylbicylo[2.2.1]heptane, 1,1-diethoxy-1,7,7-trimethylbicyclo[2.2.1]heptane, 2,2-dimethoxyadamantane, 2,2-diethoxyadamantane, 1,1-dimethoxybenzophenone, 9,9-dimethoxyfluorene, 2,2-dimethoxypropane, 2,2-dimethoxybutane, 2,2-dimethoxypentane, 2,2-dimethoxyhexane, 2,2-dimethoxyheptane, 2,2-dimethoxyoctane, and the like. The reaction can ordinarily be carried out by reacting an excess amount of the compound (III) under an acid catalyst (hydrochloric acid, oxalic acid, ammmonium chloride, ammmonium nitric acid, p-toluene sulfonic acid, p-toluene sulfonic acid pyridinium salt, mesitylenesulfonic acid, camphor sulfonic acid, acid type ion-exchange resin, and the like) in an organic solvent (benzene, toluene, methylene chloride, ethylene chloride, ethylether, tetrahydrofuran, ethyl acetate, acetonitrile, N,N-dimethylformamide, dimethylsulfoxide, and the like). Preferred reaction temperature is from 0° C. to room temperature and reaction time is 1–24 hours.

(4) Preparation of the compounds (I) wherein $R^3$ is —$C(=CR^7R^8)R^9$

In this process, the compounds can be prepared by reacting the compound (II) as a starting material with enol ether derivatives of the formula $R^9(R^6O)C=CR^7R^8$ (IV) wherein $R^6$, $R^7$, $R^8$ and $R^9$ are as defined above. In the same manner as the above process (3), $OR^6$ of the compound (IV) is substituted with a hydroxy group of the compound (II) to give the compounds (I) wherein $R^3$ is —$C(=CR^7R^8)R^9$. Examples of the compound (IV) include enol derivatives of aliphatic or chained ketone, specifically, 1-methoxycyclopentene, 1-methoxycyclohexene, 1-methoxycycloheptene, 5-methoxy-8,9-dihydro-7H-benzocyclohept-5-ene, 1-methoxycyclooctene, 1-ethoxycyclooctene, 1-butoxycyclooctene, 1-methoxycyclodecene, 1-methoxycyclododecene, 1-methoxy-3, 4-dihydronaphthalene, 1-adamantyl methyl ketone dimethoxyacetal, and the like. The reaction can be carried out in accordance with the same reaction condition as that of the compound (II) with the ketal derivatives (III) as described above.

(5) Preparation of the compounds (I) wherein $R^3$ is —$COR^{10}$

In this process, the compounds can be prepared by reacting the compound (II) as a starting material with the carboxylic acid of the formula $R^{10}COOH$ (V) wherein $R^{10}$ is as defined above or its reactive derivatives. The carboxylic acid (V) includes chained or cyclic aliphatic carboxylic acid (heptanoic acid, octanoic acid, decanoic acid, dodecanoic acid, cyclohexylcarboxylic acid, cyclodecanoylcarboxylic acid, and the like), ararlkylcarboxylic acid (phenylacetic acid, p-methoxyphenylacetic acid, phenylpropionic acid, 3-(2-chlorophenyl)propionic acid, phenylbutanoic acid, and the like), or dibasic carboxylic acid of which one of the carboxyls may be protected (malonic acid, succinic acid, glutaric acid, 1,8-octanedicarboxylic acid, 1,10-decanedicarboxylic acid, 1,12-dodecanedicarboxylic acid, 1,14-tetradecanedicarboxylic acid, and the like; the protecting group for these carboxylic acid includes the conventional protecting groups for carboxylic acid such as 2-trimethylsilylethyl, 1,3-di(pentadecanoyloxy)-propan-2-yl, methoxycarbonylmethyl, t-butyl, and the like). The reaction can be carried out under usual conditions for acylation of hydroxy, for example, in the case of the direct reaction of the above carboxylic acids with the alcoholic compound (II), they can be reacted in the presence of a condensing agent (e.g., dicyclohexylcarbodiimide), if necessary, in the presence of a base (4-dimethylaminopyridine). Further, the reactive derivatives of the carboxylic acid (V) means the corresponding carbonyl halides (e.g., chloride, bromide), acid anhydrides (e.g., a mixed acid anhydride with ester carbonate or succinic anhydride), active esters (e.g., N-hydroxypiperidinyl ester, N-hydroxysuccinimide ester, N-hydroxyphthalimide ester, N-hydroxybenzotriazole ester, and the like), and the like. The reaction with the reactive derivatives can be carried out in the presence or absence of a base (e.g., pyridine, N,N-dimethylaniline, triethylamine, and the like) in the same manner as ordinary acylation of alcohols.

(6) Preparation of the compounds (I) wherein $R^3$ is —$COOR^{13}$

In this process, the compounds can be prepared by reacting the alcoholic compound (II) as a starting material with the carbonate halide of the formula $X—COOR^{13}$ (V) wherein $R^{13}$ is as defined above. The reaction can be carried out under the same conditions as those for the ester forming reaction of the above alcohols with the carbonyl halides.

(7) Preparation of the compounds (I) wherein $R^3$ is —$CONHCOR^{14}$

In this process, the compounds can be prepared by reacting the alcoholic compound (II) as a starting material with acyl isocyanate of the formula $R^{14}CONCO$ (VI) wherein $R^{14}$ is as defined above. Examples of the acyl isocyanate (VI) include formyl isocyanate, alkanoyl isocycnate (e.g., acetyl isocyanate, propionyl isocycnate, butyryl isocyanate, valeryl isocyanate, pivaloyl isocyanate, octanoyl isocyanate, decanoyl isocyanate, lauroyl isocycnate, palmitoyl isocyanate, myristroyl isocyanate, stearoyl isocyanate, oleoyl isocyanate, and the like), alkenoyl isocyanate (e.g., acryloyl isocyanate, methacryloyl isocyanate, isocrotonoyl isocyanate, and the like), cycloalkylalkanoyl isocyanate (e.g., cyclopropylacetyl isocyanate, cyclobutylpropionyl isocyanate, cyclopentylbutyryl isocyanate, cyclohexylvaleryl isocyanate, and the like), aroyl isocyanate (e.g., benzoyl isocyanate, 4-chlorobenzoyl isocyanate, 3,5-dichlorobenzoyl isocyanate, aralkanoyl isocyanate (e.g., phenylacetyl isocyanate, phenylpropionyl isocyanate, phenylbutyryl isocyanate, phenylvaleryl isocyanate, and the like), heteroaroyl isocyanate (e.g., furoyl isocyanate, thenoyl isocyanate, nicotinoyl isocyanate, isonicotinoyl isocyanate, and the lilke), and the like. The reaction can be carried out in an inert organic solvent (e.g., tetrahydrofuran, dimethoxyethane, and the like) at from 0° C. to room temperature for 1–4 hours.

(8) Preparation of the compounds (I) wherein $R^3$ is —$CONHCOOR^{15}$

In this process, the compounds can be prepared by reacting the alcoholic compound of the $R^{15}OH$ (VII) wherein $R^{15}$ is as defined above with isocyanocarbonyl halides (e.g., isocyanocarbonyl chloride, and the like) to give the corresponding isocyanocarboxylate ($R^{15}OCONCO$) and reacting the isocyanocarboxylate with the alcoholic compound (II) as a starting material. The alcoholic compound of the formula (VII) includes $C_1$-$C_{20}$ alkanol (e.g., methanol, ethanol, octanol, decanol, octadecanol, dodecanol, oleanol, and the like), $C_2$-$C_{20}$ alkenol (e.g., propenol, butenol, pentenol, octenol, and the like), $C_4$-$C_{12}$ cycloalkylalkanol (e.g., cyclopropylmethanol, cyclobutylethanol, cyclopentylpropanol, and the like), phenols (e.g., 2,6-diisopropylphenol, 4-phenylphenol, naphthol, cresol, and the like), arylalkanol (e.g., phenylmethanol, phenylethanol, naphthaleneethanol, and the like), heteroarylalkanol (e.g., furylmethanol, thienylethanol, quiolylmethanol, isoquionolylethanol, and the like), and the like. The reaction can be carried out by the successive step (one-pot reaction), ordinarily the reaction of the compound (VII) with the isocyanocarbonyl halides are carried out in an ether solvent such as tetrahydrofuran under cooling to 0° C. or lower for 1–2 hours, or at room temperature for 1–2 hours, then the alcoholic compound (II) as a starting material and a base such as triethylamine are added to this reaction system and allowed to react at room temperature for 5–20 hours.

(9) Preparation of the compounds (I) wherein $R^3$ is —$CONHCH_2NR^{16}R^{17}$

In this process, the alcoholic compound (II) as a starting material can be converted into the corresponding carbamoyl derivatives (the compound wherein $R^3$ is —$CONH_2$ in the formula (I)) and the carbamoyl derivatives can be condensed with the secondary amine of the formula $R^{16}R^{17}NH$ (VIII) wherein $R^{16}$ and $R^{17}$ are as defined above and formaldehyde or paraformaldehyde under Mannich reaction conditions. Examples of the secondary amine (VIII) include dialkylamine (e.g., diethylamine, dibutylamine, dioctylamine, and the like), diaralkylamine (e.g., dibenzylamine, and the like), or cyclic amine (e.g., pyrrolidine, piperidine, morpholine, and the like). The conversion of the compound (II) as a starting material into the carbamoyl can be carried out by reacting it with isocyanate (e.g., trichloroacetyl isocyanate, chlorosulfonyl isocyanate, and the like) in an organic solvent (e.g., tetrahydrofuran, dimethylsulfoxide, and the like) and deprotecting it with a base (e.g., triethylamine). The condensation of the obtained carbamoyl derivatives with the secondary amine (VIII) and formaldehyde or paraformaldehyde may be done by refluxing them in an organic solvent (e.g., ethanol, t-butanol, ethyl acetate, dioxane, and the like) from several hours to several days. The product can be purified by recrystallization or chromatography.

The compound of the present invention can be orally administered. For oral administration, the compound of the present invention can be formulated into ordinary formulations including solid preparations such as tablets, powder, granules, capsules, and the like; liquid preparations or oily suspensions; or liquid solutions such as syrup, elixirs, and the like.

In preparing such formulations, conventional additives may be used, such as carriers, binders, lubricants, aqueous solvents, oily solvents, emulsifiers, suspending agents, and the like, and additionally, preservatives, stabilizers, and the like. A dosage of the compound or its salt of the present invention depends on the administration route, age, body weight, conditions of the patient, and the kind of diseases, and in the case of oral administration, the daily dosage can generally be between 0.05–3000 mg, preferably 0.1–1000 mg, and in the case of non-oral administration, the daily dosage can generally be between 0.05–500 mg, preferably 0.1–1000 mg, and it can be administered in 1–5 divisions.

The following Examples are provided to further illustrate the present invention and are not to be construed as limiting the scope.

EXAMPLE 1

5-(3,5-Dimethylphenylthio)-4-isopropyl-1-[2-(1-methoxycyclopentyloxy)ethoxymethyl]-2-methyl-1H-imidazole (2)

(1) A solution of 5-(3,5-dimethylphenylthio)-4-isopropyl-1-(2-hydroxyethoxymethyl)-2-methyl-1H-imidazole (1) (301 mg, 0.9 mmol) prepared in accordance with the method as described in WO 96/10019 and p-toluenesulfonic acid hydrate (180 mg, 0.945 mmol) in a mixture of methylene chloride (5 mL) - toluene (1 mL) was concentrated under reduced pressure. The obtained residue was dissolved in methylene chloride (9 mL), to which was added 1,1-dimethoxycyclopentane (1.17 g, 9.00 mmol), and the mixture was stirred for 3 hours. Triethylamine (0.19 mL) was added to the reaction mixture, and the mixture was concentrated under reduced pressure. The residue was purified by chromatography on an alumina column (eluate: hexane - ethyl acetate (2:1)) to give the compound 2 (285 mg, 73 %) as oil. Rf 0.45 ($Al_2O_3$ 60, Type E, 2:1 hexane -EtOAc).

PMR ($CDCl_3$ -0.1% $d_5$-Py): $\delta$H1.26 (6 H, d, J 7.0 Hz, $(CH_3)_2CH$), 1.55–1.76 (8 H, m, -$CH_2$—), 2.21 (6 H, s, arom 3- and 5-$CH_3$), 2.53 (3 H, s, 2-$CH_3$), 3.15 (3 H, S, $CH_3O$), 3.17 (1 H, sep, J 7.0 Hz, $(CH_3)_2CH$), 3.41 (4 H, m, $OCH_2CH_2O$), 5.29 (2 H, s, $NCH_2O$), 6.59 (2 H, s, arom 2- and 6-H), 6.74 (1 H, 8, arom 4-H). Elementary analysis (for $C_{24}H_{36}N_2O_3S$) Cacld.: C, 66.63% H, 8.39% N, 6.48% Found: C, 66.24% H, 8.38% N, 6.48%

EXAMPLE 2

A solution of the compound 1 (33.4 mg, 0.1 mmol) and p-toluenesulfonic acid hydrate (20.4 mg, 0.108 mmol) in a mixture of methylene chloride (1 mL) -toluene (0.1 mL) was concentrated under reduced pressure. Trhe obtained residue was dissolved in methylene chloride (1 mL), to which was added 1-methoxycyclopentene (98.5 mg, 1 mmol), and the mixture was stirred for 2 hours. Triethylamine was added to the reaction mixture, and the mixture was concentrated under reduced pressure. The residue was purified by chromatography on an alumina column (eluate: hexane - ethyl acetate (2:1)) to give the same compound 2 (35 mg, 81 %) as the Example 1.

EXAMPLE 3

5-(3,5-Dimethylphenylthio)-4-isopropyl-1-[2-(1-methoxycyclohexyloxy)ethoxymethyl) -2-methyl-1H -imidazole (3)

The compound 1 (33.4 mg, 0.1 mmol) was converted to the acetal with 1,1-dimethoxycyclohexane (144 mg, 1.00 mmol) in the same manner as the example 1 to give the compound 3 (28 mg, 60 %). Rf 0.57 ($Al_2O_3$ 60, Type E, 2:1 hexane -EtOAc).

PMR ($CDCl_3$ -0.1% $d_5$-Py): $\delta$H1.26 (6 H, d,7.0 Hz, $(CH_3)_2CH$), 1.35–1.62 (10 H, m, cyclohexyl —$CH_2$—), 2.21 (6 H, s, arom 3- and 5-$CH_3$), 2.53 (3 H, s, 2 -$CH_3$), 3.11 (3 H, S, $CH_3O$), 3.17 (1 H, sep, 7.0 Hz, $(CH_3)_2CH$), 3.40 (4 H, m, $OCH_2CH_2O$), 5.30 (2 H, s, $NCH_2O$), 6.59 (2 H, s, arom 2- and 6-H), 6.73 (1 H, s, arom 4-H). Elementary analysis (for $C_{25}H_{38}N_2O_3S$) Calcd. C, 67.23% H, 8.58% N, 6.27% Found C, 66.90% H, 8.61% N, 6.41%

EXAMPLE 4

The compound 1 (502 mg, 1.50 mmol) was converted to the acetal with 1-methoxycyclohexene (1.68 g, 15.0 mmol) in the same manner as the example 2 to give the compound 3 (502 mg, 72%).

EXAMPLE 5

5-(3,5-Dimethylphenylthio)-4-isopropyl-1 -[2-(1-methoxycycloheptyloxy)ethoxymethyl]-2-methyl-1H-imidazole (4)

The compound 1 (301 mg, 0.9 mmol) was converted to the acetal with 1,1-dimethoxycycloheptane (1.30 g, 9 mmol) in the same manner as the example 1 to give the compound 4 (288 mg, 67%). Rf 0.68 ($Al_2O_3$ 60-type E, 2:1 hexane -EtOAc).

PMR ($CDCL_3$ -0.1% $d_5$-Py): δH1.26 (6 H, d, J 7.0 Hz, $(CH_3)_2CH$), 1.40–1.75 (12 H, m, —$CH_2$—), 2.21 (6 H, s, arom 3- and 5-$CH_3$), 2.53 (3 H, s, 2-$CH_3$), 3.10 (3 H, S, $CH_3O$), 3.18 (1 H, sep, J 7.0 Hz, $(CH_3)_2CH$), 3.40 (4 H, m, $OCH_2CH_2O$), 5.29 (2 H, s, $NCH_2O$), 6.60 (2 H, s, arom 2- and 6-H), 6.74 (1 H, s, arom 4-H). Elementary analysis (for $C_{26}H_{40}N_2O_3S$) Calcd.: C, 67.79% H, 8.75% N, 6.08% Found: C, 67.78% H, 8.88% N, 6.06%

EXAMPLE 6

1,1-Bis-{2-[5-(3,5-dimethylphenylthio)-4-isopropyl-2-methyl-1H-imidazol-3-ylmethoxy]ethoxy}cycloheptane (5)

The compound 1 (401 mg, 1.20 mmol) was converted to the acetal with 1-methoxycycloheptene (1.51 g, 12.0 mmol) in the same manner as the example 2 to give the compound 5 (40 mg, 9%) as oil. Rf 0.25 ($Al_2O_3$60-type E, 2:1 hexane -EtOAc).

PMR ($CDCl_3$ -0.1% $d_5$-Py): δH1.25 (12 H, d, J 7.0 Hz, 2 x $(CH_3)_2CH$), 1.36–1.72 (24 H, m, 2 x -$CH_2$-), 2.20 (12 H, s, 2 x arom 3- and 5-$CH_3$),2.51 (6 H, s, 2 x 2-$CH_3$), 3.16 (2 H, sep, J 7.2 Hz, $(CH_3)_2CH$), 3.35 (8 H, m, 2 x $OCH_2CH_2O$), 5.25 (4 H, s, 2 x $NCH_2O$), 6.57 (4 H, s, 2 x arom 2- and 6-H), 6.73 (2 H, s, 2 x arom 4-H). Elementary analysis (for $C_{43}H_{62}N_4O_4S_2$) Calcd.: C, 67.68% H, 8.19% N, 7.34% Found: C, 67.49% H, 8.41% N, 7.19%

EXAMPLE 7

1-[2-(Cyclohexen-1-yloxy)ethoxymethyl]-5-(3,5-dimethylphenylthio)-4-isopropyl-2-methyl-1H-imidazole (6)

A solution of the compound 1 (33.4 mg, 0.1 mmol) and p-toluenesulfonic acid hydrate (20.0 mg, 0.105 mmol) in a mixture of methylene chloride (1 mL) - toluene (0.1 mL) was concentrated under reduced pressure. The residue was dissolved in a mixture of dioxane (2 mL) - benzene (0.5 mL), to which was added 1-methoxycyclohexene (112 mg, 1.00 mmol). The reaction mixture was heated under reflux, and concentrated to a small volume over 1 hour. A drop of triethylamine was added to the reaction mixture, and the mixture was concentrated under reduced pressure. Hexane was added to the residue, the mixture was filtered to remove the insoluble matter, and the filtrate was purified by chromatography on an alumina column (eluate: hexane - ethyl acetate (2:1)) to give the same compound 6 (31 mg, 75%) as oil. Rf 0.62 ($Al_2O_3$ 60, Type E, 2:1 hexane -EtOAc).

PMR ($CDCl_3$ -0.1% $d_5$-Py): δH1.26 (6 H, d, J 7.2 Hz, $(CH_3)_2CH$), 1.45–1.70 (4 H, m, —$CH_2$—), 1.96–2.06 (4 H, m, —$CH_2$—), 2.21 (6 H, s, arom 3- and 5-$CH_3$), 2.53 (3 H, s, 2-$CH_3$), 3.17 (1 H, sep, J 7.2 Hz, $(CH_3)_2CH$), 3.55 (4 H, m, $OCH_2CH_2O$), 4.50 (1 H, t, 2.8 Hz, olefinic H), 5.30 (2 H, s, $NCH_2O$), 6.60 (2 H, s, arom 2- and 6-H), 6.74 (1 H, s, arom 4-H). Elementary analysis (for $C_{24}H_{34}N_2O_2S$) Calcd.: C, 69.53% H, 8.27% N, 6.76% Found: C, 69.58% H, 8.44% N, 6.70%

EXAMPLE 8

1-[2-(Cyclohepten-1-yloxy)ethoxymethyl]-5-(3, 5-dimethylphenylthio)-4-isopropyl-2-methyl-1H-imidazole (7)

The compound 1 (401 mg, 1.20 mmol) was converted to the enol ether with 1-methoxy-1-cycloheptene (1.51 g, 12.0 mmol) in the same manner as the example 7 to give the compound 7 (372 mg, 77%) as oil. Rf 0.75 ($Al_2O_3$ 60-type E, 2:1 hexane -EtOAc).

PMR ($CDCl_3$ -0.1% $d_5$-Py): δH1.26 (6 H, d, J 7.2 Hz, $(CH_3)_2CH$), 1.42–1.75 (6 H, m, —$CH_2$—), 2.02 (2 H, m, —$CH_2$—), 2.21 (6 H, s, 3- and 5-$CH_3$), 2.22 (2 H, m, cycloheptenyl 7-$CH_2$), 2.53 (3 H, s, 2-$CH_3$), 3.18 (1 H, sep, J 7.2 Hz, $(CH_3)_2CH$), 3.50 (4 H, bs, $OCH_2CH_2O$), 4.60 (1 H, t, 6.6 Hz, olefinic H), 5.30 (2 H, s, $NCH_2O$), 6.60 (2 H, s, arom 2- and 6-H), 6.74 (1 H, s, arom 4-H). Elementary analysis (for $C_{25}H_{36}N_2O_2S$) Cacld.: C, 70.05% H, 8.47% N, 6.54% Found: C, 69.93% H, 8.59% N, 6.30%

EXAMPLE 9

5-(3,5-Dichlorophenylthio)-4-isopropyl-1-[2-(1-methoxycycloheptyloxy)ethoxymethyl]-2-methyl-1H-imidazole (9)

5-(3,5-Dichlorophenylthio)-4-isopropyl-1-[2-hydroxyethoxymethyl]-2-methyl-1H-imidazole (8) (450 mg, 1.20 mmol) prepared in accordance with the method as described in WO 96/10019 was converted to the acetal with 1,1-dimethoxycycloheptane (1.90 g, 12.0 mmol) in the same manner as the example 1 to give the compound 9 (358 mg, 59%) as oil. Rf 0.57 ($Al_2O_3$ 60, Type E, 2:1 hexane -EtOAc).

PMR ($CDCl_3$ -0.1% $d_5$-Py): δH1.25 (6 H, d, J 7.2 Hz, $(CH_3)_2CH$), 1.45–1.76 (12 H, bm, —$CH_2$—), 2.56 (3 H, s, 2-$CH_3$), 3.11 (3 H, S, $CH_3O$), 3.11 (1 H, sep, J 7.2 Hz, $(CH_3)_2CH$), 3.37 and 3.44 (each 2 H, m, $OCH_2CH_2O$), 5.26 (2 H, s, $NCH_2O$), 6.83 (2 H, d, J 1.8 Hz, arom 2- and 6-H), 7.11 (1 H, t, J 1.8 Hz, arom 4-H). Elementary analysis (for $C_{34}H_{34}N_2O_3SCl2$) Calcd.: C, 57.48% H, 6.83% N, 5.59% Cl, 14.14% Found: C, 57.75% H, 6.99% N, 5.60% Cl, 14.10%

EXAMPLE 10

1-[2-(Cyclohepten-1-yloxy)ethoxymethyl]-5-(3,5-dichlorophenylthio)-4-isopropyl-2-methyl-1H-imidazole (10)

A solution of the compound 8 (450 mg, 1.20 mmol) and p-toluenesulfonic acid hydrate (20.0 mg, 0.105 mmol) in a mixture of methylene chloride (1 mL) - toluene (0.1 mL) was concentrated under reduced pressure. The residue was dissolved in toluene (2 mL), to which was added 1,1-dimethoxycycloheptane (1.51 g, 12.0 mmol). The reaction mixture was heated under reflux over 1 hour and concentrated to a small quantity. A drop of triethylamine was added to the reaction mixture, and the mixture was concentrated under reduced pressure. Hexane was added thereto, the mixture was filtered to remove the insoluble matter, and the filtrate was purified by chromatography on an alumina column (eluate: hexane - ethyl acetate (2:1)) to give the compound 10 (275 mg, 47%) as oil. Rf 0.64 ($Al_2O_3$ 60, Type E, 2:1 hexane -EtOAc).

PMR ($CDCl_3$ - 0.1% $d_5$-Py): δH1.25 (6 H, d, J 7.0 Hz, $(CH_3)_2CH$), 1.40–1.75 (6 H, m, —$CH_2$—), 2.03 (2 H, m, —$CH_2$—), 2.23 (2 H, m, —$CH_2$—), 2.55 (3 H, s, 2-$CH_3$), 3.10 (1 H, sep, J 7.0 Hz, $(CH_3)_2CH$), 3.54 (4 H, m, $OCH_2CH_2O$), 4.61 (1 H, t, J 6.8 Hz, olefinic H), 5.29 (2 H, s, $NCH_2O$), 6.84 (2 H, d, J 2.0 Hz, arom 2- and 6-H), 7.10 (1 H, t, J 2.0 Hz, arom 4-H). Elementary analysis (for $C_{23}H_{30}N_2O_2SCl_2$) Calcd.: C, 58.84% H, 6.44% N, 5.97% Cl,15.10% Found: C, 59.22% H, 6.65% N, 5.93% Cl,15.09%

EXAMPLE 11

1-[2-(Cycloocten-1-yloxy)ethoxymethyl]-5-(3, 5-dichlorophenylthio)-4-isopropyl-2-methyl-1H-imidazole (11)

The compound 8 (450 mg, 1.2 mmol) was converted to the enol ether with 1-methoxycyclooctene (1.51 g, 12 mmol) in the same manner as the example 10 to give the compound 11 (405 mg, 70%) as oil. Rf 0.50 ($Al_2O_3$ 60, Type E, 10:1 toluene -EtOAc).

PMR ($CDCl_3$ - 0.1% $d_5$-Py): δH1.25 (6 H, d, J 6.9Hz, $(CH_3)_2CH$), 1.45–1.55 (8 H, m, —$CH_2$—), 2.55 (3 H, s, 2-$CH_3$), 3.11 (1 H, sep, J 5.9 Hz, $(CH_3)_2CH$), 3.58 (4 H, m, $OCH_2CH_2O$), 4.38 (1 H, t, J 8.3 Hz, olefinic H), 5.30 (2 H, s, $NCH_2O$), and 6.83 (2 H, d, J 1.8 Hz, arom 2- and 6-H), 7.10 (1 H, t, J 2.0 Hz, arom 4-H). Elementary analysis (for $C_{24}H_{32}N_2O_2SCl_2$) Calcd.; C, 59.62% H, 6.67% N, 5.79% Cl, 14.67% Found: C, 60.19% H, 6.91% N, 5.67% Cl, 14.49%

EXAMPLE 12

1-[2-(Cyclodecen-1-yloxy)ethoxymethyl]-5-(3,5-dichlorophenylthio)-4-isopropyl-2-methyl-1H-imidazole (12)

The compound 8 (375 mg, 1 mmol) was converted to the enol ether with 1-methoxy-1-cyclodecene (505 mg, 3 mmol) in the same manner as the example 10 to give the compound 12 (336 mg, 66%) as oil. Rf 0.55 ($Al_2O_3$ 60, Type E, 10:1 toluene - EtOAc).

PMR ($CDCl_3$ -0.1% $d_5$-Py): δH1.26 (6 H, d, J 7.2 Hz, $(CH_3)_2CH$), 1.20–1.60 (12 H, m, —$CH_2$—), 2.18 (2 H, m, —$CH_2$—), 2.28 (2 H, t, J 6.5 Hz, —$CH_2$—), 2.54 (3 H, s, 2-$CH_3$), 3.10 (1 H, sep, J 7.0 Hz, $(CH_3)_2CH$), 3.61 (4 H, m, $OCH_2CH_2O$), 4.27 ( 1 H, t, J 8.6 Hz, =CH), 5.29 (2 H, s, $NCH_2O$), 6.84 (2 H, d, J 2.0 Hz arom 2- and 6-H), 7.10 (1 H, t, J 2.0 Hz, arom 4-H). Elementary analysis (for $C_{26}H_{36}N_2O_2SCl_2$) Calcd.: C, 61.05% H, 7.09% N, 5.48% Cl, 13.86% Found: C, 61.44% H, 7.28% N, 5.43% Cl, 13.92%

EXAMPLE 13

1 -[2-(Cyclododecen-1 -yloxy)ethoxymethyl]-5-(3, 5-dichlorophenylthio)-4-isopropyl-2-methyl-1H-imidazole (13)

The compound 8 (375 mg, 1 mmol) was converted to the enol ether with 1-methoxycyclododecene (589 mg, 3 mmol) in the same manner as the example 10 to give the compound 13 (426 mg, 79 %) as oil. Rf 0.57 ($Al_2O_3$ 60, Type E, 10:1 toluene - EtOAc).

PMR ($CDCl_3$ -0.1% $d_5$-Py): δH1.25 (6 H, d, J 7.2 Hz, $(CH_3)_2CH$), 1.20–1.56 (16 H, m, —$CH_2$—), 2.01 (2 H, q, —$CH_2$—), 2.14 (2 H, t, J 6.6 Hz, —$CH_2$—), 2.54 (3 H, s, 2-$CH_3$), 3.10 (1 H, sep, J 7.2 Hz, $(OCH_3)_2CH$), 3.59 (4 H, m, $OCH_2CH_2O$), 4.26 (1 H, t, J 8.1 Hz, =CH), 5.29 (2 H, s, $NCH_2O$), 6.84 (2 H, d, J 2.1 Hz, arom 2- and 6-H), and 7.10 (1 H, t, J 2.1 Hz, arom 4-H). Elementary analysis ($C_{28}H_{40}N_2O_2SCl_2$) Cacld.: C, 62.32% H, 7.47% N, 5.19% Cl, 13.14% Found: C, 62.73% H, 7.62% N, 5.19% Cl, 13.36%

EXAMPLE 14

5-(3,5-Dichlorophenylthio)-4-isopropyl-1-methyl-2-(1-methoxycyclohexyloxy)methyl-1H-imidazole (15)

To a solution of 5-(3,5-dichlorophenylthio)-4-isopropyl-1-methyl-2-hydroxymethyl-1H-imidazole (14) (33 mg, 0.1 mmol) prepared in accordance with the method as described in WO 96/10019 and p-toluenesulfonic acid pyridinium (27.6 mg, 0.11 mmol) in toluene (1.5 mL) was added 1-methoxycyclohexene (112 mg, 1.00 mmol) under ice-cooling, and stirred at room temperature for 6 hours. A drop of triethylamine was added to the reaction mixture, and the mixture was filtered to remove the insoluble matter. The filtrate was concentrated under reduced pressure. The residue was purified by chromatography on an alumina column (eluate: toluene) to give the compound 15 (37.0 mg, 70%) as oil. Rf 0.16 ($Al_2O_3$ 60, Type E, toluene).

PMR ($CDCl_3$ -0.1% $d_5$-Py): 6 H1.24 (6 H, d, J 6.6 Hz, $(CH_3)_2CH$), 1.32–1.75 (10 H, m, —$CH_2$—), 3.10 (1 H, sep, J 6.6 Hz, $(CH_3)_2CH$), 3.22 (3 H, s, $OCH_3$), 3.59 (3 H, s, $NCH_3$), 4.61 (2 H, s, $CH_2O$), 6.81 (2 H, d, J 2.0 Hz, arom 2- and 6-H), and 7.11 (1 H, t, J 2.0 Hz, arom 4-H). Elementary analysis (for $C_{21}H_{28}N_2O_2SCl_2$) Calcd.: C, 56.88% H, 6.36% N, 6.32% Cl, 15.99% Found: C, 57.08% H, 6.46% N, 6.37% Cl, 15.99%

EXAMPLE 15

2-[(1-Butoxycyclohexyloxy)methyl]-5-(3,5-dichlorophenylthio)-4-isopropyl-1-methyl-1H-imidazole (16)

The compound 14 (3.1 mg, 0.1 mmol) was converted to the acetal with 1,1-dibutoxycyclohexane (228 mg, 1 mmol) in the same manner as the example 14 to give the compound 16 (15 mg, 30%) as oil. Rf 0.44 ($Al_2O_3$ 60, Type E, toluene).

PMR ($CDCl_3$-0.1% $d_5$-Py): δH0.93 (3 H, t, J 7.5 Hz, $CH_3$), 1.23 (6 H, d, J 6.9 Hz, $(CH_3)_2CH$), 1.35–1.75 (14 H, m, —$CH_2$—), 3.10 (1 H, sep, J 6.9 Hz, $(CH_3)_2CH$), 3.41 (2 H, t, J 6.6 Hz, $CH_2O$), 3.58 (3 H, s, $CH_3N$), 4.63 (2 H, s, $CH_2O$), 6.80 (2 H, d, J 1.5 Hz, arom 2- and 6-H), and 7.11 (1 H, t, J 1.5 Hz, arom 4-H). Elementary analysis (for $C_{24}H_{34}N_2O_2SCl_2$) Cacld.: C, 59.37% H, 7.06% N, 5.77% Found: C, 59.45% H, 7.16% N, 5.80%

EXAMPLE 16

2-(Cyclohexen-1-yloxy)methyl-5-(3,5-dichlorophenylthio)-4-isopropyl- 1-methyl-1H-imidazole (17)

The compound 14 (166 mg, 0.5 mmol), 1-methoxycyclohexene (280 mg, 2.50 mmol) and p-toluenesulfonic acid pyridinium (132 mg, 0.505 mmol) was dissolved in toluene (4 mL). The reaction mixture was stirred at room temperature for 20 hours. Benzene (60 mL) was added thereto, the reaction mixture was heated under reflux over 45 minutes and concentrated to a small amount. A drop of triethylamine was added to the reaction mixture, and the mixture was filtered to remove the insoluble matter. The filtrate was concentrated under reduced pressure. The residue was extracted with hexane, and filtered off the insoluble matter. The filtrate was purified by chromatography on an alumina column (eluate: toluene) to give the compound 17 (61 mg, 30%) as crystals. Mp 69–71° C. Rf 0.57 ($Al_2O_3$ 60, Type E, toluene).

PMR ($CDCl_3$ -0.1% $d_5$-Py): $\delta$H1.25 (6 H, d, J 7.2 Hz, $(CH_3)_2CH$), 1.50–1.71 (4 H, m, —$CH_2$—), 2.07 (4 H, m, —$CH_2$—), 3.11 (1 H, sep, J 7.2 Hz, $(CH_3)_2CH$), 3.53 (3 H, s, $NCH_3$), 4.80 (1 H, t, J 2.6 Hz, 2-CH), 4.85 (2 H, s, $CH_2O$), 6.80 (2 H, d, J 1.6 Hz arom 2- and 6-H), 7.11 (1 H, t, J 1.6 Hz, arom 4-H). Elementary analysis (for $C_{20}H_{24}N_2OSCl_2$) Calcd.: C, 58.39% H, 5.88% N, 6.81% Cl, 17.24% Found: C, 58.53% H, 5.91% N, 6.92% Cl, 17.09%

EXAMPLE 17

2-(Cycloocten- 1-yloxy)methyl-5-(3,5-dichlorophenylthio)-4-isopropyl- 1 -methyl-1H-imidazole (18)

The compound 14 (33.1 mg, 0.1 mmol) was converted to the enolether with 1-methoxycyclooctene (140 mg, 1 mmol) in the same manner as the example 16 to give the compound 18 (11.0 mg, 22%) as oil. Rf 0.50 ($Al_2O_3$ 60, Type E, toluene).

PMR ($CDCl_3$ -0.1% $d_5$-Py): $\delta$H1.26 (6 H, d, J 6.9 Hz, $(CH_3)_2CH$), 1.42–1.58 (8 H, m, —$CH_2$—), 2.10 (2 H, m, —$CH_2$—), 2.28 (2 H, m, -$CH_2$-), 3.13 (1 H, sep, J 6.9 Hz, $(CH_3)_2CH$), 3.54 (3H, s, $NCH_3$), 4.71 (1 H, t, J 8.1 Hz, =CH), 4.83 (2 H, s, $CH_2O$), 6.83 (2 H, d, J 1.8 Hz, arom 2- and 6-H), 7.13 (1 H, t, 1.8 Hz, arom 4-H). Elementary analysis (for $C_{22}H_{28}N_2OSCl_2$) Calcd.: C, 60.13% H, 6.42% N, 6.37% Cl, 16.14% Found: C, 60.54% H, 6.65% N, 6.19% Cl, 16.23%

EXAMPLE 18

2-(1 -Butoxycyclopentyloxy)methyl-5-(3,5-dichlorophenylthio)-4-isopropyl- 1-ethyl-1H-imidazole (20)

To a solution of 2-hydroxymethyl-5-(3,5-dichlorophenylthio)-4-isopropyl-1-ethyl-1H-imidazole (19) (345 mg, 1 mmol) prepared in accordance with the method as described in WO 96/10019 (EXAMPLE 25) and p-toluenesulfonic acid pyridinium (264 mg, 1.05 mmol) in methylene chloride (5 ml) was added 1,1-dibutoxycyclohexane (2.14 g, 10.0 mmol), and stirred at room temperature for 20 hours. A drop of triethylamine was added to the reaction mixture , and the mixture was filtered to remove the precipitated insoluble matter. The filtrate was concentrated under reduced pressure. Hexane was added to the residue, and the mixture was filtered to remove the insoluble matter. The filtrate was purified by chromatography on an alumina column (eluate: toluene) to give the compound 20 (165 mg, 34%). Rf 0.41 ($Al_2O_3$ 60, Type E, toluene).

PMR ($CDCl_3$ -0.1% $d_5$-Py): $\delta$H0.93 (3 H, t, J 7.5 Hz, $CH_3$), 1.23 (3 H, t, J 7.0 Hz, $CH_3$), 1.24 (6 H, d, J 6.9 Hz, $(CH_3)_2CH$), 1.33–1.82 (12 H, m, cyclopentyl 2-, 3-, 4- and 5-$CH_2$, —$CH_2$—), 3.08 (1 H, sep, J 6.9 Hz, $(CH_3)_2CH$), 3.45 (2 H, t, J 6.9 Hz, $OCH_2$), 4.00 (2 H, q, J 7.0 Hz, $NCH_2$), 4.63 (2 H, s, $CH_2O$), 6.81 (2 H, d, J 1.8 Hz, arom 2- and 6-H), 7.10 (1 H, t, J 1.8 Hz, arom 4-H). Elementary analysis (for $C_{24}H_{34}N_2O_2SCl_2$) Calcd.: C, 59.37% H, 7.06% N, 5.77% Found: C, 59.43% H, 7.15% N, 5.80%

EXAMPLE 19

2-(1-Butoxycyclohexyloxy)methyl-5-(3,5-dichlorophenylthio)-1-ethyl-4-isopropyl-1H-imidazole (21)

The compound 19 (345 mg, 1.00 mmol) was converted to the acetal with 1,1-dibutoxycyclohexane (2.28 g, 10.0 mmol) in the same manner as the example 18 to give the compound 21 (172 mg, 35%) as oil. Rf 0.41 ($Al_2O_3$ 60, Type E, toluene).

PMR ($CDCl_3$ -0.1% $d_5$-Py): $\delta$H0.94 (3 H, t, J 7.5 Hz, $CH_3$), 1.23 (6 H, d, J 6.6 Hz, $(CH_3)_2CH$), 1.25 (3 H, t, J 7.2 Hz, $CH_3$), 1.33–1.75 (14 H, m, —$CH_2$—), 3.08 (1 H, sep, J 6.6 Hz, $(CH_3)_2CH$), 3.42 (2 H, t, J 6.9 Hz, $OCH_2$), 4.03 (2 H, q, 7.2 Hz, $NCH_2$), 4.62 (2 H, s, $CH_2O$), 6.81 (2 H, d, J 1.5 Hz, arom 2- and 6-H), and 7.10 (1 H, t, J 1.5 Hz, arom 4-H). Elementary analysis (for $C_{25}H_{36}N_2O_2SCl_2$) Cacld.: C, 60.11% H, 7.26% N, 5.61% Cl, 14.19% Found: C, 60.34% H, 7.62% N, 5.36% Cl, 14.06%

EXAMPLE 20

5-(3,5-Dichlorophenylthio)-4-isopropyl-2-[2-(2-methoxyadamantan-2-yloxy)ethyl]-1-methyl-1H-imidazole (23)

A solution of 5-(3,5-dichlorophenylthio)-4-isopropyl-2-(2-hydroxyethyl)-1-methyl-1H-imidazole (22) (345 mg, 1 mmol) prepared in accordance with the method as described in WO 96/10019 and p-toluenesulfonic acid mono hydrate (200 mg) in a mixture of tetrahydrofuran (5 mL) - toluene (50 mL) was concentrated under reduced pressure. The residue was dried with a vacuum pump on an oil bath at 50° C. for 40 minutes. The residue was dissolved in toluene (10 mL), and cooled on an ice-bath under nitrogen atmosphere. Then a solution of 2,2-dimethoxyadamantane (1.93 g, 10 mmol) in toluene (1 mL) was added thereto. After stirring at the same temperature for 30 minutes, the reaction mixture was further stirred at room temperature for 4 hours without ice-bath. Triethylamine (0.17 mL, 1.25 mmol) was added to the reaction mixture, and the reaction mixture was concentrated under reduced pressure. Hexane was added to the residue and filtered off the insoluble matter. The hexane-soluble matter was purified by chromatography on an alumina column (eluate: hexane - ethyl acetate (2:1)) to give the compound 23 (227 mg, 44%). Mp 74.5–76° C.

PMR ($CDCl_3$ -0.1% $d_5$-Py): $\delta$H1.22 (6 H, d, J 6.6 Hz, $(CH_3)_2C$), 2.92 (3 H, s, $CH_3O$), 3.02 (2 H, t, J 6.2 Hz, $CH_2$-Im), 3.06 (1 H, m, $(CH_3)_2CH$), 3.52 (3 H, s, $NCH_3$), 3.71 (2 H, t, J 5.8 Hz, $OCH_2$), 6.83 (2 H, d, J 2 Hz, arom-H), 7.11 (1 H, t-like, arom-H) Elementary analysis (for $C_{26}H_{34}N_2O_2Cl_2S$) Calcd.: C, 61.29% H, 6.73% N, 5.50% S, 6.29% Cl, 13.19% Found: C, 61.34% H, 6.75% N, 5.50% S, 6.21% Cl, 13.69%

EXAMPLE 21

5-(3,5-Dichlorophenylthio)-4-isopropyl-2-[2-(2-ethoxyadamantan-2-yloxy)ethyl]-1-methyl-1H-imidazole (24)

The compound 22 (345 mg, 1 mmol) was converted to the acetal with 2,2-diethoxyadamantane (2.28 g, 10 mmol) in the same manner as the example 20 to give the compound 24 (249 mg, 47.5%) as oil.

PMR (CDCl$_3$ -0.1% d$_5$-Py): δH1.09 (3 H, t, J 7 Hz, CH$_3$), 1.23 (6 H, d, J 7 Hz, (CH$_3$)$_2$C), 3.01 (2 H, t, J 5.8 Hz, CH$_2$-Im), 3.11 (2 H, q, J 7 Hz, OCH$_2$), 3.11 (1 H, m, (CH$_3$)$_2$CH), 3.52 (3 H, s, NCH$_3$), 3.71 (2 H, t, J 5.8 Hz, OCH$_2$), 6.84 (2 H, d, J 2 Hz, arom-H), 7.11 (1 H, t-like, arom-H). Elementary analysis (for C$_{27}$H$_{36}$N$_2$O$_2$Cl$_2$S) Calcd.: C, 61.93% H, 6.93% N, 5.35% Found: C, 62.83% H, 7.25% N, 5.17%

EXAMPLE 22

5-(3,5-Dichlorophenylthio)-4-isopropyl-2-[2-(1-methoxycycloheptyloxy)ethyl]-1-methyl-1H-imidazole (25)

The compound 22 (345 mg, 1 mmol) was converted to the acetal with 1,1-dimethoxycycloheptane (1.58 g, 10 mmol) in the same manner as the example 20 to give the compound 25 (158 mg, 33.5%) as oil.

PMR (CDCl$_3$ -0.1% d$_5$-Py): δH1.23 (6 H, d, J 6.6 Hz, (CH$_3$)$_2$C), 2.92 (3 H, s, CH$_3$O), 3.01 (2 H, t, J 5.8 Hz, CH$_2$-Im), 3.10 (1 H, m, (CH$_3$)$_2$CH), 3.52 (3 H, s, NCH$_3$), 3.71 (2 H, t, J 5.8 Hz, OCH$_2$), 6.82 (2 H, d, J 2 Hz, arom-H), 7.11 (t-like, arom-H). Elementary analysis (for C$_{24}$H$_{34}$N$_2$O$_2$Cl$_2$S) Calcd. : C, 59.36% H, 7.06% N, 5.77% Found: C, 59.63% H, 7.13% N, 5.66%

EXAMPLE 23

5-(3,5-Dichlorophenylthio)-4-isopropyl-2-[2-(1-ethoxycycloheptyloxy)ethyl]-1-methyl-1H-imidazole (26)

The compound 22 (345 mg, 1 mmol) was converted to the acetal with 1,1-diethoxycycloheptane (2.03 g, 10 mmol) in the same manner as the example 20 to give the compound 26 (214 mg, 39.8%). Mp 53–54° C.

PMR (CDCl$_3$ -0.1% d$_5$-Py): δH1.07 (3 H, t, J 7 Hz, Et) 1.24 (6 H, d, J 7 Hz, (CH$_3$)$_2$C), 3.00 (2 H, t, J 6 Hz, CH$_2$-Im), 3.12 (2 H, q, J 7 Hz, OCH$_2$CH$_3$), 3.12 (1 H, m, (CH$_3$)$_2$CH), 3.51 (3 H, s, NCH$_3$), 3.71 (2 H, t, J 6 Hz, OCH$_2$), 6.82 (2 H, d, J 1.6 Hz, arom-H), 7.12 (t-like, arom-H). IR(KBr)cm$^{-1}$: 3435, 3056, 1566, 1459, 1405, 1115, 1093, 1066, 1046, 1012 Elementary analysis (for C$_{24}$H$_{34}$N$_2$O$_2$Cl$_2$S) Calcd. : C, 59.37% H, 7.06% N, 5.77% S, 6.60% Cl, 14.60% Found: C, 59.91% H, 7.11% N, 5.97% S, 6.56% Cl, 14.46%

EXAMPLE 24

5-(3,5-Dichlorophenylthio)-4-isopropyl-2-[2-(1-n-propoxycycloheptyloxy)ethyl]-1 -methyl-1H-imidazole (27)

The compound 22 (345 mg, 1 mmol) was converted to the acetal with 1,1-di-n-propoxycycloheptane (2.14 g, 10 mmol) in the same manner as the example 20 to give the compound 27 (188 mg, 39.8%). PMR (CDCl$_3$ -0.1% d$_5$-Py): δH0.87 (3 H, t, J 7.4 Hz, Pr) 1.24 (6 H, d, J 7 Hz, (CH$_3$)$_2$C), 3.00 (2 H, t, J 6 Hz, CH$_2$-Im), 3.05 (2 H, t, J 7 Hz, OCH$_2$CH$_3$), 3.09 (1 H, m, (CH$_3$)$_2$CH), 3.51 (3 H, s, NCH$_3$), 3.71 (2 H, t, J 6 Hz, OCH$_2$), 6.82 (2 H, d, J 1.6 Hz, arom-H), 7.11 (t-like, arom-H). IR(KBr)cm$^{-1}$: 3435, 3063, 1563, 1459, 1119, 1096, 1068, 1015. Elementary analysis (for C$_{25}$H$_{36}$N$_2$O$_2$Cl$_2$S) Cacld.: C, 60.11% H, 7.26% N, 5.61% S, 6.42% Cl, 14.19% Found: C, 60.18% H, 7.30% N, 5.84% S, 6.55% Cl, 13.52%

EXAMPLE 25

5-(3,5-Dichlorophenylthio)-4-isopropyl-2-[2-(1-isobutoxycycloheptyloxy)ethyl]-1-methyl-1H-imidazole (28)

The compound 22 (345 mg, 1 mmol) was converted to the acetal with 1,1-diisobutoxycycloheptane (2.42 g, 10 mmol) in the same manner as the example 20 to give the compound 28 (234 mg, 46%). Rf 0.31 (Al$_2$O$_3$ type E, hexane-EtOAc (10:1)) PMR (CDCl$_3$ -0.1% d$_5$-Py): δH0.87 (6 H, d, J 6.6 Hz, CH$_3$) 1.24 (6 H, d, J 6.6 Hz, (CH$_3$)$_2$C), 1.30–1.75 (13 H, m, —CH$_2$—), 3.00 (2 H, t, J 6.2 Hz, CH$_2$-Im), 3.10 (1 H, sep, J 6.6 Hz, (CH$_3$)$_2$CH), 3.17 (2 H, t, J 6.6 Hz), 3.51 (3 H, s, NCH$_3$), 3.70 (2 H, t, J 6.2 Hz, OCH$_2$), 6.81 (2 H, d, J 1.6 Hz, arom-H), 7.12 (1 H, t, J 1.6 Hz, arom-H) Elementary analysis (for C$_{26}$H$_{38}$N$_2$O$_2$Cl$_2$S) Cacld.: C, 60.81% H, 7.46% N, 5.45% S, 6.24% Cl, 13.81% Found: C, 61.34% H, 7.69% N, 5.33% S, 6.10% Cl, 13.42%

EXAMPLE 26

5-(3,5-Dichlorophenylthio)-4-isopropyl-2-[2-(1-n-butoxycycloheptyloxy)ethyl]-1-methyl-1H-imidazole (29)

The compound 22 (345 mg, 1 mmol) was converted to the acetal with 1,1-di-n-butoxycycloheptane (2.42 g, 10 mmol) in the same manner as the example 20 to give the compound 29 (107 mg, 20.8%). PMR (CDCl$_3$ -0.1% d$_5$-Py): δH 0.90 (3 H, t, J 7.4 Hz, CH$_3$) 1.24 (6H, d, J 7Hz, (CH$_3$)$_2$C), 3.00 (2H, t, J 6Hz, CH$_2$-Im), 3.11 (3 H, m, OCH$_2$CH$_3$, (CH$_3$)$_2$CH), 3.52(3 H, s, NCH$_3$), 3.71 (2 H, t, J 6 Hz, OCH$_2$), 6.83 (2 H, d, J 1.6 Hz, arom-H), 7.12 (t-like, arom-H). Elementary analysis (for C$_{26}$H$_{38}$N$_2$O$_2$Cl$_2$S) Calcd. : C, 60.80% H, 7.46% N, 5.46% Found: C, 60.99% H, 6.56% N, 5.41%

EXAMPLE 27

5-(3,5-Dichlorophenylthio)-4-isopropyl-2-[2-(1-methoxycyclooctyloxy)ethyl]-1-methyl-1H-imidazole (30)

The compound 22 (345 mg, 1 mmol) was converted to the acetal with 1,1-dimethoxycyclooctane (1.62 g, 10 mmol) in the same manner as the example 20 to give the compound 30 (66 mg, 13%). Mp 54–56° C.

PMR (CDCl$_3$ -0.1% d$_5$-Py): δH1.22 (6 H, d, J 7 Hz, (CH$_3$)$_2$C), 2.87 (3 H, s, CH$_3$O), 3.00 (2 H, t, J 6 Hz, CH$_2$-Im), 3.09 (1 H, m, (CH$_3$)$_2$CH), 3.52 (3 H, s, NCH$_3$), 3.68 (2 H, t, J 6 Hz, OCH$_2$), 6.82 (2 H, d, J 2 Hz, arom-H), 7.11 (t-like, arom-H) Elementary analysis (for C$_{24}$H$_{34}$N$_2$O$_2$Cl$_2$S) Calcd.: C, 59.36% H, 7.06% N, 5.77% Found: C, 59.63% H, 7.13% N, 5.66%

EXAMPLE 28

5-(3,5-Dichlorophenylthio)-4-isopropyl-2-[2-(1-ethoxycyclooctyloxy)ethyl]-1-methyl-1H-imidazole (31)

The compound 22 (345 mg, 1 mmol) was converted to the acetal with 1-ethoxycyclooctene (1.61 g, 10 mmol) in the same manner as the example 20 to give the compound 31 (232 mg, 46%). Rf 0.54 (Al$_2$O$_3$ hexane-EtOAc 4:1) PMR (CDCl$_3$ -0.1% d$_5$-Py): δH1.06 (3 H, d, J 7 Hz), 1.37–1.80 (14 H, m), 3.00 (2 H, t, J 6 Hz, CH$_2$-Im), 3.00 (2 H, t, J 6 Hz, CH$_2$-Im), 3.07 (2 H, q, J 7 Hz, OCH$_2$), 3.10 (1 H, s, J 7 Hz, (CH$_3$)$_2$CH), 3.51 (3 H, s, NCH.$_3$), 3.68 (2 H, t, J 6.2 Hz, OCH$_2$), 6.82 (2 H, d, J 1.8 Hz, arom-H), 7.11 (1 H, t-like, arom-H) Elementary analysis (for C$_{25}$H$_{36}$N$_2$O$_2$Cl$_2$S) Calcd. : C, 60.11% H, 7.26% N, 5.61% S, 6.42% Cl, 14.19% Found: C, 59.91% H, 7.36% N, 5.74% S, 6.23% Cl, 13.88%

EXAMPLE 29

5-(3,5-Dichlorophenylthio)-4-isopropyl-2-[2-(1-n-butoxycyclooctyloxy)ethyl]-1-methyl-1H-imidazole (32)

The compound 22 (345 mg, 1 mmol) was converted to the acetal with 1-n-butoxycyclooctene (1.3 g, 5.56 mmol) in the same manner as the example 20 to give the compound 32 (203 mg, 38%). Rf 0.70 (Al$_2$O$_3$ hexane-EtOAc 4:1) PMR (CDCl$_3$-0.1% d$_5$-Py): δH0.88 (3 H, t, J 7.2 Hz, CH$_3$), 1.23 (6 H, d, J 6.9 Hz, (CH$_3$)$_2$CH), 1.25–1.80 (14 H, m, —CH$_2$—), 2.99 (2 H, t, J 5.7 Hz, CH$_2$-Im), 3.05 (2 H, t, J 6.6 Hz, CH$_2$-Im), 3.10 (1 H, s, J 6.9 Hz, (CH$_3$)$_2$CH), 3.51 (3 H, s, NCH$_3$), 3.67 (2 H, t, J 6 Hz, OCH$_2$), 6.82 (2 H, d, J 1.8 Hz, arom-H), 7.12 (1 H, t-like, arom-H) Elementary analysis (for C$_{27}$H$_{40}$N$_2$O$_2$Cl$_2$S) Calcd.: C, 61.47% H, 7.64% N, 5.31% S, 6.08% Cl, 13.44% Found: C, 61.58% H, 7.71% N, 5.36% S, 6.16% Cl, 13.18%

EXAMPLE 30

5-(3,5-Dichlorophenylthio)-4-isopropyl-2-[2- (1-ethoxycyclododecyloxy)ethyl]-1-methyl-1H-imidazole (33)

The compound 22 (345 mg, 1 mmol) was converted to the acetal with 1,1-diethoxycyclododecane (2.56 g, 00 mmol) in the same manner as the example 20 to give the compound 33 (162 mg, 29%).

PMR (CDCl$_3$ -0.1% d$_5$-Py): δH1.08 (3 H, t, J 7.2 Hz, CH$_3$), 1.23 (6 H, d, J 6.9 Hz, (CH$_3$)$_2$CH), 1.20–1.30 (18 H, m, —CH$_2$—), 1.55 (4 H, m, —CH$_2$—), 2.99 (2 H, t, J 5.7 Hz, CH$_2$-Im), 2.99 (2 H, t, J 5.7 Hz, CH$_2$-Im), 3.10 (1 H, s, J 6.9 Hz, (CH$_3$)2CH), 3.12 (2 H, q, J 7.2 Hz, OCH$_2$), 3.51 (3 H, s, NCH$_3$), 3.72 (2 H, t, J 6 Hz, OCH$_2$), 6.82 (2 H, d, J 1.8 Hz, arom-H), 7.11 (t-like, arom-H) Elementary analysis (for C$_{29}$H$_{44}$N$_2$O$_2$Cl$_2$S) Calcd. ; C, 62.69% H, 7.98% N, 5.04% S, 5.77% Cl, 12.76% Found: C, 62.91% H, 8.18% N, 4.91% S, 6.01% Cl, 12.98%

EXAMPLE 31

5-(3,5-Dichlorophenylthio)-4-isopropyl-2-[2-(1-n-butoxycyclohexyloxy)ethyl]-1-methyl-1H-imidazole (34)

The compound 22 (345 mg, 1 mmol) was converted to the acetal with 1,1-di-n-butoxycyclohexane (2.28 g, 00 mmol) in the same manner as the example 20 to give the compound 34 (145 mg, 29%).

PMR (CDCl$_3$ -0.1% d$_5$-Py): δH0.89 (3 H, t, J 7Hz, CH$_3$), 1.23 (6 H, d, J 7Hz, (CH$_3$)$_2$C), 3.2–2.9 (3 H, m, CH2-Im, (CH$_3$)$_2$CH), 3.51 (3 H, s, NCH$_3$), 3.72 (2 H, t, J 6 Hz, OCH$_2$), 6.83 (2 H, d, J 2 Hz, arom-H), 7.11 (t-like, arom-H)

EXAMPLE 32

5-(3,5-Dichlorophenylthio)-4-isopropyl-2-[2-(1-n-butoxycyclopentyloxy)ethyl]-1-methyl-1H-imidazole (35)

The compound 22 (345 mg, 1 mmol) was converted to the acetal with 1,1-di-n-butoxycyclopentane (2.14 g, 10 mmol) in the same manner as the example 20 to give the compound 35 (142 mg, 29.3%).

PMR (CDCl$_3$ -0.1% d$_5$-Py): δH0.89 (3 H, t, J 7 Hz, CH$_3$), 1.24 (6 H. d, J 7 Hz, (CH$_3$)2C), 3.01 (2 H, t, J 6.2 Hz, CH$_2$-Im), 3.10 (1 H, m, (CH$_3$)$_2$CH), 3.21 (2 H, t, J 6.2 Hz, OCH2), 3.50 (3 H, s, NCH$_3$), 3.72 (2 H, t, J 6 Hz, OCH$_2$), 6.83 (2 H, d, J 2 Hz, arom-H), 7.11 (t-like, arom-H). Elementary analysis (for C$_{24}$H$_{34}$N$_2$O$_2$Cl$_2$S) Calcd.: C, 59.37% H, 7.06% N, 5,77% Found: C, 59.49% H, 7.13% N, 5.82%

EXAMPLE 33

5-(3,5-Dichlorophenylthio)-4-isopropyl-2-[2-(1-n-hexyloxycyclopentyloxy)ethyl]-1-methyl-1H-imidazole (36)

The compound 22 (345 mg, 1 mmol) was converted to the acetal with 1,1-di-n-hexoxycyclopentane (2.72 g, 10 mmol) in the same manner as the example 20 to give the compound 36 (178 mg, 34.6%).

PMR (CDCl$_3$ -0.1% d$_5$-Py): δH0.89 (3 H, t-like, CH$_3$), 1.25 (6 H, d, J 7 Hz, (CH$_3$)$_2$C), 3.02 (2 H, t, J 6 Hz, CH$_2$-Im), 3.12 (1 H, m, (CH$_3$)$_2$CH), 3.21 (2 H, t, J 6.2 Hz, OCH$_2$), 3.51 (3 H, s, NCH$_3$), 3.76 (2 H, t, J 6 Hz, OCH$_2$), 6.83 (2 H, d, J 2 Hz, arom-H), 7.12 (t-ike, arom-H) Elementary analysis (for C$_{26}$H$_{38}$N$_2$O$_2$Cl$_2$S) Calcd. : C, 60.80% H, 7.46% N, 5.45% Found: C, 61.32% H, 7.66% N, 5.22%

EXAMPLE 34

5-(3,5-Dichlorophenylthio)-4-isopropyl-2-[2-(endo-2-methoxy- 1,7,7-trimethylbicyclo [2.2. 1]hept-2-yloxy)ethyl]-1-methyl-1H-imidazole (37) and 5-(3, 5-dichlorophenylthio)-4-isopropyl-2-[2-(exo-2-methoxy- 1,7,7-trimethylbicyclo[2.2.1]hept-2-yloxy) ethyl]-1-methyl-1H-imidazole (38)

The compound 22 (345 mg, 1 mmol) was converted to the acetal with 2,2-dimethoxy-1,7,7-trimethylbicyclo[2.2.1] heptane (2.64 g, 10 mmol) in the same manner as the example 20. The product was purified by chromatography on an alumina column (eluate: hexane - ethyl acetate (10:1)) to give the compound 37 (225 mg, 44%) as oil from the early fractions. Further, from the latter fractions the compound 38 (93 mg, 18%) was obtained as oil.

37: PMR (CDCl$_3$ -0.1% d$_5$-Py): δH0.78 (3 H, s, CH$_3$), 0.85 (3 H, s, CH$_3$), 0.91 (3 H, s, CH$_{13}$), 1.22 (3 H, d, J 7 Hz, (CH$_3$)$_2$C), 1.24 (3 H, d, J 7 Hz, (CH$_3$)$_2$C), 2.90 (3 H, s, CH$_3$O), 2.95 (2 H, m, CH$_2$-Im), 3.09 (1 H, m, (CH$_3$)$_2$CH), 3.52 (3 H, s, NCH$_3$), 3.8 (2 H, m, OCH$_2$), 6.82 (2 H, d, J 2 Hz, arom-H), 7.11 (1 H, t-like, arom-H). Elementary analysis (for C$_{26}$H$_{36}$N$_2$O$_2$Cl$_2$S) Calcd. : C, 61.04% H, 7.09% N, 5.47% Found: C, 61.61% H, 7.33% N, 5.47%

38: PMR (CDCl$_3$ -0.1% d$_5$-Py): δH0.66 (3 H, CH$_3$), 0.76 (3 H, 8, CH$_3$), 0.84 (3 H, s, CH$_3$), 1.22 (6 H, d, J 7 Hz, (CH$_3$)$_2$C), 3.06 (3 H, s, CH$_3$O), 3.06 (2 H, m, CH$_2$-Im), 3.06 (1 H, m, (CH$_3$)$_2$CH), 3.52 (3 H, s, NCH$_3$), 3.65 (2 H, m, OCH$_2$), 6.83 (2 H, d, J 2 Hz, arom-H), 7.11 (1 H, t-like, arom-H). Elementary analysis (for C$_{26}$H$_{36}$N$_2$O$_2$Cl$_2$S) Calcd.: C, 61.04% H, 7.09% N, 5.47% Found: C, 61.22% H, 7.21% N, 5.47%

EXAMPLE 35

5-(3,5-Dichlorophenylthio)-4-isopropyl-2-[2-(endo-2-ethoxy- 1,7,7-trimethylbicyclo[2.2.1]hept-2-yloxy) ethyl]-1-methyl-1H-imidazole (39) and 5 -(3,5-dichlorophenylthio)-4-isopropyl-2-[2-(exo-2-ethoxy-1, 7,7-trimethylbicyclo[2.2.1]hept-2-yloxy)ethyl]-1-methyl-1H-imidazole (40)

The compound 22 (345 mg, 1 mmol) was converted to the acetal with 1,1-diethoxy-1,7,7-trimethylbicyclo[2.2.1] heptane (4.5 g, 10 mmol) in the same manner as the example 20. The product was purified by chromatography on an alumina column (eluate: hexane - ethyl acetate (15:1)) to give the compound 39 (150 mg, 28.5%) as oil from the early fractions. Further, from the latter fractions the compound 40 (132 mg, 25.1%) was obtained as oil. 39: PMR (CDCl$_3$ -0.1% d$_5$-Py): δH0.93 (3 H, s, CH$_3$), 0.88 (3 H, s, CH$_3$),0.79 (3 H, s, CH$_3$), 1.08 (3 H, t, J 7.2 Hz, Et) 1.24 (3 H, d, J 6.6 Hz, (CH$_3$)$_2$C), 1.25 (3 H, d, J 6.6 Hz, (CH$_3$)$_2$C), 2.90 (3 H, m, CH$_2$-IM, (CH$_3$)$_2$CH), 3.20 (2 H, m, OCH$_2$), 3.53 (3 H, s, NCH$_3$), 3.80 (2 H, m, OCH$_2$), 6.93 (2 H, d, J 2 Hz, arom-H), 7.12 (t-like, arom-H). Elementary analysis (for C$_{27}$H$_{38}$N$_2$O$_2$Cl$_2$S) Calcd. : C, 61.70% H, 7.29% N, 5.33% Found: C, 62.00% H, 7.52% N, 5.33%

40: PMR (CDCl₃-0.1% d₅-Py): δH0.81 (3 H, s, CH₃), 0.76 (3 H. 8, CH₃),0.67 (3 H, s, CH₃), 1.08 (3 H, t, J 7 Hz, Et) 1.23 (3 H, d, J 6.6 Hz, (CH₃)₂C), 1.24 (3 H, d, J 6.6 Hz, (CH₃)₂C), 3.00 (2 H, t, J 4.2 Hz, CH₂-Im), 3.10 (1 H, m, (CH₃)₂CH), 3.51 (3 H, s, NCH₃), 3.75 (2 H, m, OCH₂), 6.83 (2 H, d, J 2 Hz, arom-H), 7.11 (t-like, arom-H). Elementary analysis (for C₂₇H₃₈N₂O₂Cl₂S) Cacld. : C, 61.70% H, 7.29% N, 5.33% Found: C, 61.72% H, 7.38% N, 5.32%

EXAMPLE 36

5-(3,5-Dichlorophenylthio)-4-isopropyl-2-[2-(endo-2-ethoxybicyclo [2.2.1]hept-2-yloxy)ethyl]-1-methyl-1H-imidazole (41)

The compound 22 (345 mg, 1 mmol) was converted to the acetal with 2,2-diethoxybicyclo[2.2.1]heptane (1.84 g, 10 mmol) in the same manner as the example 20 to give the compound 41 (160 mg, 33.1%) as oil.

PMR (CDCl₃ -0.1% d₅-Py): δH0.90 (3 H, t, J 7 Hz, Et) 1.24 (6 H, d, J 7 Hz, (CH₃)₂C), 3.00 (2 H, t, J 6 Hz, CH₂-Im), 3.11 (2 H, m, OCH₂), 3.11 (1 H, m, (CH₃)₂CH), 3.52 (3 H, s, NCH₃), 3.71 (2 H, t, J 6 HZ, OCH₂), 6.83 (2 H, m, arom-H), 7.12 (1 H, t-like, arom-H). Elementary analysis (for C₂₄H₃₂N₂O₂Cl₂S) Cacld.: C, 59.61% H, 6.67% N, 5.79% Found: C, 59.87% H, 6.71% N, 5.83%

EXAMPLE 37

5-(3,5-Dichlorophenylthio)-4-isopropyl-2-[2-(methoxydiphenylmethoxy)ethyl]-1-methyl-1H-imidazole (42)

The compound 22 (345 mg, 1 mmol) was converted to the acetal with 1,1-dimethoxybenzophenone (2.28 g, 10 mmol) in the same manner as the example 20 to give the compound 42 (136 mg, 25.1%). Mp 107–108.5° C. PMR (CDCl₃ -0.1% d₅-Py): δH1.25 (6 H, d, J 4.8 Hz, (CH₃)₂C), 2.97 (3 H, s, CH₃O), 3.09 (3 H, m, CH₂-Im, (CH₃)₂CH), 3.47 (3 H, s, NCH₃), 3.60 (2 H, t, J 4.4 Hz, OCH₂), 6.79 (2 H, m, arom-H), 7.09 (1 H, t-like, arom-H), 7.5-7.1 (10 H, m, Ph). Elementary analysis (for C₂₉H₃₀N₂O₂Cl₂S) Calcd.: C, 64.32% H, 5.58% N, 5.17% Found: C, 64.40% H, 5.60% N, 5.24%

EXAMPLE 38

5-(3,5-Dichlorophenylthio)-4-isopropyl-2-[2-(9-methoxy-9H-fluoren-9-yloxy)ethyl]-1-methyl-1H-imidazole (43)

The compound 22 (345 mg, 1 mmol) was converted to the acetal with 9,9-dimethoxyfluorene (2.26 g, 10 mmol) in the same manner as the example 20 to give the compound 43 (114 mg, 21.2%). Mp 130–131° C. PMR (CDCl₃ -0.1% d₅-Py): δH1.24 (6 H, d, J 7 Hz, (CH₃)₂C), 3.20 (3 H, s, CH₃O), 3.02 (2 H, m, CH₂-Im), 3.11 (1 H, m, (CH₃)₂CH), 3.42 (3 H, s, NCH₃), 3.85 (2 H, t, J 6.2 Hz, OCH₂), 6.8–7.6 (8 H, m, arom-H) Elementary analysis (for C₂₉H₂₈N₂O₂Cl₂S) Calcd.: C, 64.56% H, 5.23% N, 5.19% S, 5.94% Cl, 13.14% Found: C, 64.65% H, 5.25% N, 5.10% S, 5.95% Cl, 12.89%

EXAMPLE 39

5-(3,5-Dichlorophenylthio)-4-isopropyl-2-[2-(1-methoxy-1-methylethoxy)ethyl]- 1-methyl-1H-imidazole (44) and 2,2-bis- [5-(3, 5-dichlorophenylthio)-4-isopropyl-1-methyl-1H-imidazol-2-ylethoxy]propane (45)

The compound 22 (345 mg, 1 mmol) was converted to the acetal with 2,2-dimethoxypropane (1.05 g, 10 mmol) in the same manner as the example 20. The product was purified by chromatography on an alumina column (eluate: hexane - ethyl acetate (4:1)) to give the compound 44 (27 mg, 7%) from the early fractions. Further, from the latter fractions the compound 45 (143 mg, 39%) was obtained. 44: mp 74–76° C. PMR (CDCl₃ -0.1% d₅-Py): δH1.23 (6 H, d, J 7 Hz, (CH₃)₂C), 1.27 (6 H, s, CH₃), 2.97 (3 H, s, CH₃O), 3.01 (2 H, t, J 6.2 Hz, CH₂-Im), 3.10 (1 H, sep, (CH₃)₂CH), 3.51 (3 H, s, NCH₃), 3.75 (2 H, t, J 6.2 Hz, OCH₂), 6.81 (2 H, d, arom-H), 7.01 (1 H, t, J 1.8 Hz, arom-H) Elementary analysis (for C₁₉H₂₆N₂O₂Cl₂S) Calcd.: C, 54.67% H, 6.28% N, 6.71% S, 7.68% Cl, 16.99% Found: C, 54.74% H, 6.34% N, 6.73% S, 7.52% Cl, 16.71% 45: mp 85–87° C. PMR (CDCl₃-0.1% d₅-Py): δH1.19 (6 H, s, CH₃), 1.22 (12 H, d, J 7Hz) 2.93 (4 H, t, J 6.2 Hz, CH₂-Im), 3.09 (2 H, sep, J 7 Hz, (CH₃)₂CH), 3.47 (6 H, s, NCH₃), 3.60 (4 H, t, J 5.8 Hz, OCH₂), 6.78 (4 H, d, J 1.6 Hz, arom-H), 7.10 (2 H, t, J 1.6 Hz, arom-H) Elementary analysis (for C₃₃H₄₀N₄O₄Cl₄S₂) Calcd. : C, 54.25% H, 5.52% N, 7.67% S, 8.78% Cl, 19.41% Found: C, 54.44% H, 5.66% N, 7.65% S, 8.73% Cl, 19.12%

EXAMPLE 40

1,1-Bis-2-{[5-(3,5-dichlorophenylthio)-4-isopropyl-1-methyl-1H-imidazol-2-yl]ethoxy}cycloheptane (46)

The compound 22 (345 mg, 1 mmol) was converted to the acetal with 2,2-dimethoxycycloheptane (2.42 g, 10 mmol) in the same manner as the example 20 to give the compound 46 (10 mg, 3%). Mp 130–133° C. Rf 0.43 (Al₂O₃, hexane-EtOAc 4:1) PMR (CDCl₃-0.1% d₅-Py): δH1.22 (12 H, d, J 6.9 Hz), 1.30 (4 H, m), 1.41 (4 H, m), 1.65 (4 H, m), 2.93 (4 H, t, J 6.3 Hz), 3.09 (2 H, sep, J 7.2 Hz), 3.48 (6 H, s), 3.54 (4 H, d, J 6 Hz), 6.80 (2 H, d, J 1.8 Hz), 7.10 (2 H, d, J 1.8 Hz) Elementary analysis (for C₃₇H₄₆N₄O₂Cl4S₂) Calcd.: C, 56.63% H, 5.91% N, 7.14% S, 8.17% Cl, 18.07% Found: C, 56.91% H, 5.98% N, 7.10% S, 8.05% Cl, 17.81%

EXAMPLE 41

2-[2-(Cycloocten-1-yloxy)ethyl]-5-(3,5-dichlorophenylthio)-4-isopropyl-1-methyl-1H-imidazole (47)

A solution of the compound 22 (690 mg, 2 mmol) and p-toluenesulfonic acid hydrate (400 mg, 2.1 mmol) in a mixture of tetrahydrofuran (10 mL) - toluene (100 ML) was concentrated under reduced pressure. The residue was dried on an oil bath at 55° C. for 40 minutes. The residue was dissolved in toluene (100 mL), and 1-methoxycyclooctene (1.84 g, 10 mmol) was added thereto. The reaction mixture was heated with reflux over 1 hours and concentrated to a small quantity. After cooling down at room temperature, triethylamine (0.4 mL) was added thereto. The reaction mixture was purified by chromatography on an alumina column (eluate: hexane - ethyl acetate (15:1)) to give the compound 47 (790 mg, 87%). Mp 73–74° C. PMR (CDCl₃-0.1% d₅-Py): δH1.24 (6 H, d, J 4.6 Hz, (CH₃)₂C), 3.13 (2 H, t, J 4.2 Hz, CH₂-Im), 3.08 (1 H, m, (CH₃)₂CH), 3.51 (3 H, s, NCH₃), 3.96 (2 H, t, J 4.2 Hz, OCH₂), 4.51(1 H, t, J 5.6 Hz, =CH), 6.77 (2 H, d, J 2 Hz, arom-H), 7.09 (1 H, t-like, arom-H). IR(KBr)cm⁻¹: 3436, 3056, 1659, 1568, 1533, 1500, 1160, 1094. Elementary analysis (for C₂₃H₃₀N₂Ocl₂S) Calcd. : C, 60.91% H, 6.67% N, 6.18% S, 7.07% Cl, 15.63% Found: C, 60.74% H, 6.69% N, 5.94% S, 6.83% Cl, 15.43%

EXAMPLE 42

2-[2-(Cyclodecen-1-yloxyl)ethyl]-5-(3,5-dichlorophenylthio)-4-isopropyl-1-methyl-1H-imidazole (48)

The compound 22 (345 mg, 1 mmol) was converted to the enol ether with 1-methoxycyclodecene (841 mg, 5 mmol) in the same manner as the example 41 to give the compound 48 (432 mg, 89%). Mp 94–96° C. PMR (CDCl$_3$-0.1% d$_5$-Py): δH1.24 (6 H, d, J 6.6 Hz, (CH$_3$)$_2$C), 3.13 (2 H, t, J 6.2 Hz, CH$_2$-Im), 3.10 (1 H, m, (CH$_3$)$_2$CH), 3.52 (3 H, s, NCH$_3$), 4.01 (2 H, t, J 6.2 Hz, OCH$_2$), 4.38(1 H, t, J 8.4 Hz, =CH), 6.80 (2 H, d, J 1.6 Hz, arom-H), 7.10 (1 H, t-like, arom-H). IR(KBr)cm$^{-1}$: 3436, 3035, 1660, 1567, 1558, 1471, 1408, 1376, 1237, 1104. Elementary analysis (for C$_{25}$H$_{34}$N$_2$Ocl$_2$S) Calcd. : C, 62.36% H, 7.12% N, 5.82% S, 6.66% Cl, 14.73% Found: C, 62.54% H, 7.18% N, 5.69% S, 6.60% Cl, 14.52%

EXAMPLE 43

2-[2-(Cyclododecen-1-yloxyl)ethyl]-5-(3,5-dichlorophenylthio)-4-isopropyl-1-methyl-1H-imidazole (49)

The compound 22 (345 mg, 1 mmol) was converted to the enol ether with 1-methoxycyclododecene (982 mg, 5 mmol) in the same manner as the example 41 to give the compound 49 (418 mg, 82%). Mp 96–102° C. PMR (CDCl$_3$-0.1% d$_5$-Py): δH1.24 (6 H, d, J 7 Hz, (CH$_3$)$_2$C), 3.11 (2 H, t, J 6.2 Hz, CH$_2$-Im), 3.10 (1 H, m, (CH$_3$)$_2$CH), 3.51 (3 H, s, NCH$_3$), 3.96 (2 H, t, J 6.2 Hz, OCH$_2$), 4.36 (1 H, t, J 7.8 Hz, =CH), 6.80 (2 H, d, J 1.6 Hz, arom-H), 7.10 (1 H, t-like, arom-H). IR(KBr)cm$^{-1}$: 3434, 3057, 1702, 1662, 1566, 1558, 1469, 1409, 1378, 1235, 1130. Elementary analysis (for C$_{27}$H$_{38}$N$_2$Ocl$_2$S) Calcd. : C, 63.64% H, 7.52% N, 5.50% S, 6.29% Cl, 13.91% Found: C, 64.48% H, 7.69% N, 5.10% S, 6.03% Cl, 12.85%

EXAMPLE 44

2-[2-(4-tert-Butylcyclohexen-1-yloxyl)ethyl]-5-(3,5-dichlorophenylthio)-4-isopropyl-1-methyl-1H-imidazole (50)

The compound 22 (345 mg, 1 mmol) was converted to the enol ether with 4-tert-butyl-1,1-dimethoxycyclohexane (1 g, 5 mmol) in the same manner as the example 41 to give the compound 50 (337 mg, 70%). Mp 99.5–100.5° C. PMR (CDCl$_3$ -0.1% d$_5$-Py): δH0.86 (9 H, s, t-Bu), 1.24 (6 H, d, J 4.4 Hz, (CH$_3$)$_2$C), 3.12 (2 H, t, J 4.2 Hz, CH$_2$-Im), 3.12 (1 H, m, (CH$_3$)$_2$CH), 3.50 (3 H, s, NCH$_3$), 3.97 (2 H, m, OCH$_2$), 4.61 (1 H, m, =CH), 6.77 (2 H, d, J 1 Hz, arom-H), 7.09 (1 H, t-like, arom-H). Elementary analysis (for C$_{25}$H$_{34}$N$_2$Ocl$_2$S) Calcd. : C, 62.35% H, 7.12% N, 5.82% S, 6.66% Cl, 14.72% Found: C, 62.56% H, 7.13% N, 5.76% S, 6.57% Cl, 14.43%

EXAMPLE 45

5-(3,5-Dichlorophenylthio)-4-isopropyl-2-[2-(3,4-dihydronaphthalen-1-yloxy)ethyl]-1-methyl-1H-imidazole (51)

The compound 22 (345 mg, 1 mmol) was converted to the enol ether with 1-methoxy-3,4-dihydronaphthalene (801 mg, 10 mmol) in the same manner as the example 41 to give the compound 51 (226 mg, 47.8%). Mp 99–102° C. PMR (CDCl$_3$-0.1% d$_5$-Py): δH1.26 (6 H, d, J 7 Hz, (CH$_3$)$_2$C), 2.73 (2 H, t, J 7.8 Hz, =-CH$_2$), 3.27 (2 H, t, J 6.2 Hz, CH$_2$-Im), 3.11 (1 H, m, (CH$_3$)$_2$CH), 3.54 (3 H, s, NCH$_3$), 4.22 (2 H, t, J 6.2 Hz, OCH$_2$), 5.04 (1 H, t, J 6.4 Hz, =CH), 6.79 (2 H, d, J 1.6 Hz, arom-H), 7.4-7.0 (5 H, m, arom-H) IR(KBr)cm$^{-1}$: 3434, 3060, 1636, 1566, 1252, 1099. Elementary analysis (for C$_{25}$H$_{26}$N$_2$Ocl$_2$S) Calcd. : C, 63.42% H, 5.53% N, 5.92% S, 6.77% Cl, 14.98% Found: C, 64.13% H, 5.74% N, 5.74% S, 6.62% Cl, 14.11%

EXAMPLE 46

5-(3,5-Dichlorophenylthio)-4-isopropyl-2-[2-(8,9-dihydro-7H-benzocyclohepten-5-yloxy)ethyl]-1-methyl-1H-imidazole (52)

The compound 22 (345 mg, 1 mmol) was converted to the enol ether with 5-methoxy-8,9-dihydro-7H-benzocyclohept-5-ene (1.25 g, 6 mmol) in the same manner as the example 41 to give the compound 52 (428 mg, 87.9%). PMR (CDCl$_3$ -0.1% d$_5$-Py): δH1.26 (6 H, d, J 7 Hz, (CH$_3$)$_2$C), 3.22 (2 H, t, J 6.4 Hz, CH$_2$-Im), 3.12 (1 H, m, (CH$_3$)$_2$CH), 3.48 (3 H, s, NCH$_3$), 4.18 (2 H, t, J 6.4 Hz, OCH$_2$), 5.18 (1 H, t, J 7 Hz, =CH), 6.81 (2 H, d, J 1.6 Hz, arom-H), 7.3-7.1 (5 H, m, arom-H) Elementary analysis (for C$_{26}$H$_{28}$N$_2$Ocl$_2$S) Calcd. : C, 64.05% H, 5.79% N, 5.75% Found: C, 64.51% H, 6.08% N, 5.78%

EXAMPLE 47

5-(3,5-Dichlorophenylthio)-4-isopropyl-2-[2-(1-adamantan-1-ylvinyloxy)ethyl]-1-methyl-1H-imidazole (53)

The compound 22 (690 mg, 2 mmol) was converted to the enol ether with 1-adamantylmethylketon dimethyl acetal (2.93 g, 13 mmol) in the same manner as the example 41 to give the compound 53 (724 mg, 71.7%). Mp 114.5–115.5° C. PMR (CDCl$_3$ -0.1% d$_5$-Py): δH1.24 (6 H, d, J 7 Hz, (CH$_3$)$_2$C), 3.15 (2 H, t, J 6.2 Hz, CH$_2$-Im), 3.11 (1 H, m, (CH$_3$)$_2$CH), 3.55 (3 H, s, NCH$_3$), 3.97 (2 H, t, J 6.2 Hz, OCH$_2$), 3.86 (1 H, d, J 2.4 Hz, =CH$_2$), 3.80 (1 H, d, J 2.4 Hz,=CH$_2$) 6.80 (2 H, d, J 1.6 Hz, arom-H), 7.10 (1 H, t-like, arom-H). Elementary analysis (for C$_{27}$H$_{34}$N$_2$Ocl$_2$S) Calcd. : C, 64.14% H, 6.78% N, 5.54% S, 6.34% Cl, 14.02% Found: C, 64.04% H, 6.82% N, 5.46% S, 6.31% Cl, 13.87%

EXAMPLE 48

5-(3,5-Dichlorophenylthio)-4-isopropyl-2-[2-(1-ethoxycyclooctyloxy)ethyl]-1-ethyl-1H-imidazole (55)

5-(3,5-Dichlorophenylthio)-4-isopropyl-2-(hydroxy) ethyl]-1-ethyl- 1H-imidazole (54) (359 mg, 1 mmol) prepared in accordance with the method as described in WO 96/10019 was converted to the acetal with 1,1-diethoxycyclooctane (1.61 g, 10 mmol) in the same manner as the example 20 to give the compound 55 (252 mg, 49%). Rf 0.59 (Al$_2$O$_3$ hexane-EtOAc 4:1) PMR (CDCl$_3$-0.1% d$_5$-Py): δH1.09 (3 H, d, J 7 Hz), 1.19 (3 H, t, J 7.2 Hz)1.23 (6 H, d, J 6.6 Hz), 1.38–1.75 (14 H, m), 2.97 (2 H, t, J 6 Hz, CH$_2$-Im), 3.08 (1 H, sep, J 6.6 Hz, (CH$_3$)$_2$CH), 3.13 (2 H, q, J 6.9 Hz), 3.72 (2 H, t, J 6.2 Hz, OCH$_2$), 4.00 (2 H, q, J 7.2 Hz), 6.83 (2 H, d, J 1.8 Hz, arom-H), 7.11 (1 H, t-like, arom-H) Elementary analysis (for C$_{26}$H$_{38}$N$_2$O$_2$Cl$_2$S) Calcd.: C, 60.81% H, 7.46% N, 5.45% S, 6.24% Cl, 13.81% Found: C, 60.70% H, 7.55% N, 5.44% S, 6.23% Cl, 13.42%

EXAMPLE 49

5-(3,5-Dichlorophenylthio)-4-isopropyl-2-[2-(1-n-butoxycyclooctyloxy)ethyl]-1-ethyl-1H-imidazole (56)

The compound 54 (359 mg, 1 mmol) was converted to the acetal with 1,1-di-n-butoxycyclooctane (1.61 g, 10 mmol) in the same manner as the example 20 to give the compound 56 (367 mg, 41%). Rf 0.54 (Al$_2$O$_3$ hexane-EtOAc 8:1) PMR (CDCl$_3$-0.1% d$_5$-Py): δH0.89 (3 H, t, J 7.5 Hz), 1.18 (3 H, t, J 7.5 Hz), 1.23 (6 H, d, J 6.9 Hz), 1.25–1.75 (18 H, m), 2.97 (2 H, t, J 6.3 Hz), 3.08 (1 H, sep, J 6.6 Hz, $(CH_3)_2CH$), 3.12 (2 H, t, J 6.2 Hz), 3.71 (2 H, t, J 6.2 Hz, $OCH_2$), 3.99 (2 H, q, J 7.5 Hz), 6.83 (2 H, d, J 1.8 Hz, arom-H), 7.10 (1 H, t-like, arom-H) Elementary analysis (for $C_{28}H_{42}N_2O_2Cl_2S$) Calcd. : C, 62.09% H, 7.82% N, 5.17% S, 5.92% Cl, 13.09% Found: C, 62.12% H, 7.91% N, 5.20% S, 5.89% Cl, 13.01%

EXAMPLE 50

5-(3,5-Dichlorophenylthio)-4-isopropyl-2-[2-(1-methyl- 1-n-octyloxyethoxy)ethyl]-1-methyl-1H-imidazole (57)

The compound 54 (345 mg, 1 mmol) was converted to the acetal with 2,2-di-n-octoxypropane (1.89 g, 6.3 mmol) in the same manner as the example 20 to give the compound 57 (190 mg, 51%). Rf 0.55 ($Al_2O_3$ hexane-EtOAc 6:1) PMR ($CDCl_3$ -0.1% $d_5$-Py): δH0.88 (3 H, m, $CH_3$), 1.18 (3 H, t, J 7.2 Hz, $CH_3$), 1.23 (6 H, d, J 6.9 Hz, $(CH_3)_2CH$), 1.28 (6 H, s, $CH_3$), 1.20–1.30 (10 H, m), 1.46 (2 H, m), 2.98 (2 H, t, J 6.6 Hz, $CH_2$-Im), 3.08 (1 H, sep, $(CH_3)_2CH$), 3.21 (2 H, t, J 6.6 Hz), 3.78 (2 H, t, J 6.2 Hz, $OCH_2$), 3.97 (2 H, q, J 7.2 Hz), 6.81 (2 H, d, J 1.8 Hz, arom-H), 7.01 (1 H, t, J 1.8 Hz, arom-H) Elementary analysis (for $C_{27}H_{42}N_2O_2Cl_2S$) Calcd. : C, 61.23% H, 7.99% N, 5.29% S, 6.05% Cl, 13.39% Found: C, 60.98% H, 7.98% N, 5.35% S, 6.10% Cl, 13.25%

EXAMPLE 51

5- (3,5-Dichlorophenylthio)-4-isopropyl-2-[2-(1-methoxy-1-methyl-n-heptoxy)ethyl]-1-methyl-1H-imidazole (58)

The compound 54 (345 mg, 1 mmol) was converted to the acetal with 2,2-dimethoxyoctane (1.1 g, 6.3 mmol) in the same manner as the example 20 to give the compound 58 (98 mg, 24%). Rf 0.75 ($Al_2O_3$ hexane-EtOAc 4:1) PMR ($CDCl_3$-0.1% $d_5$-Py): δH0.88 (3 H, m, $CH_3$), 1.15–1.30 (20 H, m), 1.52 (2 H, m), 2.97 (3 H, s, $CH_3O$), 2.99 (2 H, t, J 6.2 Hz, $CH_2$-Im), 3.08 (1 H, sep, $(CH_3)_2CH$), 3.76 (2 H, m, $OCH_2$), 3.98 (2 H, q, J 7 Hz), 6.81 (2 H, d, J 2 Hz, arom-H), 7.01 (1 H, t, J 2 Hz, arom-H) Elementary analysis (for $C_{25}H_{38}N_2O_2Cl_2S$) Calcd.: C, 59.87% H, 7.64% N, 5.59% S, 6.39% Cl, 14.14% Found: C, 59.79% H, 7.66% N, 5.65% S, 6.29% Cl, 13.87%

EXAMPLE 52

2[2-(2-(Cycloocten-1-yloxy)ethyl]-5-(3,5-dichlorophenylthio)-4-isopropyl-1-ethyl-1H-imidazole (59)

The compound 54 (359 mg, 1 mmol) was converted to the enol ether with 1-methoxycyclooctene (0.7 g, 5 mmol) in the same manner as the example 41 to give the compound 59 (365 mg, 78%). Rf 0.36 ($Al_2O_3$ toluene) PMR ($CDCl_3$-0.1% $d_5$-Py): δH1.19 (3 H, t, J 7.5 Hz), 1.23 (6 H, d, J 6.9 Hz), 1.46 (8 H, m), 2.05 (2 H, m), 2.17 (2 H, m), 3.08 (1 H, sep, J 6.9 Hz, $(CH_3)_2CH$), 3.11 (2 H, t, J 6.6 Hz), 3.97 (2 H, q, J 7.5 Hz), 4.00 (2 H, t, J 6.6Hz), 4.53 (1 H, t, J 7.1 Hz), 6.80 (2 H, d, J 1.5 Hz, arom-H), 7.09 (1 H, t, J 1.5 Hz, arom-H) Elementary analysis (for $C_{24}H_{32}N_2Ocl_2S$) Calcd. : C, 61.60% H, 6.90% N, 5.99% S, 6.86% Cl, 15.17% Found: C, 61.89% H, 7.04% N, 6.08% S, 6.85% Cl, 15.13%

EXAMPLE 53

Mono-{2-[5-(3,5-dimethylphenylthio)-4-isopropyl-2-methyl-imidazol-1-yl]methoxyethyl}succinate (68)

To a solution of the compound 1 (334 mg, 1.00 mmol) and succinic anhydride (100 mg, 1.00 mmol) in methylene chloride (5 mL) was added N,N-dimethylaminopyridine (122 mg, 1.00 mmol) under ice-cooling, and stirred at room temperature for 2 hours. The reaction mixture was distributed between methylene chloride (30 mL) and 0.01N hydrochloric acid (30 mL). The organic later was separated and washed with water. The organic layer was dried over sodium sulfate, and concentrated under reduced pressure. The residue was purified by chromatography on a silica gel column (eluate: chloroform - methanol (9:1)) to give the compound 68 (295 mg, 68%) as crystals. Mp 133–135° C. (ether-hexane) Rf 0.26 (10:1 $CHCl_3$—$CH_3OH$).

PMR ($CDCl_3$): δH1.26 (6 H, d, 6.8 Hz, $(CH_3)_2CH$), 2.22 (6 H, s, arom 3- and 5-$CH_3$), 2.55 (3 H, s, 2-$CH_3$), 2.60 (4 H, bs, $COCH_2CH_2CO$), 3.18 (1 H, sep, 6.8 Hz, $(CH_3)_2CH$), 3.49 (2 H, m, $OCH_2CH_2OCO$), 4.08 (2 H, m, $OCH_2CH_2OCO$), 5.28 (2 H, s, $NCH_2O$), 6.59 (2 H, s, arom 2- and 6-H), and 6.76 (1 H, s, arom 4-H). LSIMS: m/z 435 (M+H)+. Elementary analysis (for $C_{22}H_{30}N_2O_5S$) Calcd.: C, 60.81% H, 6.96% N, 6.45% Found: C, 60.29% H, 6.83% N, 6.40%

EXAMPLE 54 (1)

Mono-[2-(trimethylsilanyl)ethyl] sebacate (60)

To a suspension of sebacic acid (2.06 g, 10 mmol), 2-(trimethylsilyl)ethanol (1.18 g, 10.0 mmol) and N,N-dimethylaminopyridine (122 mg, 1.00 mmol) in methylene chloride (50 mL) - acetonitrile (50 mL) was added 1,3-dicyclohexylcarbodiimide (2.26 g, 11 mmol), and stirred at room temperature for 16 hours. The resulting precipitate was filtered off. The filtrate was concentrated under reduced pressure. The residue was extracted with hexane (100 mL), filtered off to remove insoluble matter, and concentrated under reduced pressure. The residue was purified by chromatography on a silica gel column (eluate: hexane - ethyl acetate (2:1)), recrystallized with hexane to give the compound 60 (1.15 g, 50%) as crystals. Mp 34–35° C. Rf 0.49 (2:1 hexane-EtOAc).

PMR ($CDCl_3$): δH0.04 (9 H, s, $(CH_3)_3Si$),0.98 (2 H, m, $CH_2Si$), 1.29 (8 H, bs, —$CH_2$—), 1.62 (4 H, bm, —$CH_2$—), 2.28 and 2.36 (each 2 H, t, 7.2 Hz, —$CH_2CO$—), and 4.15 (2 H, m, $CH_2O$). Elementary analysis (for $C_{15}H_{30}O_4Si$) Calcd. : C, 59.56% H, 10.0% Found: C, 59.64% H, 9.88%

(2) 2 -[5-(3,5-Dimethylphenylthio)-4-isopropyl-2-methyl-imidazol- 1-ylmethoxy]ethyl 2-(trimethylsilanyl)ethyl sebacate (64)

To a solution of the compound 1 (334 mg, 1 mmol), 60 (303 mg, 1.00 mmol) and N,N-dimethylaminopyridine (122 mg, 1 mmol) in methylene chloride (5 mL) was added 1,3-dicyclohexylcarbodiimide (206 mg, 1.08 mmol) under ice-cooling. The reaction mixture was stirred at room temperature for 18 hours. The precipitated insoluble matter was filtered off, and the filtrate was concentrated under reduced pressure. The residue was purified by chromatography on a silica gel column (eluate: hexane - ethyl acetate (1:1)) to give the compound 64 (580 mg, 94%) as oil. Rf 0.27 (1:1 EtOAc-hexane).

PMR ($CDCl_3$): δH0.04 (9 H, s, $(CH_3)_3Si$),0.98 (2 H, m, $SiCH_2$), 1.26 (6 H, d, 7.0 Hz, $(CH_3)_2CH$), 1.27 (8 H, bs, —$CH_2$—), 1.59 (4 H, bm, —$CH_2$—), 2.22 (6 H, s, arom 3- and 5-$CH_3$), 2.27 (4 H, t, 7.2 Hz, —$CH_2CO$—), 2.53 (3 H, s, 2-$CH_3$), 3.16 (1 H, sep, 7.0 Hz, $(CH_3)_2CH$), 3.48 (2 H, m, $OCH_2CH_2OCO$), 4.04 (2 H, m, $OCH_2CH_2OCO$), 4.16 (2 H, m, $OCH_2$), 5.27 (2 H, s, $NCH_2O$), 6.59 (2 H, 8, arom 2- and 6-H), and 6.75 (1 H, s, arom 4-H). Elementary analysis (for $C_{33}H_{54}N_2O_5SiS$) Calcd. : C, 64.07% H, 8.79% N, 4.53% Found: C, 63.58% H, 8.74% N, 4.67%

(3) Mono-{2-[5-(3,5-dimethylphenylthio)-4-isopropyl-2-methyl-imidazol-1-ylmethoxy]ethyl} sebacate (69)

To a solution of the compound 64 (557 mg, 0.9 mmol) in N,N-dimethylformamide (4.5 mL) was added a solution of tetrabutylammonium fluoride in 1M tetrahydrofuran (1.8 mL), and allowed to stand at room temperature for 18 hours. The reaction mixture was partitioned between chloroform - methanol (10:1) and water. The organic layer was separated, washed with water, dried over magnesium sulfate, and concentrated under reduced pressure. The residue was purified by chromatography on a silica gel column (eluate: ethyl acetate) to give the compound 69 (210 mg, 45%) as oil. Rf 0.33 (EtOAc).

PMR (CDCl$_3$): δH1.26 (6 H, d, 7.0 Hz, (CH$_3$)$_2$CH), 1.32 (8 H, bs, —CH$_2$—), 1.62 (4 H, bm, —CH$_2$—), 2.22 (6 H, s, 3- and 5-CH$_3$), 2.26 and 2.35 (eaCH$_2$ H, t, 7.2 Hz, —CH$_2$CO—), 2.55 (3 H, s, 2-CH$_3$), 3.18 (1 H, sep, 6.8 Hz, (CH$_3$)$_2$CH), 3.49 (2 H, m, OCH$_2$CH$_2$OCO), 4.04 (2 H, m, OCH$_2$CH$_2$OCO), 5.27 (2 H, s, NCH$_2$O), 6.60 (2 H, s, arom 2- and 6-H), and 6.77 (1 H, s, arom 4-H). LSIMS: m/z 519 (M+H)+. Elementary analysis (for $C_{28}H_{42}N_2O_5S$) Calcd. : C, 64.83% H, 8.16% N, 5.40% Found: C, 64.71% H, 8.29% N, 5.28%

EXAMPLE 55 (1)

Mono-[2-(trimethylsilanyl)ethyl] dodecanediate (61)

Dodecanedioic acid (2.30 g, 10.0 mmol) was converted to the ester with 2-(trimethylsilyl)ethanol (1.18 g, 10.0 mmol) under N,N-dimethylaminopyridine (122 mg, 1.00 mmol) and 1,3-dicyclohexylcarbodiimide (2.26 g, 11 mmol) in the same manner as the example 54 (1) to give the compound 61 (1.55 g, 47%). Mp 44° C. Rf 0.51 (2:1 hexane-EtOAc).

PMR (CDCl$_3$): δH0.04 (9 H, s, (CH$_3$)$_3$Si), 0.98 (2 H, m, CH$_2$Si), 1.28 (12 H, bs, —CH$_2$—), 1.62 (4 H, bm, —CH$_2$—), 2.27 and 2.35 (each 2 H, t, 7.2 Hz, —CH$_2$CO—), and 4.15 (2 H, m, CH$_2$O). Elementary analysis (for $C_{17}H_{34}O_4Si$) Calcd.: C, 61.77% H, 10.37% Found: C, 61.82% H, 10.26%

(2) Mono-{2-[5-(3,5-dimethylphenylthio)-4-isopropyl-2-methyl-imidazol-1-ylmethoxy]ethyl 2-(trimethylsilanyl)ethyl dodecanedioate (65)

The compound 1 (335 mg, 1.00 mmol) was converted to the ester with the compound 61 (331 mg, 1.00 mmol) under N,N-dimethylaminopyridine and 1,3-dicyclohexylcarbodiimide (2.26 g, 11 mmol) in the same manner as the example 54 (2) to give the compound 65 (620 mg, 96%). Rf 0.34 (1:1 EtOAc-hexane).

PMR (CDCl$_3$): δH0.04 (9 H, s, (CH$_3$)$_3$Si), 0.98 (2 H, m, SiCH$_2$), 1.27 (18 H, m, (CH$_3$)$_2$CH and —CH$_2$—), 1.60 (4 H, bm,—CH$_2$—), 2.22 (6 H, s, 3- and 5-CH$_3$), 2.27 (4 H, t, 7.3 Hz, —CH$_2$CO—), 2.54 (3 H, s, 2-CH$_3$), 3.17 (1 H, sep, 7.3 Hz, (CH$_3$)$_2$CH), 3.48 (2 H, m, OCH$_2$CH$_2$OCO), 4.04 (2 H, m, OCH$_2$CH$_2$OCO), 4.16 (2 H, m, OCH$_2$), 5.27 (2 H, s, NCH$_2$O), 6.59 (2 H, s, arom 2-H and 6-H), and 6.75 (1 H, s, arom 4-H). Elementary analysis (for $C_{35}H_{58}N_2O_5SiS$) Calcd. : C, 64.97% H, 9.04% N, 4.33% Found: C, 64.22% H, 8.96% N, 4.37%

(3) Mono-{2-[5-(3,5-dimethyiphenylthio)-4-isopropyl-2-methyl-imidazol-1-ylmethoxy]ethyl dodecanedioate (70)

The compound 65 (610 mg, 0.942 mmol) was hydrolyzed to remove 2-(trimethylsilyl)ethyl group with a solution of tetrabutylammonium fluoride in 1M tetrahydrofuran in the same manner as the example 54 (3) to give the compound 70 (310 mg, 59%). Rf 0.41 (EtOAc). PMR (CDCl$_3$): δH1.26 (6 H, d, 7.2 Hz, (CH$_3$)$_2$CH), 1.28 ( 12 H, bm, —CH$_2$—), 1.62 (4 H, bm, —CH$_2$—), 2.22 (6 H, s, arom 3- and 5-CH$_3$), 2.27 and 2.36 (each 2 H, t, 7.2 Hz, —CH$_2$CO—), 2.55 (3 H, s, 2-CH$_3$, 3.18 (I H, sep, 7.2 Hz, (CH$_3$)$_2$CH), 3.48 (2 H, m, OCH$_2$CH$_2$HCO), 4.06 (2 H, m, OCH$_2$CH$_2$OCO), 5.27(2 H, s, NCH$_2$O), 6.60 (2 H, s, arom 2- and 6-H), and 6.76 (1 H, s, arom 4-H). LSIMS: m/z 547 (M+H)+. Elementary analysis (for $C_{30}H_{46}N_2O_5S$) Calcd.: C, 65.90% H, 8.48% N, 5.12% Found: C, 65.26% H, 8.41% N, 5.26%

EXAMPLE 56 (1)

Mono-[2-(trimethylsilanyl)ethyl] tetradecanedioate (62)

Tetradecanedioic acid (4.90 g, 19.0 mmol) was converted to the ester with 2-(trimethylsilyl)ethanol (2.25 g, 19.0 mmol) under N,N-dimethylaminopyridine and 1,3-dicyclohexylcarbodiimide in the same manner as the example 54 (1) to give the compound 62 (2.80 g, 47%). Mp 51–52° C.

PMR (CDCl$_3$): δH0.04 (9 H, s, (CH$_3$)$_3$Si),0.98 (2 H, m, CH$_2$Si), 1.28 (16 H, bs, —CH$_2$—), 1.63 (4 H, bm, —CH$_2$—), 2.27 and 2.31 (each 2 H, t, 7.2 Hz, —CH$_2$CO—), and 4.15 (2 H, m, CH$_2$O). Elementary analysis (for $C_{19}H_{38}O_4Si$) Calcd. : C, 63.64% H, 10.68% Found: C, 63.65% H, 10.59%

(2) 2-[5-(3,5-Dimethylphenylthio)-4-isopropyl-2-methyl-imidazol-1-ylmethoxy]ethyl 2-(trimethylsilanyl)ethyl tetradecanedioate (66)

The compound 1 (500 mg, 1.50 mmol) was converted to the ester with the compound 62 (538 mg, 1.50 mmol) under N,N-dimethylaminopyridine and 1,3-dicyclohexylcarbodiimide in the same manner as the example 54 (2) to give the compound 66 (990 mg, 98%). Rf 0.41 (1:1 EtOAc-hexane).

PMR (CDCl$_3$): δH0.04 (9 H, s, (CH$_3$)$_3$Si),0.98 (2 H, m, SiCH$_2$), 1.24 (22 H, m, (CH$_3$)$_2$CH and —CH$_2$—), 1.61 (4 H, bm, —CH$_2$—), 2.22 (6 H, s, 3- and 5-CH$_3$), 2.27 (4 H, t, 7.4 Hz, —CH$_2$CO—), 2.53 (3 H, s, 2-CH$_3$), 3.16 (1 H, sep, 7.2 Hz, (CH$_3$)$_2$CH), 3.48 (2 H, m, OCH$_2$CH$_2$OCO), 4.04 (2 H, m, OCH$_2$CH$_2$OCO), 4.15 (2 H. m, OCH$_2$), 5.27 (2 H, s, NCH$_2$O), 6.59 (2 H, s, arom 2-H and 6-H), and 6.75 (1 H, s, arom 4-H). Elementary analysis (for $C_{37}H_{62}N_2O_5Ssi$) Calcd. : C, 65.83% H, 9.26% N, 4.15% Found: C, 65.25% H, 9.10% N, 4.17%

(3) Mono-{2- [5-(3,5-dimethylphenylthio)-4-isopropyl-2-methyl-imidazol-1-ylmethoxy]ethyl} tetradecanedioate (71)

The compound 66 (950 mg, 1.40 mmol) was hydrolyzed to remove 2-(trimethylsilyl)ethyl group with a solution of tetrabutylammonium fluoride in 1M tetrahydrofuran in the same manner as the example 54 (3) to give the compound 71 (310 mg, 39%). Rf 0.44 (EtOAc).

PMR (CDCl$_3$): δH1.26 (6 H, d, 7.2 Hz, (CH$_3$)$_2$CH), 1.27 (16 H, bs, —CH$_2$—), 1.61 (4 H, bm, —CH$_2$—), 2.22 (6 H, s, arom 3- and 5-CH$_3$), 2.28 and 2.36 (each 2 H, t, 7.4 Hz, —CH$_2$CO—), 2.55 (3 H, s, 2-CH$_3$), 3.19 (1 H, sep, 7.2 Hz, (CH$_3$)$_2$CH), 3.47 (2 H, m, OCH$_2$CH$_2$OCO), 4.05 (2 H, m, OCH$_2$CH$_2$OCO), 5.27 (2 H, s, NCH$_2$O), 6.60 (2 H, s, arom 2- and 6-H), and 6.76 (1 H, s, arom 4-H). LSIMS: m/z 575

(M+H)+. Elementary analysis (for $C_{32}H_{50}N_2O_5S$) Calcd. : C, 66.86% H, 8.77% N, 4.87% Found: C, 66.09% H, 8.72% N, 4.89%

EXAMPLE 57 (1)

Mono- [2 -(trimethylsilanyl)ethyl] hexadecanedioate (63)

Hexadecanedlioic acid (2.86 g, 10.0 mmol) was converted to the ester with 2-(trimethylsilyl)ethanol (1.18 g, 10.0 mmol) under N,N-dimethylaminopyridine and 1,3-dlicyclohexylcarbodiimide in the same manner as the example 54 (1) to give the compound 63 (1.81 g, 47%) Mp 56–58° C.

PMR ($CDCl_3$): δH0.04 (9 H, s, $(CH_3)_3Si$),0.98 (2 H, m, $CH_2Si$), 1.25–1.35 (20 H, bs, —$CH_2$—), 1.61 (4 H, bm, —$CH_2$—), 2.27 and 2.35 (each 2 H, t, J 7.2 Hz, —$CH_2CO$—), and 4.17 (2 H, m, $CH_2O$). Elementary analysis (for $C_{21}H_{42}O_4Si$) Calcd. : C, 62.54% H,10.95% Found: C,.62.50% H,10.90%

(2) 2- [5-(3,5-Dichlorophenylthio)-4-isopropyl-2-methyl-imidazol- 1-ylmethoxy]ethyl 2-(trimethylsilanyl)ethyl hexadecanedioate (67)

The compound 8 (450 mg, 1.20 mmol) was converted to the ester with the compound 63 (464 mg, 1.20 mmol) under N,N-dimethylaminopyridine and 1,3-dicyclohexylcarbodiimide in the same manner as the example 54 (2) to give the compound 67 (625 mg, 70%). Rf 0.43 (1:1 EtOAc-hexane).

PMR ($CDCl_3$): δH0.04 (9H, s, $(CH_3)_3Si$),0.99 (2 H, m, $SiCH_2$), 1.23–1.27 (26 H, m,$(CH_3)_2CH$ and —$CH_2$—), 1.60 (4 H, m, —$CH_2$—), 2.27 and 2.28 (each 2 H, t, J 7.8 Hz, —$CH_2$—), 2.54 (3 H, 8, 2-$CH_3$), 3.10 (1 H, sep, J 7.2Hz, $(CH_3)_2CH$), 3.54 (2 H, m, $OCH_2CH_2OCO$), 4.08 (2 H, m, $OCH_2CH_2OCO$), 4.17 (2 H, m, $SiCH_2CH_2O$), 5.25 (2 H, s, $NCH_2O$), 6.82 (2 H, d, J 1.8 Hz, arom 2-H and 6-H), and 7.11 (1 H, t, J 1.8 Hz, arom 4-H). Elementary analysis (for $C_{37}H_{60}N_2O_5SCl_2Si$) Calcd. : C, 59.74% H, 8.13% N, 3.77% Found: C, 59.70% H, 8.13% N, 3.76%

(3) Mono-{2- [5-(3,5-dichlorophenylthio)-4-isopropyl-2-methyl-imidazol- 1-ylmethoxy]ethyl} hexadecanedioate (75)

The compound 67 (600 mg, 0.806 mmol) was hydrolyzed to remove 2-(trimethylsilyl)ethyl group with a solution of tetrabutylammonium fluoride in 1M tetrahydrofuran in the same manner as the example 54 (3) to give the compound 75 (502 mg, 80%). Mp 75–76° C.

PMR ($CDCl_3$): δH1.22–1.38 (26 H, m, $(CH_3)_2CH$ and —$CH_2$—),1.62 (4 H. bm, —$CH_2$—), 2.29 and 2.36 (each 2 H, t, J 7.5 and 7.2 Hz, —$CH_2$—), 2.56 (3 H, s, 2-$CH_3$), 3.11 (1 H, sep, J 6.9 Hz, $(CH_3)_2CH$), 3.53 (2 H, m, $OCH_2CH_2OCO$), 4.09 (2 H, m, $OCH_2CH_2OCO$), 5.26 (2 H, s, $NCH_2O$), 6.84 (2 H, d, 1.8 Hz, arom 2- and 6-H), and 7.12 (1 H, t, 1.8 Hz, arom 4-H). LSIMS: m/z 642 (M+H)+. Elementary analysis (for $C_{32}H_{48}N_2O_5SCl_2$) Calcd.: C, 59.71% H, 7.52. N, 4.35% Cl, 11.02% Found: C, 59.72% H, 7.53% N, 4.48% Cl, 10.87%

EXAMPLE 58

Mono-{2- [5-(3,5-dichlorophenylthio)-4-isopropyl-2-methyl-imidazol-1-ylmethoxy]ethyl succinate (76)

The compound 8 (563 mg, 1.50 mmol) was converted to the ester with succinic anhydride (150 mg, 1.50 mmol) under N,N-dimethylaminopyridine in the same manner as the example 53 to give the compound 76 (672 mg, 94%). Mp114–116° C. Rf 0.38 (10:1 $CHCl_3$-$CH_3OH$).

PMR ($CDCl_3$): δH1.24 (6 H, d, 7.0 Hz, $(CH_3)_2CH$), 2.55 (3 H, s, 2-$CH_3$), 2.63 (4 H, m, $COCH_2CH_2CO$), 3.11 (1 H, sep, 7.0 Hz, $(CH_3)_2CH$), 3.55 (2 H, m, $OCH_2CH_2OCO$), 4.12 (2 H, m, $OCH_2CH_2OCO$), 5.26 (2 H, s, $NCH_2O$), 6.84 (2 H, d, J 1.6 Hz, arom 2- and 6-H), and 7.13 (1 H, t, 1.6 Hz, arom 4-H). Elementary analysis (for $C_{20}H_{24}N_2O_5SCl_2$) Calcd. : C, 50.53% H, 5.09% N, 5.89% Cl, 14.92% Found: C, 50.62% H, 5.08% N, 5.92% Cl, 14.80%

EXAMPLE 59

2-[5-(3,5-Dimethylphenylthio)-4-isopropyl-2-methyl-imidazol- 1-ylmethoxy]ethyl (1,3-dipalmitoly)glyceryl succinate (72)

To a solution of the compound 68 (86.9 mg, 0.200 mmol), 1,3-dipalmitin (114 mg, 0.200 mmol) and N,N-dimethylaminopyridine (24.4 mg, 0.2 mmol) in methylene chloride (3 ml) was added 1,3-dicyclohexylcarbodiimide (41.2 mg, 0.200 mmol), and stirred at room temperature for 18 hours. The precipitated insoluble matter was filtered off, and the filtrate was concentrated under reduced pressure. The residue was purified by chromatography on a silica gel column (eluate: hexane - ethyl acetate (1:1)) to give the compound 72 (143 mg, 72%) as oil. Mp 32–33° C. Rf 0.65 (2:1 EtOAc-hexane).

PMR ($CDCl_3$): δH0.88 (6 H, t, 7.2 Hz, 2 x $CH_3$), 1.22-1.34 (54 H, m, —$CH_2$—), 1.26 (6 H, d, 7.2 Hz, $(CH_3)_2CH$), 1.60 (4 H, m, —$CH_2$—), 2.22 (6 H, s, arom 3- and 5-$CH_3$), 2.31 (4 H, t, 7.5 Hz, —$CH_2CO$—), 2.52 (3 H, s, 2-$CH_3$), 2.62 ( 4 H, s, $OCCH_2CH_2CO$), 3.16 (1 H, sep, 6.6 Hz, $(CH_3)_2CH$), 3.49 (2 H, m, $OCH_2CH_2OCO$), 4.06 (2 H, m, $OCH_2CH_2OCO$), 4.15 and 4.29 (2 H, dd, 12.0 Hz, 5.8 Hz and 2H, dd, 12.0 Hz, 4.4 Hz, respectivery, glyceryl 1- and 3-$CH_2$), 5.26 (1 H, m, Glyceryl CH), 5.27 (2 H, s, $NCH_2O$), 6.59 (2 H, s, arom 2- and 6-H), 6.75 (1 H, s, arom 4-H). LSIMS: m/z 985 (M+H)+Elementary analysis (for $C_{57}H_{96}N_2O_9S$) Calcd. : C, 69.47% H, 9.82% N, 2.84% Found: C, 69.19% H, 9.83% N, 2.93%

EXAMPLE 60

2-[5-(3,5-Dimethylphenylthio)-4-isopropyl-2-methyl-imidazol- 1-ylmethoxy]ethyl (1,3-dipalmitoyl)glyceryl sebacate (73)

The compound 69 (78.0 mg, 0.150 mmol) was converted to the ester with 1,3-dipalmitin (85.0 mg, 0.150 mmol) under 1,3-dicyclohexylcarbodiimide and N,N-dimethylaminopyridine in the same manner as the example 59 to give the compound 73 (132 mg, 82%). Mp 45–46° C. Rf 0.74 (2:1 EtOAc-hexane).

PMR ($CDCl_3$): δH0.89 (6 H, t, 7.2 Hz, 2 x $CH_3$), 1.22–1.34 (62 H, bm, —$CH_2$—),1.60 (8 H, m, —$CH_2$—), 2.22 (6 H, s, arom 3- and 5-$CH_3$), 2.24-2.35 (8 H, m, —$CH_2$—), 2.54 (3 H, s, 2-$CH_3$), 3.17 (1 H, sep, J 6.8 Hz, $(CH_3)_2CH$), 3.47 (2 H, m, $OCH_2CH_2OCO$), 4.06 (2 H, m, $OCH_2CH_2OCO$), 4.29 (2 H, dd, J 12.0 Hz, 6.3 Hz and 2H, dd, J 12.0 Hz, 6.3 Hz, respectivery, glyceryl 1- and 3-$CH_2$), 5.26 (1 H, m, glyceryl CH), 5.27 (2 H, s, $NCH_2O$), 6.59 (2H, s, arom 2- and 6-H), and 6.75 (1 H, s, arom 4-H). LSIMS: m/z 1069 (M+H)+. Elementary analysis (for $C_{63}H_{108}N_2O_9S$) Calcd. : C, 70.74% H, 10.18% N, 2.62% Found: C, 70.67% H, 10.16% N, 2.62%

EXAMPLE 61

2-[5-(3,5-Dimethylphenylthio)-4-isopropyl-2-methyl-imidazol- 1-ylmethoxy]ethyl 2,2-dimethylpropionyloxymethyl succinate (74)

To a suspension of the compound 68 (100 mg, 0.230 mmol) and potassium carbonate (48.0 mg, 0.345 mmol) in N,N-dimethylformamide (1 mL) was added pivaloyloxymethyl iodide (61 mg, 0.252 mmol), and stirred at room temperature for 2 hours. The reaction mixture was partitioned between ice-water and ethyl acetate - hexane (1:1)). The organic layer was separated, dried over sodium sulfate, and concentrated under reduced pressure. The residue was purified by chromatography on a silica gel column (eluate: hexane - ethyl acetate (1:1)) to give the compound 74 (111 mg, 88%) as pale yellow oil. Rf 0.15 (1:1 EtOAc-hexane).

PMR (CDCl$_3$): δH 1.21 (9 H, s, t-Bu),1.25 (6 H, d, 6.9 Hz, (CH$_3$)$_2$CH), 2.22 (6 H, s, arom 3- and 5-CH$_3$), 2.52 (3 H, s, 2-CH$_3$), 2.63 (4 H, m, COCH$_2$CH$_2$CO), 3.16 (1 H, sep, J 6.9 Hz, (CH$_3$)$_2$CH), 3.49 (2 H, m, OCH$_2$CH$_2$OCO), 4.05 (2 H, m, OCH$_2$CH$_2$OCO), 5.26 (2 H, s, NCH$_2$O), 5.75 (2 H, s, COOCH$_2$O), 6.59 (2 H, s, arom 2- and 6-H), and 6.75 (1 H, s, arom 4-H). Elementary analysis (for C$_{28}$H$_{40}$N$_2$O$_7$S) Calcd.: C, 61.29% H, 7.35% N, 5.11% Found: C, 61.08% H, 7.34% N, 5.09%

EXAMPLE 62

2- [5-(3,5-Dichlorophenylthio)-4-isopropyl-2-methyl-imidazol- 1 -ylmethoxy]ethyl 2,2-dimethylpropionyloxymethyl ether (77)

The compound 8 (375 mg, 1 mmol) was alkylated with the pivaloyloxymethyl iodide (1.21 g, 5 mmol) under potassium carbonate (415 mg, 3 mmol) in the same manner as the example 61 to give the compound 77 (158 mg, 32%) as oil. Rf 0.26 (1:1 EtOAc - hexane).

PMR (CDCl$_3$): δH1.21 (9 H, s, t-Bu), 1.24 (6 H, d, J 6.6 Hz, (CH$_3$)$_2$CH), 2.54 (3 H, s, 2-CH$_3$), 3.10 (1 H, sep, J 6.6 Hz, (CH$_3$)$_2$CH), 3.50 (2 H, m, OCH$_2$CH$_2$OCO), 3.61 (2 H, m, OCH$_2$CH$_2$OCO), 5.23 (2 H, s, OCH$_2$0), 5.26 (2 H, s, NCH$_2$O)6.83 (2 H, d, J 2 Hz, arom 2- and 6-H), and 7.10 (1 H, t, J 2 Hz, arom 4-H). Elementary analysis (for C$_{22}$H$_{30}$N$_2$O$_4$SCl$_2$) Calcd.: C, 53.99% H, 6.18% N, 5.72% Cl, 14.49% Found: C, 53.79% H, 6.16% N, 5.84% Cl, 14.75%

EXAMPLE 63

2-[5-(3,5-Dichlorophenylthio)-4-isopropyl-2-methyl-imidazol- 1 -ylmethoxy]ethyl 2,2-dimethylpropionyloxymethyl succinate (78)

The compound 76 (250 mg, 0.526 mmol) was converted to the ester with pivaloyloxymethyl iodide (140 mg, 0.578 mmol) under potassium carbonate (50.9 mg, 0.368 mmol) in the same manner as the example 61 to give the compound 78 (262 mg, 84%) as oil. Rf 0.18 (1:1 EtOAc - hexane).

PMR (CDCl$_3$): δH1.21 (9 H, s, t-Bu), 1.25 (6 H, d, J 7.2 Hz, (CH$_3$)$_2$CH), 2.54 (3 H, s, 2-CH$_3$), 2.65 (4 H, m, COCH$_2$CH$_2$CO), 3.10 (1 H, sep, J 7.2 Hz, (CH$_3$)$_2$CH), 3.54 (2 H, m, OCH$_2$CH$_2$OCO), 4.10 (2 H, m, OCH$_2$CH$_2$OCO), 5.25 (2 H, s, NCH$_2$O), 5.75 (2 H, s, COOCH$_2$O), 6.82 (2 H, d, J 1.8 Hz, arom 2- and 6-H), and 7.12 (1 H, t, J 1.8 Hz, arom 4-H). Elementary analysis (for C$_{26}$H$_{34}$N$_2$O$_7$SCl$_2$) Calcd. : C, 52.97% H,5.81% N, 4.75% Cl, 12.03% Found: C, 52.93% H,5.95% N, 4.76% Cl, 12.19%

EXAMPLE 64

1-{2-[5-(3,5-Dichlorophenylthio)-4-isopropyl-2-methyl-imidazol- 1-ylmethoxy]ethyl} 16-(2,2-dimethylpropionyloxymethyl) hexadecanedioic acid diester (79)

The compound 75 (250 mg, 0.388 mmol) was converted to the ester with pivaloyloxymethyl iodide (141 mg, 0.582 mmol) under potassium carbonate (53.6 mg, 0.388 mmol) in the same manner as the example 61 to give the compound 79 (235 mg, 80%) as oil. Rf 0.47 (1:1 EtOAc-hexane).

PMR (CDCl$_3$): δH1.21 (9 H, s, t-Bu), 1.23–1.26 (26 H, m, —CH$_2$—, (CH$_3$)$_2$CH), 1.60 (4 H, m, —CH$_2$—), 2.35 and 2.38 (each 2 H, t, 7.5 Hz and 7.8 Hz, —CH$_2$—), 2.54 (3 H, s, 2-CH$_3$), 3.10 (1 H, sep, 7.2 Hz, (CH$_3$)$_2$CH), 3.52 (2 H, m, OCH$_2$CH$_2$OCO), 4.08 (2 H, m, OCH$_2$CH$_2$OCO), 5.25 (2 H, s, NCH$_2$O), 5.75 (2 H, s, COOCH$_2$O), 6.82 (2 H, d, 1.8 Hz, arom 2- and 6-H), and 7.11 (1 H, t, 1.8 Hz, arom 4-H). Elementary analysis (for C$_{38}$H$_{58}$N$_2$O$_7$SCl$_2$) Calcd. : C, 60.22% H,7.71% N, 3.70% Cl, 9.36% Found: C, 60.18% H,7.73% N, 3.74% Cl, 9.46%

EXAMPLE 65

5-(3,5-Dichlorophenylthio)-1-ethyl-4-isopropyl-1H-imidazol-2-ylmethyl acetylcarbamate (80)

To a suspension of the compound 19 (77.6 mg, 0.200 mmol) in acetic anhydride (1 mL) was added conc. sulfuric acid (0.24 eq.), and heated with reflux at 110° C. for 1 hour. Triethylamine (0.1 mL) was added to the reaction mixture, and the mixture was concentrated under reduced pressure. The residue was purified by chromatography on a silica gel column (eluate: ethyl acetate) to give the compound 80 (31 mg, 35%) as crystals. Mp. 163–164° C. (hexane-ether) Rf 0.10 (1:2 EtOAc - hexane)

PMR (CDCl$_3$): δH1.22 (3 H, t, J 6.9 Hz, CH$_2$CH$_3$), 1.25 (6 H, d, J 7.2 Hz, (CH$_3$)$_2$CH), 2.44 (3 H, s, CH$_3$CO), 3.11 (1 H, sep, J 7.2 Hz, (CH$_3$)$_2$CH), 4.01 (2 H, q, J 6.9 Hz, CH$_2$CH$_3$), 5.29 (2 H, s, CH$_2$O), 6.80 (2 H, d, J 1.5 Hz, arom 2- and 6-H), 7.13 (1 H, t, J 1.5 Hz, arom 4-H), 7.50 (1 H, bs, NH). IR (CHCl$_3$) cm$^{-1}$: 3396 (NH), 1790 and1765 (NCO), 1719 (NCOO). Elementary analysis (for C$_{18}$H$_{21}$N$_3$O$_3$SCl$_2$) Calcd. : C, 50.24% H, 4.92% N, 9.76% S, 7.45% Cl, 16.48% Found: C, 49.93% H, 4.90% N, 9.70% S, 7.42% Cl, 16.31%

EXAMPLE 66

5-(3,5-Dichlorophenylthio)-1-ethyl-4-isopropyl-1H-imidazol-2-ylmethyl pivaloylcarbamate (81)

To a solution of the compound 19 (200 mg, 0.580 mmol) in tetrahydrofuran (1 mL) under ice-cooling was added pivaloyl isocyanate (5 eq.), and stirred at the same temperature for 1 hour. After removing condenser, the reaction mixture was stirred at room temperature for 1 hour. The reaction mixture was partitioned between ethyl acetate and phosphate buffer (pH 7.0). The organic layer was separated, washed with water, dried over sodium sulfate, and concentrated under reduced pressure. The residue was purified by chromatography on a silica gel column (eluate: hexane - ether (2:1)) to give the compound 81 (227 mg, 83%) as crystals. Mp. 157–159° C. Rf 0.31 (1:2 EtOAc-hexane).

PMR (CDCl$_3$): δH 1.20 (3 H, t, J 7.2 Hz, CH$_2$CH$_3$), 1.24 (9 H, s, (CH$_3$)$_3$C), 1.26 (6 H, d, J 6.9 Hz, (CH$_3$)$_2$CH), 3.11 (1 H, sep, J 6.9 Hz, (CH$_3$)$_2$CH), 4.05 (2 H, q, J 6.9 Hz, CH$_2$CH$_3$), 5.31 (2 H, s, CH$_2$O), 6.81 (2 H, d, J 1.8 Hz, arom 2- and 6-H), 7.13 (1 H, t, J 1.8 Hz, arom 4-H), 7.86 (1 H, s, NH). IR (CHCl$_3$) cm$^{-1}$ 3440 (NH), 1790 and 1746 (NCO), 1720 (NCOO). Elementary analysis (for C$_{21}$H$_{27}$N$_3$O$_3$SCl$_2$) Calcd.: C, 53.39% H, 5.76% N, 8.89% S, 6.79% Cl, 15.01% Found: C, 53.21% H, 5.79% N, 8.79% S, 6.59% Cl, 14.81%

EXAMPLE 67

5-(3,5-Dichlorophenylthio)-1-ethyl-4-isopropyl-1H-imidazol-2-ylmethyl octanoylcarbamate (82)

The compound 19 (104 mg, 0.3 mmol) was converted to the carbamate with ocatanoyl isocyanate (5 eq.) in the same manner as the example 66 to give the compound 82 (97 mg, 63%) as crystals. Mp. 99–101° C. Rf 0.24 (1:2 EtOAc - hexane) PMR (CDCl$_3$): δH0.88 (3 H, t like, CH$_3$), 1.22 (3 H, t, J 7.5 Hz, CH$_3$), 1.20–1.37 (14 H, m, —CH$_2$—and (CH$_3$)$_2$CH), 1.61 (2 H, m, —CH$_2$—), 2.73 (2 H, t, —CH$_2$CO—), 3.11 (1 H, sep, J 6.9 Hz, (CH$_3$)$_2$CH), 4.01 (2 H, q, 7.5 Hz, CH$_2$CH$_3$), 5.28 (2 H, s, CH$_2$O), 6.80 (2 H, d, J 1.5 Hz, arom 2- and 6-H), 7.13 (1 H, t, J 1.5 Hz, arom 4-H), 7.50 (1 H, bs, NH). IR (CHCl$_3$)cm$^{-1}$ 3394 (NH), 1792 and 1763 (NCO), 1714 (NCOO). Elementary analysis (for C$_{24}$H$_{33}$N$_3$O$_3$SCl$_2$) Calcd. : C, 56.03% H, 6.46% N, 8.17% S, 6.23% Cl, 13.78% Found: C, 56.14% H, 6.55% N, 8.08% S, 5.95% Cl, 13.49%

EXAMPLE 68

5-(3,5-Dichlorophenylthio)-1-ethyl-4-isopropyl-1H-imidazol-2-ylmethyl decanoylcarbamate (83)

The compound 19 (240 mg, 0.695 mmol) was converted to the carbamate with decanoyl isocyanate (205 mg, 1.04 mmol) in the same manner as the example 66 to give the compound 83 (335 mg, 92%) as crystals. Mp. 102–103° C. Rf 0.28 (1:2 EtOAc - hexane).

PMR (CDCl$_3$): δH0.88 (3 H, t like, CH$_3$), 1.22 (3 H, t, J 7.5 Hz, CH$_3$), 1.20–1.37 (12 H, m, —CH$_2$—), 1.25 (6 H, d, (CH$_3$)$_2$CH), 1.65 (2 H, m, —CH$_2$—), 2.73 (2 H, t, J 7.6 Hz, —CH$_2$CO—), 3.11 (1 H, sep, J 6.9 Hz, (CH$_3$)$_2$CH), 4.01 (2 H, q, J 7.4 Hz, CH$_2$CH$_3$), 5.28 (2 H, s, CH$_2$O), 6.80 (2 H, d, J 1.6 Hz, arom 2- and 6-H), 7.13 (1 H, t, J 1.6 Hz, arom 4-H), 7.48 (1 H, s, NH). IR (CHCl$_3$)cm$^{-1}$ 3394 (NH), 1793 and 1764 (NCO), 1715 (NCOO). Elementary analysis (for C$_{26}$H$_{37}$N$_3$O$_3$SCl$_2$) Calcd.: C, 57.56% H, 6.87% N, 7.74% S, 5.91% Cl, 13.07% Found: C, 57.45% H, 6.96% N, 7.68% S, 5.94% Cl, 13.18%

EXAMPLE 69

5-(3,5-Dichlorophenylthio)-1-ethyl-4-isopropyl-1H-imidazol-2-ylmethyl lauroylcarbamate (84)

The compound 19 (345 mg, 1.00 mmol) was converted to the carbamate with lauroyl isocyanate (5 eq.) in the same manner as the example 66 to give the compound 84 (430 mg, 71%) as crystals. Mp. 100–102° C. Rf 0.32 (1:2 EtOAc - hexane).

PMR (CDCl$_3$): δH0.88 (3 H, t like, CH$_3$),1.22 (3 H, t, J 7.2 Hz, CH$_3$), 1.20–1.35 (22 H, m, —CH$_2$— and (CH$_3$)$_2$CH), 1.62 (2 H, m, —CH$_2$—), 2.72 (2 H, t, J 7.5 Hz, —CH$_2$CO—), 3.11 (1 H, sep, J 6.6 Hz, (CH$_3$)$_2$CH), 4.01 (2 H, q, J 7.2 Hz, CH$_2$CH$_3$), 5.28 (2 H, s, CH$_2$O), 6.80 (2 H, d, J 1.5 Hz, arom 2- and 6-H), 7.13 (1 H, t, J 1.5 Hz, arom 4-H), 7.52 (1 H, bs, NH). IR (CHCl$_3$)cm$^{-1}$ 3394 (NH), 1792 and 1760 (NCO), 1714 (NCOO). Elementary analysis (for C$_{28}$H$_{41}$N$_3$O$_3$SCl$_2$) Calcd. : C, 58.94% H, 7.24% N, 7.36% S, 5.62% Cl, 12.43% Found: C, 59.02% H, 7.19% N, 7.38% S, 5.56% Cl, 12.13%

EXAMPLE 70

5-(3,5-Dichlorophenylthio)-1-ethyl-4-isopropyl-1H-imidazol-2-ylmethyl palmitoylcarbamate (85)

The compound 19 (250 mg, 0.725 mmol) was converted to the carbamate with palmitoyl isocyanate (5 eq.) in the same manner as the example 66 to give the compound 85 (259 mg, 57%). Mp. 95–97° C. Rf 0.33 (1:2 EtOAc - hexane).

PMR (CDCl$_3$): δH0.88 (3 H, t like, CH$_3$), 1.22 (3 H, t, J 6.9 Hz, CH$_3$), 1.20–1.35 (30 H, m, —CH$_2$— and (CH$_3$)$_2$CH), 1.64 (2 H, m, —CH$_2$—), 2.73 (2 H, t, J 7.5 Hz, —CH$_2$—), 3.11 (1 H, sep, J 6.9 Hz, (CH$_3$)$_2$CH)), 4.01 (2 H, q, J 6.9 Hz, CH$_2$CH$_3$), 5.28 (2 H, s, CH$_2$O), 6.80 (2 H, d, J 1.5 Hz, arom 2- and 6-H), 7.13 (1 H, t, J 1.5 Hz, arom 4-H), 7.50 (1 H, s, NH). IR (CHCl$_3$)cm$^{-1}$ 3394 (NH), 1791 and 1754 (NCO), 1714 (NCOO). Elementary analysis (for C$_{32}$H$_{49}$N$_3$O$_3$SCl$_2$) Calcd.: C, 61.33% H, 7.88% N, 6.70% S, 5.12% Cl, 11.31% Found: C, 61.52% H, 7.96% N, 6.65% S, 5.04% Cl, 10.92%

EXAMPLE 71

5-(3,5-Dichlorophenylthio)-1-ethyl-4-isopropyl-1H-imidazol-2-ylmethyl 4-chlorobenzoylcarbamate (86)

The compound 19 (69 mg, 0.2 mmol) was converted to the carbamate with 4-chlorobenzoyl isocyanate (5 eq.) in the same manner as the example 66 to give the compound 86 (26 mg, 25%) as crystals. Mp. 82–83° C. Rf 0.13 (1:2 EtOAc - hexane).

PMR (CDCl$_3$): δH1.23 (3 H, t, J 7.5 Hz, CH$_3$), 1.26 (6 H, d, J 6.9 Hz, (CH$_3$)$_2$CH), 3.12 (1 H, sep, J 6.9 Hz, (CH$_3$)$_2$CH)), 4.06 (2 H, q, J 6.9 Hz, CH$_2$CH$_3$), 5.37 (2 H, s, CH$_2$O), 6.82 (2 H, d, J 1.8 Hz, arom 2- and 6-H), 7.13 (1 H, t, J 1.8 Hz, arom 4-H), 7.47 and 7.77 (each 2 H, d, J 8.7 Hz, 4-chlorobenzoyl 2-, 3-, 5- and 6-H), and 8.35 (1 H, bs, NH). IR(KBr)cm$^{-1}$ 3394 (NH), and 1789 and 1766 (NCO), 1714 (NCOO). Elementary analysis (for C$_{23}$H$_{22}$N$_3$O$_3$SCl$_3$) Calcd. : C, 52.43% H, 4.21% N, 7.98% Cl, 20.19% Found: C, 52.13% H, 4.23% N, 7.85% Cl, 20.21%

EXAMPLE 72

5-(3,5-Dichlorophenylthio)-1-ethyl-4-isopropyl-1H-imidazol-2-ylmethyl 3,5-dichlorobenzoylcarbamate (87)

The compound 19 (300 mg, 0.869 mmol) was converted to the carbamate with 3,5-dichlorobenzoyl isocyanate (1.5 eq.) in the same manner as the example 66 to give the compound 87 (380 mg, 78%) as crystals. Mp.124–125° C. Rf 0.23 (1:2 EtOAc-hexane)

PMR (CDCl$_3$): δH1.23 (3 H, t, J 7.5 Hz, CH$_3$), 1.24 (6 H, d, J 6.9 Hz,(CH$_3$)$_2$CH), 3.12 (1 H, sep, J 7.2 Hz, (CH$_3$)$_2$CH), 4.05 (2 H, q, J 6.9 Hz, CH$_2$CH$_3$), 5.37 (2 H, s, CH$_2$O), 6.82 (2 H, d, J 1.8 Hz, arom 2- and 6-H), 7.13 (1 H, d, J 1.8 Hz, arom 4-H), 7.58 (1 H, t, J 1.5 Hz, 3, 5-dichlorobenzoyl 6-H), 7.70 (1 H, t, J 1.8 Hz, 3, 5-dichlorobenzoyl 2- and 4-H), 8.55 (1 H, bs, NH). IR(KBr)cm$^{-1}$ 3416 (NH), and 1790 and 1750 (NCO), 1714 (NCOO). Elementary analysis (for C$_{23}$H$_{21}$N$_3$O$_3$SCl$_4$) Calcd. : C, 49.32% H, 3.77% N, 7.49% Cl, 25.26% Found: C, 49.27% H, 3.96% N, 7.36% Cl, 25.06%

EXAMPLE 73

Bis-[5-(3,5-dichlorophenylthio)-1-ethyl-4-isopropyl-1H-imidazol-2-ylmethyl] carbonate (88)

To a solution of the compound 19 (104 mg, 0.3 mmol) and triethylamine (61 mg, 0.6 mmol) in toluene (1.6 mL) was added a solution of chlorocarbonyl isocyanate (10 mg, 0.1 mmol) in toluene (0.1 mL) under ice-cooling. The reaction mixture was stirred under ice-cooling for 30 minutes, removed the condenser, and stirred at room temperature for 1 hour. The reaction mixture was distributed between phosphate buffer (pH 7) and ethyl acetate. The organic layer was purified by chromatography on a silica gel column (eluate: ethyl acetate) to give the compound 88 (22 mg, 21%). Mp 73–76° C. LSIMS:m/z 758 [M+H]+PMR (CDCl$_3$): δH1.19 (6 H, t, J 7.4 Hz), 1.22 (12 H, d, J 6.8 Hz), 3.10 (2 H, sep, J 6.9 Hz), 4.01 (4 H, q, J 7.4 Hz), 5.30 (4 H, s), 6.79 (4 H, d, J 1.6 Hz), 7.11 (2 H, t, J 1.6 Hz), 8.00 (1 H, bs) IR(CHCl$_3$)cm$^{-1}$ 3418, 1810, 1741 Elementary analysis (for C$_{32}$H$_{35}$N$_5$O$_4$S$_2$Cl$_4$) Calcd. : C, 50.60% H, 4.64% N, 9.22% Found: C, 51.04% H, 4.99% N, 8.74%

EXAMPLE 74

5-(3,5-Dichlorophenylthio)-4-isopropyl-1-(4-pyridylmethyl)-1H-imidazol-2-ylmethyl acetylcarbamate (90)

5-(3,5-Dichlorophenylthio)-4-isoproyl-1-(4-pyridylmethyl)-2-hydroxymethyl-1H-imidazole (89) (245 mg, 0.6 mmol) prepared in accordance with the method as described in WO 96/10019 was converted to the carbamate with acetyl isocyanate (5 eq.) in the same manner as the example 66 to give the compound 90 (225 mg, 76%) as crystals. Mp. 135–137° C. Rf 0.32 (10:1 EtOAc - CH$_3$OH).

PMR (CDCl$_3$): δH1.31 (6 H, d, J 6.6 Hz, (CH$_3$)$_2$CH), 2.33 (3 H, s, NCH$_3$), 3.19 (1 H, sep, J 6.9 Hz, (CH$_3$)$_2$CH), 5.22 (2 H, s, NCH$_2$), 5.27 (2 H, s, OCH$_2$), 6.70 (2 H, d, J 1.8 Hz, arom 2- and 6-H), 6.76 (2 H, d-like, 4-pyridyl 2- and 6-H), 7.06 (1 H, t, J 1.8 Hz, arom 4-H), 7.25 (1 H, bs, NH), 8.48 (2 H, d-like, 4-pyridyl 3- and 5-H). IR (CHCl$_3$) cm$^{-1}$ 3397 (NH), 1790 and 1765 (NCO), 1721 (NCOO). Elementary analysis (for C$_{22}$H$_{22}$N$_4$O$_3$SCl$_2$) Calcd.: C, 53.55% H, 4.49% N, 11.35% S, 6.50% Cl, 14.37% Found: C, 53.28% H, 4.58% N, 10.66% S, 5.96% Cl, 13.88%

EXAMPLE 75

5-(3,5-Dichlorophenylthio)-4-isopropyl-1-(4-pyridylmethyl)-1H-imidazol-2-ylmethyl octanoylcarbamate (91)

The compound 89 (101-1048 (816 mg, 2.00 mmol) was converted to the carbamate with octanoyl isocyanate (5 eq.) in the same manner as the example 66 to give the compound 91 (650 mg, 56%) as crystals. Mp. 139–141° C. Rf 0.34 (EtOAc).

PMR (CDCl$_3$): δH0.88 (3 H, t like, CH$_2$CH$_3$), 1.26 (8 H, m, —CH$_2$—), 1.31 (6 H, d, J 6.9 Hz, (CH$_3$)$_2$CH), 1.60 (2 H, m, —CH$_2$—), 2.59 (2 H, t, J 7.6 Hz, —CH$_2$CO—), 3.19 (1 H, sep, J 6.9 Hz, (CH$_3$)$_2$CH), 5.22 (2 H, s, NCH$_2$), 5.26 (2 H, s, OCH$_2$), 6.70 (2 H, d, J 1.8 Hz, arom 2- and 6-H), 6.76 (2 H, d-like, 4-pyridyl 2- and 6-H), 7.06 (1 H, t, J 1.8 Hz, arom 4-H), 7.15 (1 H, bs, NH), 8.60 (2 H, d-like, 4-pyridyl 3- and 5-H). IR (CHCl$_3$) cm$^{-1}$ 3394 (NH), 1791 and 1764 (NCO), 1715 (NCOO). Elementary analysis (for C$_{28}$H$_{34}$N$_4$O$_3$SCl$_2$) Calcd.: C, 58.23% H, 5.93% N, 9.70% S, 5.55% Cl, 12.28% Found: C, 58.16% H, 6.04% N, 9.61% S, 5.49% Cl, 12.22%

EXAMPLE 76

5-(3,5-Dichlorophenylthio)-4-isopropyl-1-(4-pyridylmethyl)- 1H-imidazol-2-ylmethyl decanoylcarbamate (92)

The compound 89 (245 mg, 0.6 mmol) was converted to the carbamate with decanoyl isocyanate (5 eq.) in the same manner as the example 66 to give the compound 92 (152 mg, 42%) as crystals. Mp. 84–86° C. Rf 0.37 (EtOAc).

PMR (CDCl$_3$): δH0.88 (3 H, t like, CH$_3$), 1.27 (12 H, bs, —CH$_2$—), 1.31 (6 H, d, J 6.9 Hz, (CH$_3$)$_2$CH), 1.59 (2 H, m, —CH$_2$—), 2.59 (2 H, t, J 7.2 Hz, —CH$_2$CO—), 3.19 (1 H, sep, J 6.9 Hz, (CH$_3$)$_2$CH), 5.22 (2 H, s, NCH$_2$), 5.27 (2 H, s, OCH$_2$), 6.70 (2 H, d, J 1.6 Hz, arom 2- and 6-H), 6.76 (2 H, d-like, 4-pyridyl 2- and 6-H), 7.06 (1 H, t, J 1.6 Hz, arom 4-H), 7.24 (1 H, bs, NH), 8.48 (2 H, d-like, 4-pyridyl 3- and 5-H). IR(CHCl$_3$)cm$^{-1}$ 3394 (NH), 1790 and 1764 (NCO), 1715 (NCOO). Elementary analysis (C$_{30}$H$_{38}$N$_4$O$_3$SCl$_2$) Calcd.: C, 59.50% H, 6.32% N, 9.25% S, 5.29% Cl, 11.71% Found: C, 59.44% H, 6.42% N, 9.43% S, 5.00% Cl, 11.45%

EXAMPLE 77

5-(3,5-Dichlorophenylthio)-4-isopropyl-1-(4-pyridylmethyl)-1H-imidazol-2-ylmethyl lauroylcarbamate (93) and the hydrochloride The compound 89 (204 mg, 0.5 mmol) was converted to the carbamate with lauroyl isocyanate (5 eq.) in the same manner as the example 66 to give the compound 93 (215 mg, 67%) as oil. Rf 0.41 (EtOAc). PMR (CDCl$_3$): δH 0.88 (3 H, t like, CH$_3$), 1.25 (16 H, bs, —CH$_2$—), 1.31 (6 H, d, J 6.9 Hz, (CH$_3$)$_2$CH), 1.60 (2 H, m, —CH$_2$—), 2.58 (2 H, t, J 7.2 Hz, —CH$_2$CO—), 3.19 (1 H, sep, J 6.9 Hz, (CH$_3$)$_2$CH), 5.22 (2 H, s, NCH$_2$), 5.27 (2 H, s, OCH$_2$), 6.70 (2 H, d, 1.8 Hz, arom 2- and 6-H), 6.76 (2 H, d-like, 4-pyridyl 2- and 6-H), 7.06 (1 H, t, J 1.8 Hz, arom 4-H), 7.30 (1 H, bs, NH), 8.46 (2 H, d-like, 4-pyridyl 3- and 5-H). IR (CHCl$_3$) cm$^{-1}$ 3394 (NH), 1790 and 1764 (NCO), 1714 (NCOO). Elementary analysis (for C$_{32}$H$_{42}$N$_4$O$_3$SCl$_2$) Calcd.: C, 60.65% H, 6.68% N, 8.84% S, 5.06% Cl, 11.19% Found: C, 60.39% H, 6.85% N, 8.95% S, 4.87% Cl, 10.92%

To a solution of the compound 93 in ethanol was added conc. hydrochloric acid (2 eq.), and the mixture was concentrated under reduced pressure. The residue was crystallized from a mixture of ethanol - acetone to give hydrochloride of the compound 93. Mp. 168–170° C. Elementary analysis (for C$_{32}$H$_{44}$N$_4$O$_3$SCl$_4$·H$_2$O) Calcd. : C, 53.04% H, 6.40% N, 7.73% S, 4.42% Cl, 19.57% Found: C, 53.57% H, 6.42% N, 8.18% S, 4.35% Cl, 18.95%

EXAMPLE 78

5-(3,5-Dichlorophenylthio)-4-isopropyl-1-(4-pyridylmethyl)-1H-imidazol-2-ylmethyl myristoylcarbamate (94)

The compound 89 (245 mg, 0.6 mmol) was converted to the carbamate with myristoyl isocyanate (5 eq.) in the same manner as the example 66 to give the compound 94 (182 mg, 46%) as oil. Rf 0.41 (EtOAc).

PMR (CDCl$_3$): δH0.88 (3 H, t like, CH$_3$), 1.25 (20 H, bs, —CH$_2$—), 1.31 (6 H, d, J 7.0 Hz, (CH$_3$)$_2$CH), 1.58 (2 H, m, —CH$_2$—), 2.59 (2 H, t, J 7.4 Hz, —CH$_2$CO—), 3.18 (1 H, sep, J 7.0 Hz, (CH$_3$)$_2$CH), 5.22 (2 H, s, NCH$_2$), 5.27 (2 H, s, OCH$_2$), 6.70 (2 H, d, J 1.6 Hz, arom 2- and 6-H), 6.76 (2 H, d-like, 4-pyridyl 2- and 6-H), 7.07 (1 H, t, J 1.6 Hz, arom 4-H), 7.21 (1 H, bs, NH), 8.48 (2 H, d-like, 4-pyridyl 3- and 5-H). IR(CHCl$_3$) cm$^{-1}$ 3394 (NH), 1791 and 1764 (NCO), 1715 (NCOO). Elementary analysis (C$_{34}$H$_{46}$N$_4$O$_3$SCl$_2$) Calcd.: C, 61.71% H, 7.01% N, 8.47% S, 4.85% Cl, 10.72% Found: C, 62.46% H, 7.55% N, 8.14% S, 4.74% Cl, 10.25%

EXAMPLE 79

5-(3,5-Dichlorophenylthio)-4-isopropyl-1-(4-pyridylmethyl)-1H-imidazol-2-ylmethyl palmitoylcarbamate (95)

The compound 89 (245 mg, 0.6 mmol) was converted to the carbamate with palmitoyl isocyanate (5 eq.) in the same manner as the example 66 to give the compound 95 (207 mg, 50%) as oil. Rf 0.40 (EtOAc). PMR (CDCl$_3$): δH0.88 (3 H, t like, CH$_3$),1.25 (24 H, bs, —CH$_2$—), 1.31 (6 H, d, J 7.0 Hz, (CH$_3$)$_2$CH), 1.59 (2 H, m, —CH$_2$—), 2.59 (2 H, t, J 7.8 Hz, —CH$_2$CO—), 3.19 (1 H, sep, J 7.0 Hz, (CH$_3$)$_2$CH), 5.22 (2 H, s, NCH$_2$), 5.27 (2 H, s, OCH$_2$), 6.70 (2 H, d, J 1.6 Hz, arom 2- and 6-H), 6.76 (2 H, d-like, 4-pyridyl 2- and 6-H), 7.06 (1 H, t, J 1.6 Hz, arom 4-H), 7.35 (1 H, bs, NH), 8.46 (2 H, d-like, 4-pyridyl 3- and 5-H). IR (CHCl$_3$)cm$^{-1}$ 3394 (NH), 1792 and 1764 (NCO), 1716 (NCOO). Elementary analysis (for C$_{34}$H$_{46}$N$_4$O$_3$SCl$_2$) Calcd.: C, 62.69% H, 7.31% N, 8.12% S, 4.65% Cl, 10.28% Found: C, 61.89% H, 7.66% N, 8.41% S, 4.56% Cl, 9.65% hydrochloride of the compound 95 mp. 158–160° C. Elementary analysis (for C$_{36}$H$_{52}$N$_4$O$_3$SCl$_4$) Calcd.: C, 56.69% H, 6.87% N, 7.35% S, 4.20% Cl, 18.59% Found: C, 55.85% H, 6.71% N, 7.64% S, 4.28% Cl, 18.66%

EXAMPLE 80

5-(3,5-Dichlorophenylthio)-4-isopropyl-1-(4-pyridylmethyl)- 1H-imidazol-2-ylmethyl stearoylcarbamate (96)

The compound 89 (245 mg, 0.6 mmol) was converted to the carbamate with stearoyl isocyanate (5 eq.) in the same manner as the example 66 to give the compound 96 (179 mg, 42%). Mp. 73–77° C. Rf 0.46 (EtOAc).

PMR (CDCl$_3$): δH0.88 (3 H, t like, CH$_3$), 1.25 (24 H, bs,—CH$_2$—), 1.31 (6 H, d, J 6.9 Hz, (CH$_3$)$_2$CH), 1.60 (2 H, m, —CH$_2$—), 2.58 (2 H, t, J 7.5 Hz, —CH$_2$CO—), 3.19 (1 H, sep, J 6.9 Hz, (CH$_3$)$_2$CH), 5.22 (2 H, s, NCH$_2$), 5.28 (2 H, s, OCH$_2$), 6.70 (2 H, d, J 1.8 Hz, arom 2- and 6-H), 6.76 (2 H, d-like, 4-pyridyl 2- and 6-H), 7.06 (1 H, t, J 1.8 Hz, arom 4-H), 7.26 (1 H, bs, NH), 8.48 (2 H, d-like, 4-pyridyl 3- and 5-H). IR (CHCl$_3$) cm$^{-1}$ 3394 (NH), 1791 and 1764 (NCO), 1715 (NCOO). Elementary analysis (for C$_{38}$H$_{54}$N$_4$O$_3$SCl$_2$) Calcd.: C, 63.58% H, 7.58% N, 7.80% S, 4.47% Cl, 9.88% Found: C, 64.19% H, 7.83% N, 7.65% S, 4.21% Cl, 8.73%

EXAMPLE 81

5-(3,5-ichlorophenylthio)-4-isopropyl-1-(4-pyridylmethyl)-1H-imidazol-2-ylmethyl cis-oleoylcarbamate (97)

The compound 89 (327 mg, 0.8 mmol) was converted to the carbamate with oleoyl isocyanate (5 eq.) in the same manner as the example 66 to give the compound 97 (350 mg, 61%) as oil. Rf 0.42 (EtOAc). PMR (CDCl$_3$): δH0.88 (3 H, t like, CH$_3$),1.25 (20 H, bs, —CH$_2$—), 1.31 (6 H, d, J 6.8 Hz, (CH$_3$)$_2$CH), 1.60 (2 H, m, —CH$_2$—), 2.00 (4 H, m, —CH$_2$—), 2.58 (2 H, t, J 7.4 Hz, —CH$_2$CO—), 3.18 (1 H, sep, J 6.9 Hz, (CH$_3$)$_2$CH), 5.21 (2 H, s, NCH$_2$), 5.27 (2 H, s, OCH$_2$), 5.35 (2 H, m, CH═CH), 6.70 (2 H, d, J 1.8 Hz, arom 2- and 6-H), 6.76 (2 H, d-like, 4-pyridyl 2- and 6-H), 7.06 (1 H, t, J 1.8 Hz, arom 4-H), 7.27 (1 H, bs, NH), 8.46 (2 H, d-like, 4-pyridyl 3- and 5-H). IR (CHCl$_3$)cm$^{-1}$: 3394 (NH), 1791 and 1764 (NCO), 1716 (NCOO). Elementary analysis (for C$_{38}$H$_{52}$N$_4$O$_3$SCl$_2$) Calcd.: C, 63.76% H, 7.32% N, 7.83% S, 4.48% Cl, 9.91% Found: C, 63.45% H, 7.44% N, 7.89% S, 4.23% Cl, 10.07% hydrochloride mp. 158–161° C. Elementary analysis (for C$_{38}$H$_{54}$N$_4$O$_3$SCl$_4$) Calcd.: C, 57.87% H, 6.90% N, 7.10% S, 4.07% Cl, 17.98% Found: C, 57.32% H, 6.88% N, 7.28% S, 4.19% Cl, 17.56%

EXAMPLE 82

5-(3,5-Dichlorophenylthio)-4-isopropyl-1-(4-pyridylmethyl)-1H-imidazol-2-ylmethyl octyl iminodicaboxylate (98)

To a solution of N-chlorocarbonyl isocycnate (106 mg, 1 mmol) in tetrahydrofuran (2 mL) was added 1-octanol (143 mg, 1.1 mmol) at −30° C. The reaction mixture was stirred at 0° C. for 1 hour and stirred at room temperature for 1 hour without ice-bath. The reaction mixture was cooled in ice-water, and triethylamine (138 mL) and the compound 89 (245 mg, 0.6 mmol) were added thereto. The reaction mixture was stirred at room temperature overnight, and partitioned between phosphate buffer (pH 6.4) and ethyl acetate. The organic layer was separated, dried over sodium sulfate, and concentrated under reduced pressure. The obtained residue was purified by chromatography on a silica gel column (eluate: ethyl acetate) to give the compound 98 (294 mg, 81%). Mp. 118–120° C. (ether - hexane) Rf 0.38 (EtOAc). $^1$H-NMR (CDCl$_3$): δH0.88 (3 H, t like, CH$_3$), 1.25 - 1.30 (10 H, m, —CH$_2$—), 1.31 (6 H, d, J 6.9 Hz, (CH$_3$)$_2$CH), 1.62 (2 H, m, —CH$_2$—), 3.18 (1 H, sep, J 6.9 Hz, (CH$_3$)$_2$CH), 4.14 (2 H, t, J 6.9 Hz, OCH$_2$), 5.23 (2 H, s, NCH$_2$), 5.31 (2 H, s, OCH$_2$), 6.71 (2 H, d, J 1.8 Hz, arom 2- and 6-H), 6.77 (2 H, d-like, 4-pyridyl 2- and 6-H), 7.09 (1 H, bs, NH), 7.05 (1 H, t, J 1.8 Hz, arom 4-H), 8.45 (2 H, d-like, 4-pyridyl 3- and 5-H). IR (CHCl$_3$) cm$^{-1}$: 3424 (NH), 1807 and 1740 (OOCNHCOO). Elementary analysis (for C$_{29}$H$_{36}$N$_4$O$_4$SCl$_2$) Calcd. : C, 57.33% H, 5.97% N, 9.22% S, 5.28% Cl, 11.67% Found: C, 57.58% H, 6.02% N, 9.19% S, 5.30% Cl, 11.57%

EXAMPLE 83

5 -(3,5-Dichlorophenylthio)-4-isopropyl-1-(4-pyridylmethyl)-1H-imidazol-2-ylmethyl decyl iminodicaboxylate (99)

The compound 89 (245 mg, 0.6 mmol) was converted to the iminodicarboxylate with N-decanyloxycarbonyl isocyanate prepared from 1-decanol (175 mg, 1.10mmol) and N-chlorocarbonylisocyanate (106 mg, 1 mmol) in the same manner as the example 82 to give the compound 99 (315 mg, 83%). Mp. 105–107° C. Rf 0.39 (EtOAc). $^1$H-NMR (CDCl$_3$): δH0.88 (3 H, t like, CH$_3$), 1.25–1.30 (14 H, m, —CH$_2$—), 1.31 (6 H, d, J 6.9 Hz, (CH$_3$)$_2$CH), 1.62 (2 H, m, —CH$_2$—), 3.18 (1 H, sep, J 6.9 Hz, (CH$_3$)$_2$CH), 4.14 (2 H, t, J 6.9 Hz, CH$_2$O), 5.23 (2H, s, NCH$_2$), 5.31 (2H, s, OCH$_2$), 6.71 (2H, d, J 1.8 Hz, arom 2- and 6-H), 6.77 (2 H, d-like, 4-pyridyl 2- and 6-H), 6.99 (1 H, bs, NH), 7.06 (1 H, t, J 1.8 Hz, arom 4-H), 8.45 (2 H, d-like, 4-pyridyl 3- and 5-H). IR(CHCl$_3$)cm$^{-1}$: 3424 (NH), 1807 and 1739 (OOCNCOO). Elementary analysis (for C$_{31}$H$_{40}$N$_4$O$_4$SCl$_2$) Calcd. : C, 58.58% H, 6.34% N, 8.81% S, 5.04% Cl, 11.15% Found: C, 58.57% H, 6.37% N, 8.77% S, 5.02% Cl, 10.88%

EXAMPLE 84

5-(3,5-Dichlorophenylthio)-4-isopropyl-1-(4-pyridylmethyl)-1H-imidazol-2-ylmethyl octadecyl iminodicaboxylate (100)

The compound 89 (245 mg, 0.6 mmol) was converted to the iminodicarboxylate with N-octadecanyloxycarbonyl isocyanate prepared from 1-octadecanol (297 mg, 1.1 mmol) and N-chloroarbonyl isocyanate (106 mg, 1 mmol) in the same manner as the example 82 to give the compound 100 (295 mg, 66%). Mp. 96–98° C. Rf 0.46 (EtOAc). $^1$H-NMR (CDCl$_3$): δH0.88 (3 H, t like, CH$_3$), 1.25–1.30 (30 H, m, —CH$_2$—), 1.31 (6 H, d, J 6.9 Hz, (CH$_3$)$_2$CH), 1.62 (2 H, m, —CH$_2$—), 3.18 (1 H, sep, J 6.9 Hz, (CH$_3$)$_2$CH), 4.14 (2 H, t, J 6.9 Hz, CH$_2$O), 5.23 (2 H, s, NCH$_2$), 5.31 (2 H, s, OCH$_2$), 6.71 (2 H, d, J 1.8 Hz, arom 2- and 6-H), 6.77 (2 H, d-like, 4-pyridyl 2- and 6-H), 6.95 (1 H, bs, NH), 7.06 (1 H, t, J 1.8 Hz, arom 4-H), 8.45 (2 H, d-like, 4-pyridyl 3- and 5-H). IR(CHCl$_3$)cm$^{-1}$: 3394 (NH), 1791 and 1764 (NCO), 1715 (NCOO). Elementary analysis (for $C_{39}H_{56}N_4O_4SCl_2$) Calcd.: C, 62.64% H, 7.55% N, 7.49% S, 4.29% Cl, 9.48% Found: C, 62.86% H, 7.73% S, 7.43% S, 4.00% Cl, 9.07%

EXAMPLE 85

5-(3,5-Dichlorophenylthio)-4-isopropyl-1-(4-pyridylmethyl)-1H-imidazol-2-ylmethyl oleyl iminodicaboxylate (101)

The compound 89 (367 mg, 0.9 mmol) was converted to the iminodicarboxylate with N-oleyloxycarbonyl isocyanate prepared from 1-oleyl alcohol (295 mg, 1.1 mmol) and N-chlorocarbonylisocyanate (106 mg, 1 mmol) in the same manner as the example 82 to give the compound 101 (405 mg, 60%). Rf 0.47 (EtOAc). $^1$H-NMR (CDCl$_3$): $\delta$H0.88 (3 H, t like, CH$_3$), 1.26 (22 H, bs, —CH$_2$—), 1.31 (6 H, d, J 6.9 Hz, (CH$_3$)$_2$CH), 1.62 (2 H, m, —CH$_2$—), 2.01 (4 H, m, CH$_2$CH=CHCH$_2$), 3.09 (1 H, sep, J 6.9 Hz, (CH$_3$)$_2$CH), 4.14 (2 H, t, J 6.9 Hz, OCH$_2$), 5.23 (2 H, s, NCH$_2$), 5.31 (2 H, s, OCH$_2$), 5.35 (2 H, m, CH=CH), 6.71 (2 H, d, J 1.8 Hz, arom 2- and 6-H), 6.76 (2 H, d-like, 4-pyridyl 2- and 6-H), 7.05 (2 H, m, arom 4-H and NH), 8.44 (2 H, d-like, 4-pyridyl 3- and 5-H). IR (CHCl$_3$)cm$^{-1}$: 3423 (NH), 1807 and 1739 (OOCNCOO). Elementary analysis (for $C_{39}H_{54}N_4O_4SCl_2$) Calcd.: C, 62.80% H, 7.30% N, 7.51% S, 4.30% Cl, 9.51% Found: C, 62.87% H, 7.32% N, 7.43% S, 4.26% Cl, 9.39%

EXAMPLE 86

5-(3,5-Dichlorophenylthio)-4-isopropyl-1-(4-pyridylmethyl)-1H-imidazol-2-ylmethyl 2,6-diisopropylphenyl iminodicaboxylate (102)

The compound (245 mg, 0.6 mmol) was converted to the iminodicarboxylate with N-2,6-diisopropylphenyloxycarbonyl isocyanate prepared from 2,6-diisopropylphenol (196 mg, 1.1 mmol) and N-chlorocarbonylisocyanate (106 mg, 1 mmol) in the same manner as the example 82 to give the compound 102 (356 mg, 90%). Mp. 177–179° C. Rf 0.65 (EtOAc). $^1$H-NMR (CDCl$_3$): $\delta$H1.19 (12 H, d, J 7.0 Hz, 2 x (CH$_3$)$_2$CH),1.32 (6 H, d, J 6.8 Hz, (CH$_3$)$_2$CH), 2.91(2 H, sep, J 7.0 Hz, 2 x (CH$_3$)$_2$CH), 3.21(1 H, sep, J 6.8 Hz, (CH$_3$)$_2$CH), 5.29 (2 H. s, NCH$_2$), 5.35 (2 H. s, OCH$_2$), 6.71 (2 H, d, J 1.8 Hz, arom 2- and 6-H), 6.79 (2 H, d-like, 4-pyridyl 2- and 6-H), 7.05 (1 H, t, J 1.8 Hz, arom 4-H), 7.13 - 7.25 (3 H, m, 2,6-diisopropylphenyl), 7.62 (1 H, bs, NH), 8.46 (2 H, d-like, 4-pyridyl 3- and 5-H). IR(CHCl$_3$)cm$^{-1}$: 3418 (NH), 1818 and 1746 (OOCNCOO). Elementary analysis (for $C_{33}H_{36}N_4O_4SCl_2$) Calcd.: C, 60.45% H, 5.53% N, 8.55% S, 4.89% Cl, 10.81% Found: C, 60.47% H, 5.67% N, 8.44% S, 5.04% Cl, 10.53%

EXAMPLE 87

5-(3,5-Dichlorophenylthio)-4-isopropyl-1-(4-pyridylmethyl)-1H-imidazol-2-ylmethyl 4-biphenyl iminodicaboxylate (103)

The compound 89 (245 mg, 0.6 mmol) was converted to the iminodicarboxylate with N-4-biphenyloxycarbonyl isocyanate prepared from 4-phenylphenol (187 mg, 1.1 mmol) and N-chlorocarbonylisocyanate (106 mg, 1 mmol) in the same manner as the example 82 to give the compound 103 (215 mg, 55%). Mp 105–107° C. Rf 0.40 (EtOAc). $^1$H-NMR (CDCl$_3$): $\delta$H1.32 (6 H, d, J 6.9 Hz, (CH$_3$)$_2$CH), 3.21 (1 H, sep, J 6.8 Hz, (CH$_3$)$_2$CH), 5.31 (2 H, s, NCH$_2$), 5.33 (2 H, s, OCH$_2$), 6.72 (2 H, d, J 1.5 Hz, arom 2- and 6-H), 6.78 (2 H, d-like, 4-pyridyl 2- and 6-H), 7.06 (1 H, t, J 1.5 Hz, arom 4-H), 7.18 - 7.60 (9 H, m, 4-phenylphenyl), 7.82 (1 H, bs, NH), 8.46 (2 H, d-like, 4-pyridyl 3- and 5-H). IR(CHCl$_3$) cm$^{-1}$: 3418 (NH), 1817 and 1747 (OOCNCOO). Elementary analysis (for $C_{33}H_{28}N_4O_4SCl_2$) Calcd.: C, 61.21% H, 4.36% N, 8.65% S, 4.95% Cl, 10.95% Found: C, 61.06% H, 4.38% N, 8.64% S, 4.94% Cl, 10.78%

EXAMPLE 88

5-(3,5-Dichlorophenylthio)-4-isopropyl-1-(4-pyridylmethyl)-1H-imidazol-2-ylmethyl 1-naphthyl iminodicaboxylate (104)

The compound 89 (245 mg, 0.6 mmol) was converted to the iminodicarboxylate with N-1-naphthyloxycarbonyl isocyanate prepared from 1-naphthol (158 mg, 1.1 mmol) and N-chlorocarbonylisocyanate (106 mg, 1 mmol) in the same manner as the example 82 to give the compound 104 (169 mg, 45%). Mp 166–167° C. Rf 0.38 (EtOAc). $^1$H-NMR (CDCl$_3$): $\delta$H1.33 (6 H, d, J 6.8 Hz, (CH$_3$)$_2$CH), 3.21 (1 H, sep, J 6.9 Hz, (CH$_3$)$_2$CH), 5.33 (4 H, s, NCH$_2$ and OCH$_2$), 6.72 (2 H, d, J 1.6 Hz, arom 2- and 6-H), 6.78 (2 H, d-like, 4-pyridyl 2- and 6-H), 7.05 (1 H, t, J 1.6 Hz, arom 4-H), 7.30 - 7.91 ( 7 H, m, 1-naphthyl), 8.04 (1 H, bs, NH), 8.45 (2 H, d-like, 4-pyridyl 3- and 5-H). IR(CHCl$_3$)cm$^{-1}$: 3418 (NH), 1820 and 1748 (OOCNCOO). Elementary analysis (for $C_{31}H_{26}N_4O_4SCl_2$) Calcd.: C, 59.91% H, 4.22% N, 9.01% S, 5.16% Cl, 11.41% Found: C, 59.34% H, 4.12% N, 9.27% S, 5.24% Cl, 11.16%

EXAMPLE 89

Bis[5-(3,5-dichlorophenylthio)-4-isopropyl-1-(4-pyridylmethyl)-1H-imidazol-2-ylmethyl] iminodicaboxylate (105)

To a solution of the compound 89 (571 mg, 1 mmol) and triethylamine (202 mg, 2 mmol) in tetrahydrofuran was added a solution of N-chlorocarbonyl isocyanate (74.0 mg., 0.7 mmol) in tetrahydrofuran under ice-cooling. The reaction mixture was stirred under ice-cooling for 30 minutes, and stirred at room temperature for 1 hour without ice-water. The reaction mixture was partitioned between phosphate buffer (pH 7) and ethyl acetate. The organic layer was separated, and purified by chromatography on a silica gel column (eluate: ethyl acetate) to give the compound 105 (418 mg, 67%). Mp. 102–106° C. Rf 0.18 (10:1 EtOAc - CH$_3$OH). $^1$H-NMR (CDCl$_3$): $\delta$H1.30 (12 H, d, J 7.0 Hz, 2 x (CH$_3$)$_2$CH), 3.18 (2 H, sep, J 7.0 Hz, 2 x (CH$_3$)$_2$CH), 5.20 (4 H. 5, 2 x NCH$_2$CH$_2$), 5.28 (4 H. 5, 2 x NCH$_2$CH$_2$), 6.70 (4 H, d, J 1.6 Hz, 2 x arom 2- and 6-H), 6.74 (4 H, d-like, 2 x 4-pyridyl 2- and 6-H), 7.05 (2 H, t, J 1.6 Hz, 2 x arom 4-H), 7.28 (1 H, bs, NH), 8.42 (4 H, d-like, 2 x 4-pyridyl 3- and 5-H). IR (CHCl$_3$)cm$^{-1}$: 3417 (NH),1809 and 1742 (OOCNCOO). LSIMS: m/z 884 [M+H]+. Elementary analysis (for $C_{40}H_{37}N_7O_4S_2Cl_4$) Calcd.: C, 54.24% H, 4.21% N, 11.07% S, 7.24% Cl, 16.01% Found: C, 54.03% H, 4.46% N, 10.94% S, 7.21% Cl, 15.78%

EXAMPLE 90

5-(3,5-Dichlorophenylthio)-4-isopropyl-1-methyl-1H-imidazol-2-ylethyl undecanoate (106)

To a solution of the compound 22 (345 mg, 1 mmol), undecanoic acid (186 mg, 1 mmol) and N,N-dimethylaminopyridine (122 mg, 1 mmol) in methylene chloride (3 mL) was added 1,3-dihexylcarbodiimide (206 mg, 1 mmol) under ice-cooling, and stirred at room temperature overnight. The precipitated insoluble matter was filtered, and the filtrate was concentrated. The residue was purified by chromatography on a silica gel column (hexane - ethyl acetate (1:1)) to give the compound 106 (461 mg, 90%) as oil. Rf 0.50 (1:1 EtOAc - hexane). $^1$H-NMR (CDCl$_3$): δH0.88 (3 H, S, t-like, CH$_3$), 1.23 (6 H, d, J 6.9 Hz, (CH$_3$)$_2$CH), 1.25 (14 H, bs, —CH$_2$—), 3.09 (1 H, sep, J 6.9 Hz, (CH$_3$)$_2$CH), 3.10 (2 H, t, J 7.2 Hz, CH$_2$), 3.49 (3 H, s, NCH$_3$), 4.42 (2 H, t, J 7.2 Hz), 6.80 (2 H, d, J 1.8 Hz, arom 2- and 6-H), 7.11 (1 H, t, J 1.8 Hz, arom 4-H) Elementary analysis (for C$_{26}$H$_{38}$N$_2$O$_2$SCl$_2$) Calcd. : C, 60.81% H, 7.46% N, 5.45% S, 6.24% Cl, 13.81% Found: C, 60.55% H, 7.39% N, 5.54% S, 6.14% Cl, 13.81%

EXAMPLE 91

Bis [5-(3,5-dichlorophenylthio)-4-isopropyl-1-methyl-1H-imidazol-2- ylethyl] carbonate (107)

To a solution of the compound 22 (345 mg, 0.440 mmol) and triethylamine (0.276 mL, 2 mmol) in tetrahydrofuran (2 mL) was added triphosgene (60.0 mg, 0.202 mmol) at −30° C. The reaction mixture was stirred at 0° C. for 2 hours, and allowed to warm up to room temperature after stopping cooling. The reaction mixture was partitioned between ethyl acetate and a phosphate buffer (pH 6.4). The organic layer was separated, washed with water, dried over magnesium sulfate, and concentrated under reduced pressure. The residue was purified by chromatography on a silica gel column (eluate: ethyl acetate) to give the compound 107 (53 mg, 15%). mp. 157–159° C. Rf 0.25 (EtOAc). $^1$H-NMR (CDCl$_3$): δH1.22 (6H, d, J 6.9 Hz, (CH$_3$)$_2$CH), 3.08 (1 H, sep, J 6.9 Hz, (CH$_3$)$_2$CH), 3.13 (2 H, t, J 6.6 Hz, CH$_2$CH$_2$O), 3.45 (3 H, s, CH$_3$), 4.49 (2 H, t, J 6.6 Hz, CH$_2$CH$_2$O), 6.79 (2 H, d, J 1.8 Hz, arom 2- and 6-H), 7.10 (1 H, t, J 1.8 Hz, arom 4-H). IR (CHCl$_3$)cm$^{-1}$: 1747 (OCOO). LSIMS: m/z 715 (M+H)+. Elementary analysis (for C$_{31}$H$_{34}$N$_4$O$_3$S$_2$C$_4$) Calcd. : C, 51.96% H, 4.78. N, 7.82% S, 8.95% Cl, 19.79% Found: C, 53.32% H, 4.86% N, 7.73% S, 9.07% Cl, 19.36%

EXAMPLE 92

5-(3,5-Dichlorophenylthio)-1-ethyl-4-isopropyl-1H-imidazol-2-ylmethyl octanoate (108)

The compound 19 was converted to the ester with octanoic acid under N,N-dimethylaminopyridine and 1,3-dihexylcarbodiimide in the same manner as the example 90 to give the compound 108. Rf 0.63 (1:2 EtOAc-hexane ). $^1$H-NMR (CDCl$_3$): δH0.86 (3 H, t like, CH$_3$), 1.22 (3 H, t, J 7.2 Hz, CH$_3$), 1.25 (6 H, d, J 7.0 Hz, (CH$_3$)$_2$CH), 1.18–1.25 (8 H, m, —CH$_2$—), 1.63 (2 H, m, —CH$_2$—), 2.37 (2 H, t, J 7.4 Hz, —COCH$_2$—), 3.11 (1 H, sep, J 7.0 Hz, (CH$_3$)$_2$CH), 3.97 (2 H,q, J 7.0 Hz, OCH$_2$), 5.21 (2 H, s, CH$_2$O), 6.81 (2 H, d, J 1.8 Hz, arom 2- and 6-H), and 7.12 (1 H, t, J 1.8 Hz, arom 4-H). Elementary analysis (for C$_{23}$H$_{32}$N$_2$O$_2$SCl$_2$) Calcd.: C, 58.59% H, 6.84. N, 5.94% Cl, 15.04% Found: C, 58.23% H, 6.94% N, 6.04% Cl, 15.23%

EXAMPLE 93

5-(3,5-Dichlorophenylthio)-1-ethyl-4-isopropyl-1H-imidazol-2-ylmethyl decanoate (109)

The compound 19 was converted to the ester with decanoic acid under N,N-dimethylaminopyridine and 1,3-dihexylcarbodiimide in the same manner as the example 90 to give the compound 109. Rf 0.81 (1:2 EtOAc-hexane). $^1$H-NMR (CDCl$_3$): δH0.87 (3 H, t like, CH$_3$), 1.21 (3 H, t, J 7.4 Hz, CH$_3$), 1.25 (6 H, d, J 7.0 Hz, (CH$_3$)$_2$CH), 1.20-1.35 (12 H, m, —CH$_2$—), 1.62 (2 H, m, —CH$_2$—), 2.36 (2 H, t, J 7.5 Hz, —COCH$_2$—), 3.10 (1 H, sep, J 7.4 Hz, (CH$_3$)$_2$CH), 3.96 (2 H, q, 7.0 Hz, OCH$_2$), 5.20 (2 H, s, CH$_2$O), 6.81 (2 H, d, J 1.6 Hz, arom 2- and 6-H), and 7.12 (1 H, t, J 1.6 Hz, arom 4-H). Elementary analysis (for C$_{25}$H$_{36}$N$_2$O$_2$SCl$_2$) Calcd.: C, 60.11% H, 7.26% N, 5.61% Cl, 14.19%. Found. C, 60.30% H, 7.36% N, 5.63% Cl, 14.08%

EXAMPLE 94

Di-[5-(3,5-dichlorophenylthio)-4-isopropyl-1-ethyl-1H-imidazol-2-ylmethyl] carboxylate (110)

To a solution of the compound 19 (152 mg, 0.440 mmol) and triethylamine (186 mg, 0.484 mmol) in toluene (1.5 mL) was added triphosgene (21.8 mg, 0.0733 mol) under ice-cooling. The reaction mixture was stirred for 30 minutes, and the precipitated insoluble matter was filtered off. The filtrate was concentrated under reduced pressure. The residue was purified by chromatography on a silica gel column (eluate: hexane - ethyl acetate (1:1)) to give the compound 110 (16 mg, 10%). Mp. 175–177° C. Rf 0.16 (1:2 EtOAc - hexane). $^1$H-NMR (CDCl$_3$): δH 1.21 (3 H, t, J 7.2 Hz, CH$_2$CH$_3$), 1.23 (6 H, d, (CH$_3$)$_2$CH), 3.10 (1 H, sep, J 6.9 Hz, (CH$_3$)$_2$CH), 3.98 (2 H, q, J 7.2 Hz, CH$_2$CH$_3$), 5.31 (2 H, s, CH$_2$O), 6.81 (2 H, d, J 1.8 Hz, arom 2- and 6-H), 7.12 (1 H, t, J 1.8 Hz, arom 4-H). I (CHCl$_3$)cm$^{-1}$: 1752 (OCOO). LSIMS: m/z 715 (M+H) +. Elementary analysis (for C$_{31}$H$_{34}$N$_4$O$_3$S$_2$C$_4$) Calcd. : C, 51.96% H, 4.78% N, 7.82% S, 8.95% Cl, 19.79% Found: C, 51.77% H, 4.86% N, 7.68% S, 9.13% Cl, 19.49%

EXAMPLE 95

5-(3,5-Dichlorophenylthio)-4-isopropyl-1-(4-pyridylmethyl)-1H-imidazol-2-ylmethyl di-n-butylaminomethylcarbamate (112)

To a solution of 1.02 g (2.5 mM) of the compound 89 in 5 ml of tetrahydrofuran was added dropwise 0.26 ml (3 mM) of chloroacethylisocyanate with stirring at room temperature. After stirring for 45 minutes, saturated sodium hydrogencarbonate solution was added thereto. The mixture was extracted with methylene chloride, and methylene chloride layer was washed with water, dried over sodium carbonate, and evaporated for removal of methylene chloride under reduced pressure to give an oily compound. The compound was dissolved in 5 ml of aqueous methanol and stirred at room temperature. To the mixture was added 50 mg of zinc powder and stirred for 3 hours. Saturated sodium hydrogencarbonate solution was added thereto and the insoluble material was filtered off through zeolite and washed with methanol. The methanol (eluate) filtrate was concentrated under reduced pressure. The residue was dissolved in methylene chloride, washed with water, and dried over sodium carbonate After evaporation for removal of methylene chloride under reduced pressure, the oily residue was purified by chromatography on a silica gel column, eluted with ethyl acetate to give 699 mg of the compound 111 (62%) as powders. Mp. 88° C. (d) $^1$H-NMR (CDCl$_3$): δH 1.32 (d, J 7 Hz, 6H), 3.1–3.24 (m, 1H), 4.53 (br, 2H), 5.21 (s, 2H), 5.27 (s, 2H), 6.69 (d, J 1.6 Hz, 2H), 6.82 (d, J 5.2 Hz, 2H), 7.06 (t, J 1.6 Hz, 1H) 8.46 (br, 2H). Elementary analysis (for C$_{20}$H$_{20}$N$_4$O$_2$SCl$_2$.0.5H$_2$O) Calcd. : C, 52.16% H, 4.61% N, 12.17% S, 6.96% Cl, 15.42% Found: C, 52.45% H, 4.72% N, 11.73% S, 7.08% Cl, 14.81%

A suspension of the above prepared 5-(3,5-dichlorophenylthio)-4-isopropyl-1-(4-pyridylmethyl)-1H- imidazol-2-ylmethyl carbamate (111) (219 mg, 0.5 mmol), di-n-butylamine (85 mg, 0.5 mmol) and paraformaldehyde (17.5 mg, 0.583 mmol) in ethyl acetate (3mL) was heated under reflux in an atmosphere of nitrogen for 5 days. After cooling down at room temperature, the reaction mixture was concentrated under reduced pressure. The residue was dissolved in a small amount of ether, and hexane was added thereto. The precipitated insoluble material was filtered off, and the filtrate was cooled at −50° C. The purified precipitate was collected to give the compound 112 (167 mg, 66%) as oil. $^1$H-NMR (CDCl$_3$): δH 0.88 (6H, t, J 6.9 Hz, 2 x CH$_3$), 1.31 (6 H, d, J 6.9 Hz, (CH$_3$)$_2$CH), 1.20–1.42 (8 H, m, 2 x —CH$_2$—), 2.34 (4 H, t, J 7.8 Hz, 2 x —CH$_2$—), 3.17 (1 H, sep, J 6.9 Hz, (CH$_3$)$_2$CH), 4.06 (2 H, d, J 6.0 Hz, NCH$_2$NH), 4.82 (1 H, t, J 6.0 Hz, NCH$_2$NH), 5.18 (2 H, s, CH$_2$O), 5.24 (2 H, 8, NCH$_2$), 6.68 (2 H, d, J 1.5 Hz, arom 2- and 6-H), 6.79 (2 H, d-like, 4-pyridyl 2- and 6-H), 7.03 (1 H, t, J 1.5 Hz, arom 4-H), 8.42 (2 H, d-like, 4-pyridyl 3- and 5-H). Elementary analysis (C$_{29}$H$_{39}$N$_5$O$_2$SCl$_2$) Calcd. : C, 58.78% H, 6.63% N, 5.41% Cl, 11.96% Found: C, 58.72% H, 6.76% N, 11.63% S, 5.59% Cl, 11.63% hydrochloride of 112 Elementary analysis (for C$_{29}$H$_{39}$N$_6$O$_2$SCl$_5$ 3HCl 1.5H$_2$O) Calcd. : C, 47.78% H, 6.22. N, 9.61% S, 4.40% Cl, 24.31% Found: C, 47.95% H, 6.01% N, 9.77% S, 4.63% Cl, 23.93%

EXAMPLE 96

5-(3,5-Dichlorophenylthio)-4-isopropyl-1-(4-pyridylmethyl)-1H-imidazol-2-ylmethyl morpholinomethylcarbamate (113)

A suspension of the compound 111 (306 mg, 0.7 mmol), morpholine (61.0 mg, 0.7 mmol) and paraformaldehyde (22.0 mg, 0.733 mmol) in ethyl acetate (4 mL) was heated under reflux in an atmosphere of nitrogen for 3 days. After cooling down at room temperature, the residue was purified by chromatography on a silica gel column (eluate: ethyl acetate - methanol (5:1)) to give the compound 113 (265 mg, 69%). Rf 0.63 (5:1 EtOAc-CH$_3$OH). $^1$H-NMR (CDCl$_3$): δH1.30 (6 H, d, J 6.9 Hz, (CH$_3$)$_2$CH), 2.44 (4H, m, N(CH$_2$CH$_2$)$_2$O), 3.18 (1 H, sep, J 6.9 Hz, (CH$_3$)$_2$CH), 3.65 (4 H, m, N(CH$_2$CH$_2$)$_2$O), 3.91 (2 H, d, J 6.6 Hz, NCH$_2$NH), 4.98 (1 H, t, J 6.6 Hz, NCH$_2$NH ), 5.19 (2 H, s, CH$_2$O), 5.25 (2 H, s, NCH$_2$ ), 6.69 (2 H, d, J 1.8 Hz, arom 2- and 6-H), 6.71 (2 H, d-like, 4-pyridyl 2- and 6-H), 7.05 (1 H, t, J 1.8 Hz, arom 4-H), 8.45 (2 H, d-like, 4-pyridyl 3- and 5-H). Elementary analysis (for C$_{25}$H$_{29}$N$_5$O$_2$SCl$_2$) Calcd. : C, 54.55% H, 5.31% N, 12.72% S, 5.82% Cl, 12.88% Found: C, 54.37% H, 5.36% N, 12.80% S, 5.92% Cl, 12.64% hydrochloride of 113 Elementary analysis (for C$_{25}$H$_{32}$N$_5$O$_3$SCl$_5$ 3HCl 3H$_2$O) Calcd. : C, 42.06% H, 5.36% N, 9.81% S, 4.40% Cl, 24.83% Found: C, 42.01% H, 5.34% N, 10.01% S, 4.73% Cl, 24.92%.

EXAMPLE 97

5-(3,5-Dichlorophenylthio)-4-isopropyl-1-(4-pyridylmethyl)-1H-imidazol-2-ylmethyl dibenzylaminomethylcarbamate (114)

A mixture of the compound 111 (306 mg, 0.7 mmol), dibenzylamine (138 mg, 0.7 mmol) and paraformaldehyde (22.0 mg., 0.733 mmol) in ethyl acetate (4 mL) was heated under reflux in an atmosphere of nitrogen for 8 hours. After cooling down at room temperature, the reaction mixture was purified by chromatography on a silica gel column (eluate: ethyl acetate) to give the compound 114 (295 mg, 64%). Rf 0.70 (EtOAc). $^1$H-NMR (CDCl$_3$): δH1.31 (6 H, d, J 6.6 Hz, (CH$_3$)$_2$CH), 3.18 (1 H, sep, J 6.6 Hz, (CH$_3$)$_2$CH), 3.57 (4H, s, 2 x benzyl-CH$_2$), 4.04 (2 H, d, J 6.0 Hz, NCH$_2$NH), 4.88 (1H, t, 6.0 Hz, NCH$_2$NH), 5.19 (2 H, s, CH$_2$O), 5.24 (2 H, s, NCH$_2$), 6.68 (2 H, d, J 1.5 Hz, arom 2- and 6-H), 6.78 (2 H, d-like, 4-pyridyl 2- and 6-H), 7.03 (1 H, t, J 1.5 Hz, arom 4-H), 7.20-7.35 (10 H, m, 2 x benzyl), 8.43 (2 H, d-like, 4-pyridyl 3- and 5-H). Elementary analysis (for C$_{35}$H$_{35}$N$_5$O$_2$SCl$_2$) Calcd.: C, 63.63% H, 5.34% N, 10.60% S, 4.85% Cl, 10.73% Found: C, 63.39% H, 5.44% N, 10.63% S, 4.88% Cl, 10.53% The above compounds are shown as follows.

(Example 1~8)

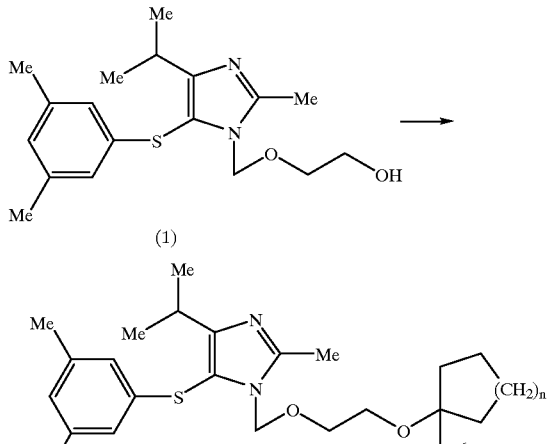

(1)

2 R$^6$ = Me  n = 1
3 R$^6$ = Me  n = 2
4 R$^6$ = Me  n = 3
5 R$^6$ = Me

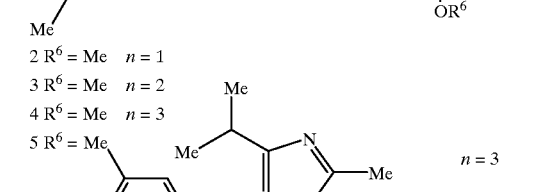

n = 3

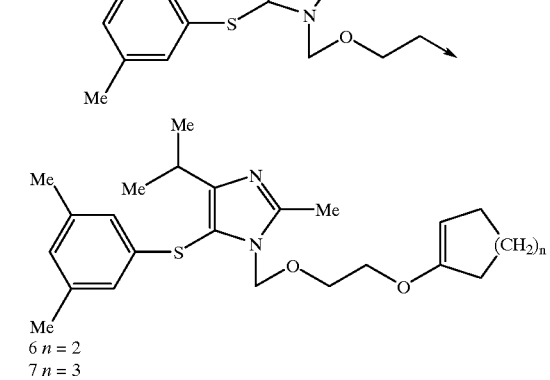

6 n = 2
7 n = 3

(Example 9~13)

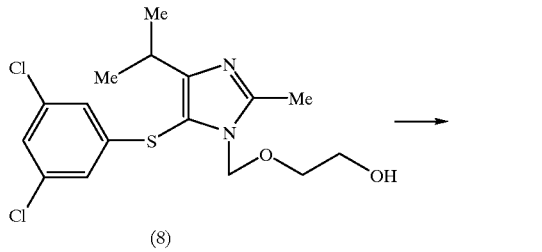

(8)

-continued

9 R⁶ = Me  n = 3

10 n = 3
11 n = 4
12 n = 6
13 n = 8

(Example 14~17)

(14)

15 R⁶ = Me  n = 2
16 R⁶ = n-Bu  n = 2

17 n = 2
18 n = 4

(Example 18~19)

(19)

-continued

20 R⁶ = n-C₄H₉  n = 1
21 R⁶ = n-C₄H₉  n = 2

(Example 20~35)

(22)

23 R³ = adamantyl-OMe
24 R³ = adamantyl-OEt
25 R³ = cycloheptyl(7)-OMe
26 R³ = cycloheptyl(7)-OEt
27 R³ = cycloheptyl(7)-OPr-n
28 R³ = cycloheptyl(7)-OBu-i 32 R³ = cyclooctyl(8)-OBu-n
33 R³ = cyclododecyl(12)-OEt
34 R³ = cyclohexyl(6)-OBu-n
35 R³ = cyclopentyl(5)-OBu-n
36 R³ = cyclopentyl(5)-OHex-n
37 R³ = bornyl(Me, O)

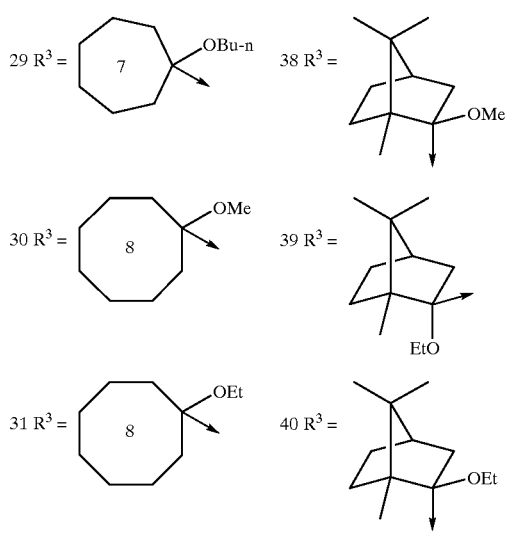
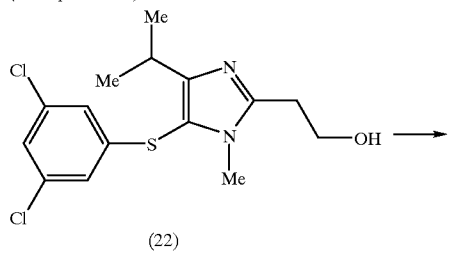
(Example 36~47)
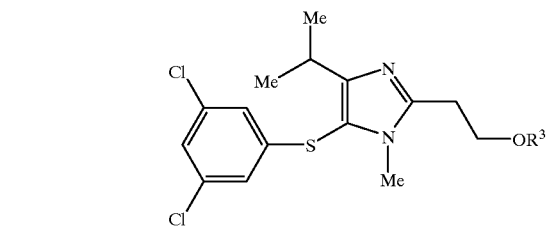
(22)
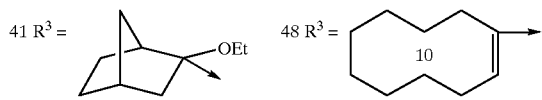
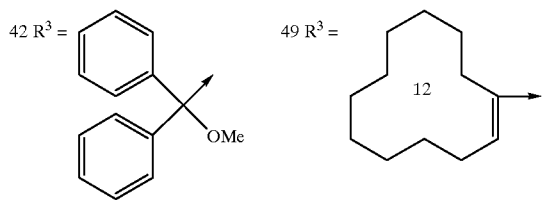
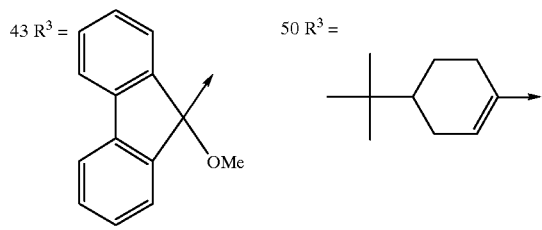
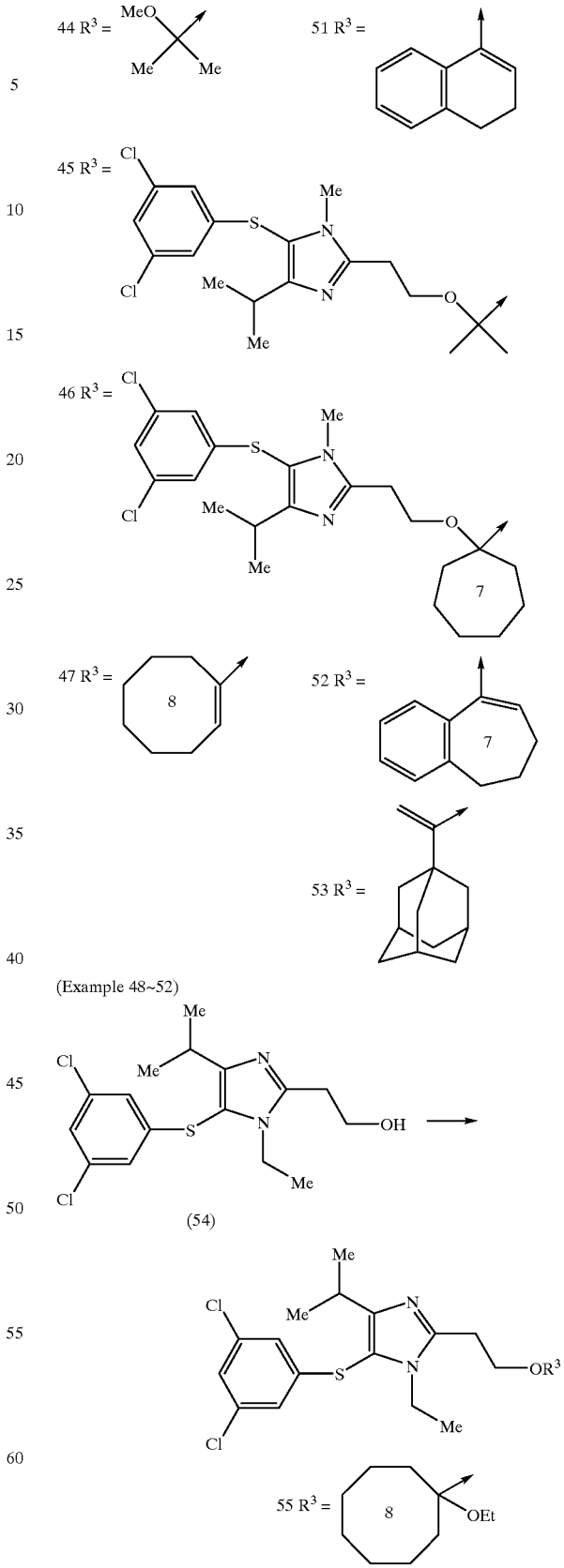

| | |
|---|---|
| 56 R³ = 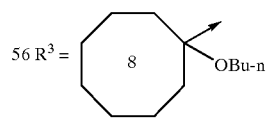 | 58 R³ = 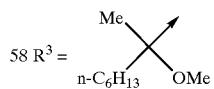 |
| 57 R³ = 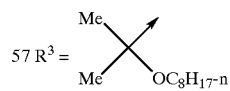 | 59 R³ = 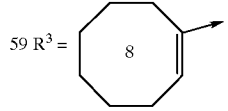 |
(Example 53~64)
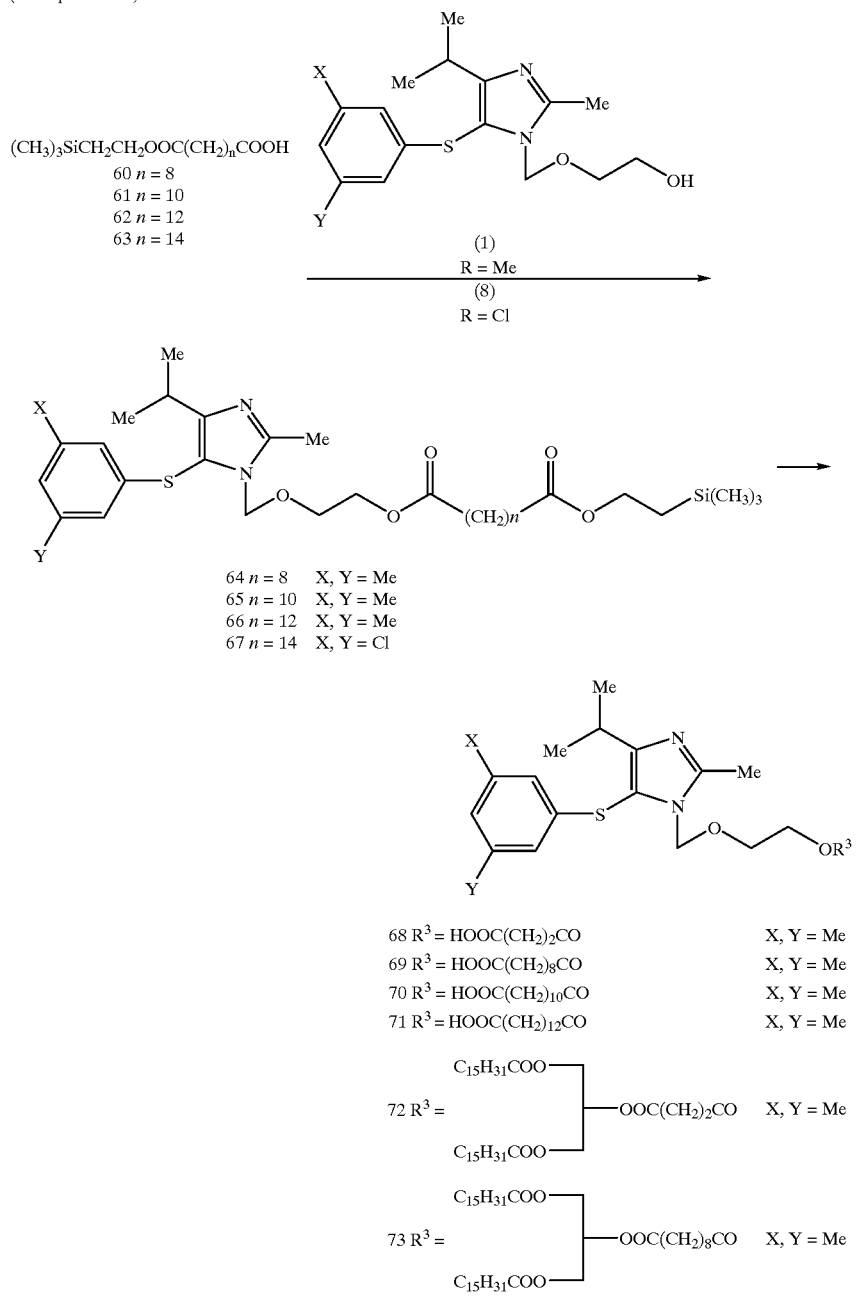

-continued

74 R³ = Me₃CCOOCH₂OOC(CH₂)₂CO    X, Y = Me
75 R³ = HOOC(CH₂)₁₄CO    X, Y = Cl
76 R³ = HOOC(CH₂)₂CO    X, Y = Cl
77 R³ = Me₃CCOOCH₂    X, Y = Cl
78 R³ = Me₃CCOOCH₂OOC(CH₂)₂CO    X, Y = Cl
79 R³ = Me₃CCOOCH₂OOC(CH₂)₁₄CO    X, Y = Cl (Example 65~73)

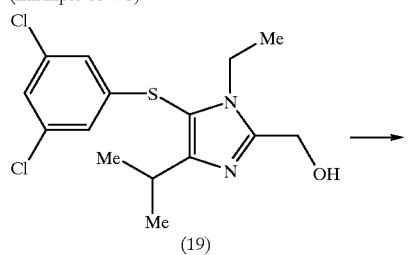

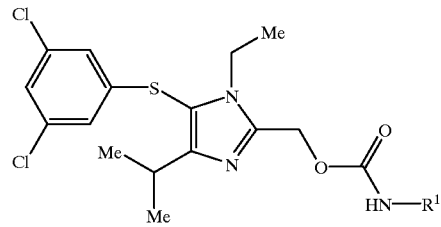

80 R¹⁴′ = CH₃CO
81 R¹⁴′ = (CH₃)₃CCO
82 R¹⁴′ = C₇H₁₅CO
83 R¹⁴′ = C₉H₁₉CO
84 R¹⁴′ = C₁₁H₂₃CO
85 R¹⁴′ = C₁₅H₃₁CO

86 R¹⁴′ = Cl—C₆H₄—CO

87 R¹⁴′ = (3,5-diCl-C₆H₃)—CO

88 R¹⁴′ = 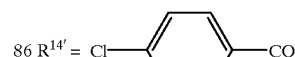

(Example 74~81)

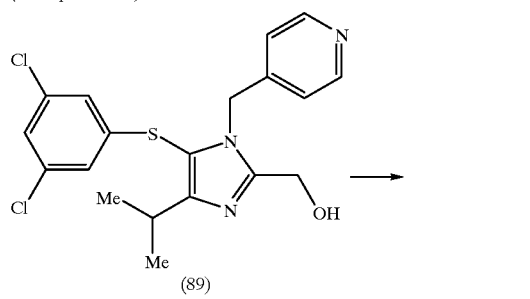

-continued

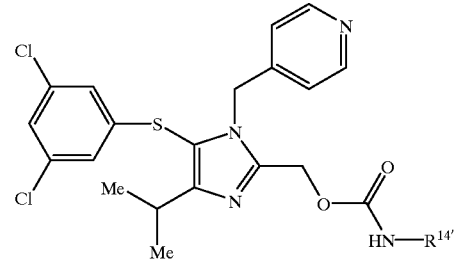

90 R¹⁴′ = CH₃CO
91 R¹⁴′ = C₇H₁₅CO
92 R¹⁴′ = C₉H₁₉CO
93 R¹⁴′ = C₁₁H₂₃CO
94 R¹⁴′ = C₁₃H₂₇CO
95 R¹⁴′ = C₁₅H₃₁CO
96 R¹⁴′ = C₁₇H₃₅CO
97 R¹⁴′ = CH₃(CH₂)₇CH=CH(CH₂)₇CO (Example 82~89)

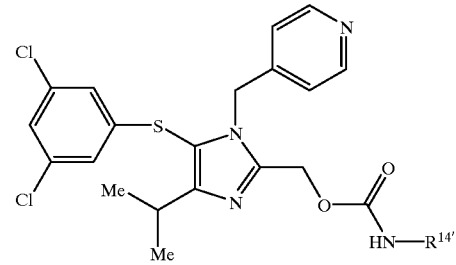

98 R¹⁴′ = C₈H₁₇OCO
99 R¹⁴′ = C₁₀H₂₁OCO
100 R¹⁴′ = C₁₈H₃₇OCO
101 R¹⁴′ = CH₃(CH₂)₇CH=CH(CH₂)₈OCO

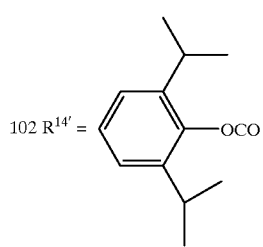
102 R$^{14'}$ =
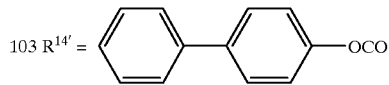
103 R$^{14'}$ =
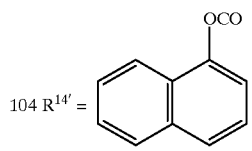
104 R$^{14'}$ =
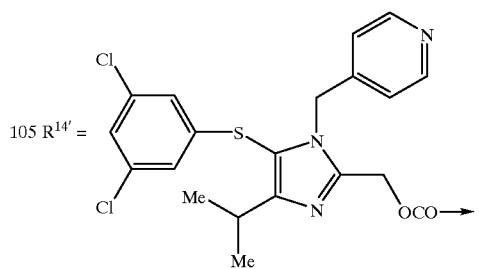
105 R$^{14'}$ =
(Example 90~94)
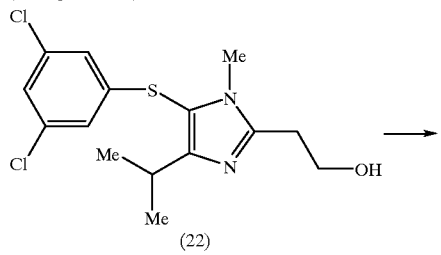
(22)
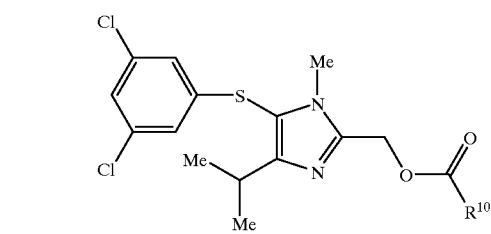
106 R$^{10}$ = n-C$_{10}$H$_{21}$
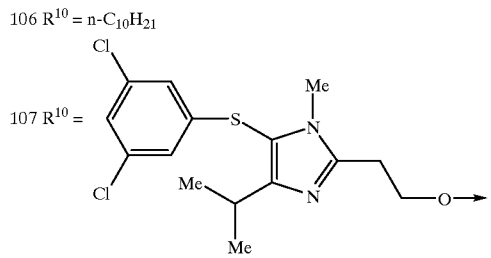
107 R$^{10}$ =
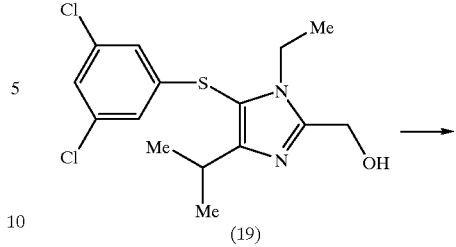
(19)
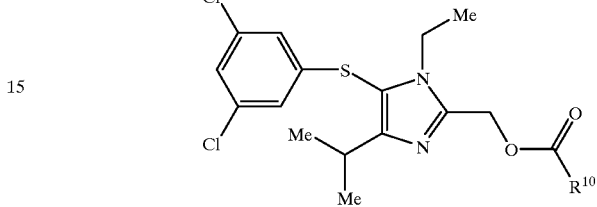
108 R$^{10}$ = n-C$_7$H$_{15}$
109 R$^{10}$ = n-C$_9$H$_{19}$
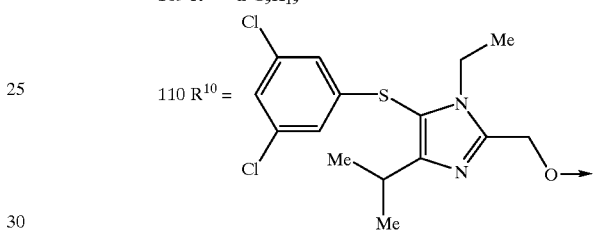
110 R$^{10}$ =
(Example 95~97)
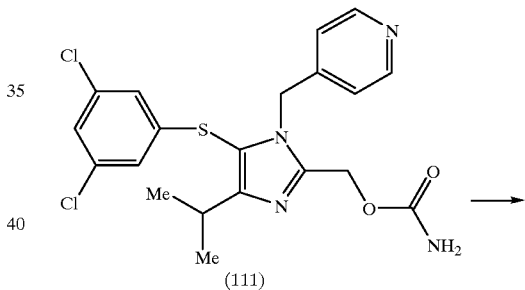
(111)
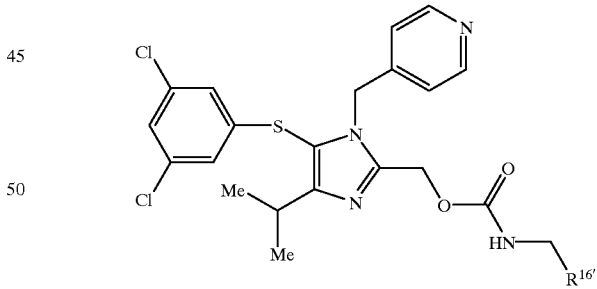
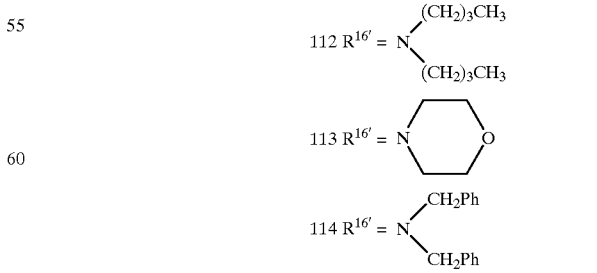
112 R$^{16'}$ = N((CH$_2$)$_3$CH$_3$)$_2$
113 R$^{16'}$ = N-morpholine
114 R$^{16'}$ = N(CH$_2$Ph)$_2$

Test EXAMPLE 1

Infection inhibitory activity of the compound

The anti-HIV activity of the representative compounds prepared in the above examples was assayed by the following procedures.

Human T cell line MOLT-4 clone 8 persistently infected by HIV (HTLV-IIIB strain) was cultured in an RPMI-1640 medium supplemented with 10% fetal calf serum, the culture supernatant was filtered, the titer of virus was determined on the filtrate, and the culture supernatant was stored at $-80°$ C. On the other hand, the test compound was diluted with the above culture medium to predetermined concentration range 1 $\mu$g/ml to 1 ng/ml and distributed in 50 $\mu$l aliquots into a 96-well microtiter plate. Then, a suspension of MT-4 cells was added in 100 $\mu$l aliquots ($3.5 \times 10^4$ cells per well) and then 50 $\mu$l (60 pfu (plaque forming units)) per well of the above HIV-containing supernatant diluted with the above culture medium each was added.

The plate was incubated in a $CO_2$ incubator at 37° C. for 5 days. Then, 30 $\mu$l/well of 3-(4,5-dimethylthiazol-2-yl)-2,5-diphenyl bromide (MTT) and 5 mg/ml PBS was added and the incubation was further continued for 1 hour. The surviving cells reducing MTT yield precipitation of formazan. Therefore, 150 $\mu$l portions of the culture supernatant were removed from all wells and, instead, 150 $\mu$l of a solution (10% Triton X-100 and 0.4% (v/v) HCl added isopropanol) was added. The plate was shaken on a plate mixer to dissolve the formazan. The OD of formazan was measured with a microreader at 560 nm and 690 nm (reference wavelength) and the result was compared with that of control. The cytotoxic effect for the virus was expressed as $EC_{50}$. The results are shown in Table 1.

TABLE 1

| Compd. No. | $EC_{50}$ ($\mu$g/ml) | Compd. No. | $EC_{50}$ ($\mu$g/ml) |
|---|---|---|---|
| 1 | 0.008 | 86 | 0.008 |
| 8 | 0.005 | 87 | 0.008 |
| 11 | 0.008 | 90 | <0.008 |
| 14 | 0.016 | 91 | 0.008–0.016 |
| 19 | 0.004 | 92 | <0.008 |
| 54 | 0.002 | 103 | 0.008 |
| 59 | 0.0025–0.005 | 104 | <0.008 |
| 68 | 0.008 | 108 | 0.008 |
| 75 | 0.008 | 109 | 0.008–0.016 |
| 76 | 0.008 | 111 | 0.0009 |
| 77 | 0.008 | 112 | 0.003 |
| 80 | 0.001 | 113 | 0.003–0.005 |
| 82 | 0.008–0.016 | 114 | 0.003–0.005 |

The representative compounds of the present invention were assayed on the lymph absorption and the in vivo hydrolysis. ① The ketal type and the enol ether type derivatives showed a high lymph absorption for oral administration in rats and showed about 40 times higher concentration in the mesenteric lymph node and about 20 times higher concentration in the plasma, compared to the imidazole derivatives having an alcoholic hydroxy group. ② The N-acylcarbamate type derivatives and the N-alkoxycarbamate type derivatives were gradually hydrolyzed in a phosphate buffer (pH 7.4) - ethanol to be converted to active imidazole derivatives having a hydroxy group and active imidazole derivatives having a carbamoyloxy group. Further, the compounds in the plasma were rapidly hydrolyzed rather than those in the buffer to be converted to imidazole derivatives having a carbamoyloxy group and imidazole derivatives having a hydroxy group. ③ The N-mannich base type derivatives were hydrolyzed in a phosphate buffer (pH 7.4) - ethanol or in the plasma to be converted to imidazole derivatives having a carbamoyloxy group.

From the above results, the compounds of the present invention show a high lymph absorption and are readily converted by in vivo hydrolysis into active parent compounds.

The compounds of the invention are effectively absorbed from the lymph vessel in the intestinal tract and transferred to the lymph node in a high concentration. Accordingly, at least the following effect is expected.

1) The compounds are expected to show the activity in the lymph node, which contributes to anti-HIV effect.

Some of the compounds of the present invention which are absorbed in the lymph and converted by in vivo hydrolysis into the derivatives having an alcoholic hydroxy group or a carbamoyloxy group are desirable as anti-AIDS agents because they show particularly potent anti-HIV activity.

Further, some of the compounds of the present invention are absorbed in the lymph, without in vivo hydrolysis, to show anti-HIV activity with the structure unchanged. Accordingly, the following effect is expected.

2) The bioavailability is improved by the avoidance of first-pass effect in liver and the distribution in the lymph node is enlarged. Further, safe pharmaceutical compositions with reduced hepatotoxicity are provided.

INDUSTRIAL APPLICABILITY

The invention provides pharmaceutical compositions which show anti-AIDS activity and a high lymph absorption.

We claim:

1. A compound of the formula (I):

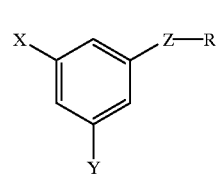

wherein X and Y each is independently hydrogen, lower alkyl, halogen or nitro;

Z is S, SO, $SO_2$ or $CH_2$; and

R is a group of the formula:

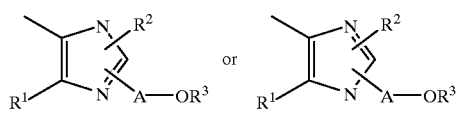

wherein $R^1$ is lower alkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio;

$R^2$ is lower alkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, lower alkenyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, cycloalkylalkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, lower aroylalkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, aralkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, heteroarylalkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, or carbamoyloxyalkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio;

A is lower alkylene which is uninterrupted or is interrupted by a hetero atom; and $R^3$ is 1) $C_{11}$–$C_{20}$ alkyl, 2) acyloxyalkyl,

3) —$CR^4R^5(OR^6)$ wherein $R^4$ and $R^5$ each is independently hydrogen, alkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, aryl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, aralkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, or taken together form cyclic alkyl unsubstituted or substituted with allyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, or o-biphenylenemethane when taken together with the adjacent carbon atom; and $R^6$ is alkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio,

4) —$C(=CR^7R^8)R^9$ wherein $R^7$, $R^8$ and $R^9$ each is independently hydrogen, alkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, or $R^7$ and $R^9$ form cyclic alkenyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, when taken together with the adjacent carbon atom,

5) —$COR^{10}$ wherein $R^{10}$ is $C_6$–$C_{20}$ alkyl, cycloalkyl, aralkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, or —B—$COOR^{11}$, wherein B is alkylene or alkenylene; and
$R^{11}$ is hydrogen, alkyl, alkanoyloxymethyl, alkoxycarbonylmethyl, —$CH(CH_2OCOR^{12})_2$ wherein $R^{12}$ is hydrogen or alkyl, or heteroarylalkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio,

6) —$COOR^{13}$ wherein $R^{13}$ is $C_6$–$C_{20}$ alkyl, aryl substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, aralkyl, unsubstituted or substituted with alkyl, alkenyl, cycloalkyl, haloasl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, or heteroarylalkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio,

7) —$CONHCOR^{14}$ wherein $R^{14}$ is hydrogen, alkyl, alkenyl, cycloalkylalkyl, aryl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, aralkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, or heteroarylalkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio,

8) —CONHCOOR$^{15}$ wherein R$^{15}$ is alkyl, alkenyl, cycloalkylalkyl, aryl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, aralkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, or heteroarylalkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, or

9) —CONHCH$_2$NR$^{16}$R$^{17}$ wherein R$^{16}$ and R$^{17}$ each is independently alkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, aralkyl unsubstituted or substituted with alkyl, alkenyl, cycloalkyl, haloalkyl, oxoalkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, or form a heterocyclic ring when taken together with the adjacent nitrogen atom, unsubstituted or substituted with alkyl, alkenyl, cycloalkyl, haloalkyl, oxoaLkyl, aryl, aralkyl, heteroarylalkyl, aroylalkyl, substituted or unsubstituted amino, acyl, halogen, hydroxy, oxo, alkoxy, acyloxy, cyano, carboxy, alkoxycarbonyl, or phenylthio, salt thereof, or hydrate thereof.

2. The compound, the salt thereof, or the hydrate thereof as claimed in claim 1, wherein X and Y each is independently lower alkyl or halogen; Z is S; R$^1$ is isopropyl; R$^2$ is lower alkyl or heteroarylalkyl; and A is C$_1$–C$_3$ alkylene which is uninterrupted or interrupted by oxygen atom.

3. The compound, the salt thereof, or the hydrate thereof as claimed in claim 1, wherein X and Y are halogen; R$^2$ is pyridylmethyl or methyl; A is methylene or ethylene; R$^3$ is —CONHCH$_2$NR$^{16}$R$^{17}$ wherein R$^{16}$ and R$^{17}$ are as defined above, —CR$^4$R$^5$(OR$^6$) wherein R$^4$, R$^5$ and R$^6$ are as defined above, or —C(=CR$^7$R$^8$)R$^9$ wherein R$^7$, R$^8$ and R$^9$ are as defined above.

4. The compound, the salt thereof, or the hydrate thereof as claimed in claim 1, which is hydrolyzed into a compound wherein R$^3$ is hydrogen or —CONH$_2$ by in vivo hydrolysis.

5. A pharmaceutical composition comprising the compound, the salt thereof, or the hydrate thereof as claimed in claim 1.

6. An agent for treating AIDS comprising the compound, the salt thereof, or the hydrate thereof as claimed in claim 1.

* * * * *